(12) United States Patent
Tobia et al.

(10) Patent No.: US 7,622,117 B2
(45) Date of Patent: Nov. 24, 2009

(54) 3-DEOXYGLUCOSONE AND SKIN

(75) Inventors: Annette Tobia, Wyndmoor, PA (US); Francis Kappler, Philadelphia, PA (US)

(73) Assignee: Dynamis Therapeutics, Inc., Elkins Park, PA (US)

( * ) Notice: Subject to any disclaimer, the term of this patent is extended or adjusted under 35 U.S.C. 154(b) by 212 days.

(21) Appl. No.: 10/198,706

(22) Filed: Jul. 18, 2002

(65) Prior Publication Data

US 2003/0219440 A1 Nov. 27, 2003

Related U.S. Application Data

(60) Provisional application No. 60/392,530, filed on Jun. 27, 2002, provisional application No. 60/373,103, filed on Apr. 17, 2002.

(51) Int. Cl.
*A01N 37/32* (2006.01)
(52) U.S. Cl. .................. 424/146.1; 514/23; 514/528; 514/551
(58) Field of Classification Search .................. 514/23, 514/528, 551; 424/146.1
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,034,506 A | 7/1991 | Summerton et al. | |
| 6,004,958 A * | 12/1999 | Brown et al. | 514/238.8 |
| 6,040,326 A | 3/2000 | Hotta et al. | |
| 6,048,522 A * | 4/2000 | Plochocka et al. | 424/78.24 |
| 6,323,219 B1 | 11/2001 | Costanzo | |
| 6,335,023 B1 * | 1/2002 | Yu et al. | 424/401 |
| 7,071,298 B2 | 7/2006 | Brown et al. | |

FOREIGN PATENT DOCUMENTS

| | | |
|---|---|---|
| WO | WO 98/33492 | 8/1998 |
| WO | WO 9833492 A1 * | 8/1998 |
| WO | WO 99/64561 | 12/1999 |
| WO | WO 00/24405 | 5/2000 |
| WO | WO 00/62626 | 10/2000 |

OTHER PUBLICATIONS

Dyer et al. (J. Clin. Invest. 1993; 91: 2463-2469).*
Jain (Scientific American Jul. 1994).*
(MSNBC News Services, "Mixed results on new cancer drug", Nov. 9, 2000).*
Gura (Science, v278, 1997, pp. 1041-1042).*
Kappler et al. (Diabetes Technology and Therapeutics 2001; 3: 609-616).*
Foldvari et al. (Biotechnol. Appl. Biochem 1999; 30: 129-137).*
Barbas, 1995, Nature Medicine 1:837-839.
Barski et al., 1995, Biochemistry 34:11264-11275.
Baynes et al., 1984, Methods Enzymol. 106:88-98.
Beerli et al., 1996, Breast Cancer Research and Treatment 38:11-17.
Bierhaus et al., 1998, Cardiovasc. Res. 37:586-600.
Brownlee et al., 1986, Science 232:1629-1632.
Brownlee et al., 1994, Diabetes 43:836-841.
Brownlee, 1992, Diabetes Care, 15: 1835.
Bunn et al., 1981, Science, 213:222.
Burton et al., 1994, Adv. Immunol. 57:191-280.
de Kruif et al. 1995, J. Mol. Biol. 248:97-105.
Delpierre et al., 2000, Diabetes 10:1627-1634.
Dills, 1993, Am. J. Clin. Nutr. 58:S779.
Dyer et al., 1991, J. Biol. Chem. 266:11654-11660.
Edelstein et al., 1992, Diabetologia 35:96-97.
Ellis et al., 1991, Metabolism 40:1016-1019.
Eriksson et al., 1998, Diabetes 47:1960-1966.
Finot et al., 1969, Helv. Chim. Acta, 52:1488-1495.
Fujii et al., 1995, Biochem. Biophys. Res. Comm. 210:852-857.
Gu et al., 1997, Thrombosis and Hematocyst 77:755-759.
Hirsch et al., 1992, Carbohydr. Res. 232:125-130.
Kappler et al., 2002, Diabetes Technol. Ther., Winter 3:4:606-609.
Lal et al., 1995, Arch. Biochem. Biophys. 318:191-199.
Makita et al., 1992, Science 258:651-653.
Marks et al., 1991, J. Mol. Biol. 222:581-597.
Nielsen et al., 1991, Science 254: 1497-1500.
Ninomiya et al., 2001, Diabetes 50:178-179.
Niwa et al., 1993, Biochem. Biophys. Res. Commun. 196:837-843.
Niwa et al., 1995, Nephron, 69: 438-443.
Niwa et al., 1997, J. Clin. Invest. 99:1272-1280.
Okado et al., 1996, Biochem. Biophys. Res. Commun. 225:219-224.
Rahbar et al., 1999, Biochem. Biophys. Res. Commun. 262:651-660.
Soulis-Liparota et al., 1991, Diabetes 40:1328-1334.
Suzuki et al., 1998, J. Biochem. 123:353-357.
Szwergold et al., 2001, Diabetes 50:2139-2147.
Takahashi et al., 1995, Biochemistry 34:1433-1438.
Thornalley, 1996, Endocrinol. Metab. 3:149-166.
Vander Jagt et al., 1997, Biochem. Pharmacol. 53:1133-1140.
Wells-Knecht et al., 1994, Diabetes. 43:1152-1156.
Wright et al. 1992, Critical Rev. Immunol. 12:125-168.

* cited by examiner

*Primary Examiner*—Brandon J Fetterolf
(74) *Attorney, Agent, or Firm*—Drinker Biddle & Reath LLP

(57) ABSTRACT

The invention relates to a method of removing 3-deoxyglucosone and other alpha-dicarbonyl sugars from skin. The invention further relates to methods of inhibiting production and function of 3-deoxyglucosone and other alpha-dicarbonyl sugars in skin. The invention also relates to methods of treating 3-deoxyglucosone and other alpha-dicarbonyl sugars associated diseases and disorders of skin.

18 Claims, 11 Drawing Sheets

| | |
|---|---|
| 1 | cgtcaagctt ggcacgaggc catggagcag ctgctgcgcg ccgagctgcg caccgcgacc |
| 61 | ctgcgggcct tcggcggccc cggcgccggc tgcatcagcg agggccgagc ctacgacacg |
| 121 | gacgcaggcc cagtgttcgt caaagtcaac cgcaggacgc aggcccggca gatgtttgag |
| 181 | ggggaggtgg ccagcctgga ggccctccgg agcacgggcc tggtgcgggt gccgaggccc |
| 241 | atgaaggtca tcgacctgcc gggaggtggg gccgcctttg tgatggagca tttgaagatg |
| 301 | aagagcttga gcagtcaagc atcaaaactt ggagagcaga tggcagattt gcatctttac |
| 361 | aaccagaagc tcagggagaa gttgaaggag gaggagaaca cagtgggccg aagaggtgag |
| 421 | ggtgctgagc ctcagtatgt ggacaagttc ggcttccaca cggtgacgtg ctgcggcttc |
| 481 | atcccgcagg tgaatgagtg gcaggatgac tggccgacct ttttcgcccg gcaccggctc |
| 541 | caggcgcagc tggacctcat tgagaaggac tatgctgacc gagaggcacg agaactctgg |
| 601 | tcccggctac aggtgaagat cccggatctg ttttgtggcc tagagattgt ccccgcgttg |
| 661 | ctccacgggg atctctggtc gggaaacgtg gctgaggacg acgtggggcc cattatttac |
| 721 | gacccggctt ccttctatgg ccattccgag tttgaactgg caatcgcctt gatgtttggg |
| 781 | gggttccccg atccttctt caccgcctac acggaaga tccccaaggc tccgggcttc |
| 841 | gaccagcggc tgctgctcta ccagctgttt aactacctga accactggaa ccacttcggg |
| 901 | cgggagtaca ggagcccttc cttgggcacc atgcgaaggc tgctcaagta gcggcccctg |
| 961 | ccctcccttc ccctgtcccc gtccccgt |

FIG.10

| | |
|---|---|
| 1 | meqllraelr tatlrafggp gagcisegra ydtdagpvfv kvnrrtqarq mfegevasle |
| 61 | alrstglvrv prpmkvidlp gggaafvmeh lkmkslssqa sklgeqmadl hlynqklrek |
| 121 | lkeeentvgr rgegaepqyv dkfgfhtvtc cgfipqvnew qddwptffar hrlqaqldli |
| 181 | ekdyadrear elwsrlqvki pdlfcgleiv pallhgdlws gnvaeddvgp iiydpasfyg |
| 241 | hsefelaial mfggfprsff tayhrkipka pgfdqrllly qlfnylnhwn hfgreyrsps |
| 301 | lgtmrrllk |

FIG.11

3-DEOXYGLUCOSONE AND SKIN

CROSS REFERENCE TO RELATED APPLICATIONS

The present application claims priority under 35 U.S.C. §119(e) to U.S. Provisional Application No. 60/373,103 filed on Apr. 17, 2002 and to a U.S. Provisional Application No. 60/392,530 filed on Jun. 27, 2002.

STATEMENT REGARDING FEDERALLY SPONSORED RESEARCH AND DEVELOPMENT

This invention was supported in part using funds from the U.S. Government (NIH Grant No. R21 DK55079) and the U.S. Government may therefore have certain rights in the invention.

BACKGROUND OF THE INVENTION

3-Deoxyglucosone is a Potent Protein Glycating Agent Associated with Protein Crosslinking 3-deoxyglucosone (3DG) is a 1,2-dicarbonyl-3-deoxysugar which is a potent protein crosslinker, is teratogenic and/or mutagenic, causes apoptosis, mutations, and formation of active oxygen species, and is a precursor to the formation of Advanced Glycation End product (AGE) modified proteins. As reviewed by Brownlee and shown in FIG. 1, the previously generally accepted pathway for formation of 3DG comprises a reversible reaction between glucose and the $\epsilon$-$NH_2$ groups of lysine-containing proteins, forming a Schiff base (Brownlee et al., 1994, Diabetes 43:836-841). This Schiff base then rearranges to form a more stable ketoamine known as fructoselysine (FL) or the "Amadori product". The dogma has been that 3DG production resulted exclusively from subsequent non-enzymatic rearrangement, dehydration, and fragmentation of the fructoselysine containing protein (Brownlee et al., 1994, Diabetes 43:836-841 and Makita et al., 1992, Science 258:651-653) (see FIG. 1). However, more recent work has shown that an enzymatic pathway for the production of 3DG exists as well (see FIGS. 1 and 2 and Brown et al., U.S. Pat. No. 6,004,958).

A metabolic pathway was discovered which produces relatively high concentrations of 3DG in organs affected by diabetes (Brown et al., U.S. Pat. No. 6,004,958). It was found that a specific kinase converts fructose-lysine into fructose-lysine-3-phosphate (FL3P) in an ATP dependent reaction, and that FL3P then breaks down to form free lysine, inorganic phosphate, and 3DG (Brown et al., U.S. Pat. No. 6,004,958). Methods have also been described for assessing diabetic risk, based on measuring components of the 3DG pathway (WO 99/64561).

U.S. Pat. No. 6,004,958 describes a class of compounds which inhibit the enzymatic conversion of fructose-lysine to FL3P and inhibit formation of 3DG. Specific compounds which are representative of the class have also been described (Brown et al., WO 98/33492). For example, it was found in WO 98/33492 that urinary or plasma 3DG can be reduced by meglumine, sorbitollysine, mannitollysine, and galactitollysine. It was also found in WO 98/33492 that diets high in glycated protein are harmful to the kidney and cause a decrease in birth rate.

It has also been disclosed that the fructoselysine pathway is involved in kidney carcinogenesis (WO 98/33492) and that diet and 3DG may play a role in carcinogenesis associated with this pathway (WO 00/24405; WO 00/62626).

Human skin is a composite material comprising a superficial component, the epidermis, and a deep component, the dermis. The outermost layer of the epidermis is the stratum corneum. This layer is the stiffest layer of the skin, as well as the one most affected by the surrounding environment. Deep to the stratum corneum is the internal portion of the epidermis. Deep to the epidermis, is the papillary layer of the dermis, which comprises relatively loose connective tissue which defines the micro-relief of the skin. The reticular dermis, deep to the papillary dermis, is dense connective tissue that is spatially organized. The reticular dermis is also associated with coarse wrinkles. Deep to the dermis is subcutaneous connective tissue and adipose tissue.

The principal functions of the skin include protection, excretion, secretion, absorption, thermoregulation, pigmentogenesis, accumulation, sensory perception, and regulation of immunological processes. These functions are detrimentally affected by the structural changes in the skin due to aging and various diseases and disorders of the skin. The physiological changes associated with normal skin aging and photoaging include loss of elasticity, decreased collagen, collagen and elastin crosslinking, wrinkling, dry/rough texture, and mottled hyperpigmentation, for example.

The mechanical properties of the skin, such as elasticity, are controlled by the density of the network of collagen and elastic fibers coursing throughout. Damaged collagen and elastin proteins lose their contractile properties, resulting in such things as skin wrinkling and skin surface roughness. As skin ages or begins to deteriorate due to a disease or disorder, it acquires sags, stretch marks, bumps, or wrinkles, it roughens, it can become discolored, and it has reduced ability to synthesize vitamin D. Aged skin also becomes thinner and has a flattened dermoepidermal interface because of the alterations of collagen, elastin, and glycosaminoglycans.

Experimental and Clinical Evidence of the Role of 3DG in Diabetes and Other Diseases Past studies have concentrated on the role of 3DG in diabetes. It has been shown that diabetic humans have elevated levels of 3DG and 3-deoxyfructose (3DF), 3DG's detoxification product, in plasma (Niwa et al., 1993, Biochem. Biophys. Res. Commun. 196:837-843; Wells-Knecht et al., 1994, Diabetes. 43:1152-1156) and in urine (Wells-Knecht et al., 1994, Diabetes. 43:1152-1156), as compared with non-diabetic individuals. Furthermore, diabetics with nephropathy were found to have elevated plasma levels of 3DG compared to non-diabetics (Niwa et al., 1993, Biochem. Biophys. Res. Commun. 196:837-843). A recent study comparing patients with insulin-dependent diabetes mellitus (IDDM) and noninsulin-dependent diabetes mellitus (NIDDM) confirmed that 3DG and 3DF levels were elevated in blood and urine from both types of patient populations (Lal et al., 1995, Arch. Biochem. Biophys. 318:191-199). It has even been shown that incubation of glucose and proteins in vitro under physiological conditions produces 3DG. In turn, it has been demonstrated that 3DG glycates and crosslinks protein creating detectable AGE products (Baynes et al., 1984, Methods Enzymol. 106:88-98; Dyer et al., 1991, J. Biol. Chem. 266: 11654-11660). The normal pathway for reductive detoxification of 3DG (conversion to 3DF) may be impaired in diabetic humans since their ratio of urinary and plasma 3DG to 3DF differs significantly from non-diabetic individuals (Lal et al., 1995, Arch Biochem. Biophys. 318:191-199).

Furthermore, elevated levels of 3DG-modified proteins have been found in diabetic rat kidneys compared to control rat kidneys (Niwa et al., 1997, J. Clin. Invest. 99:1272-1280).

It has been demonstrated that 3DG has the ability to inactivate enzymes such as glutathione reductase, a central antioxidant enzyme. It has also been shown that Hemoglobin-AGE levels are elevated in diabetic individuals (Makita et al., 1992, Science 258:651-653) and other AGE proteins have been shown in experimental models to accumulate with time, increasing from 5-50 fold over periods of 5-20 weeks in the retina, lens and renal cortex of diabetic rats (Brownlee et al., 1994, Diabetes 43:836-841). In addition, it has been demonstrated that 3DG is a teratogenic factor in diabetic embryopathy (Eriksson et al., 1998, Diabetes 47:1960-1966).

Nonenzymatic glycation, in which reducing sugars are covalently attached to free amino groups and ultimately form AGEs, has been found to occur during normal aging and to occur at an accelerated rate in diabetes mellitus (Bierhaus et al., 1998, Cardiovasc. Res. 37:586-600). Crosslinking of proteins and the subsequent AGE formation are irreversible processes that alter the structural and functional properties of proteins, lipid components, and nucleic acids (Bierhaus et al., 1998, Cardiovasc. Res. 37:586-600). These processes have been postulated to contribute to the development of a range of diabetic complications including nephropathy, retinopathy, and neuropathy (Rahbar et al., 1999, Biochem. Biophys. Res. Commun. 262:651-660).

Recently, it has been demonstrated that inhibition of AGE formation reduced the extent of nephropathy in diabetic rats (Ninomiya et al., 2001, Diabetes 50:178-179). Therefore, substances which inhibit AGE formation and/or oxidative stress appear to limit the progression of diabetes and its complications and may offer new tools for therapeutic interventions in the therapy of diabetes (Bierhaus et al., 1998, Cardiovasc. Res. 37:586-600; Thornalley, 1996, Endocrinol. Metab. 3:149-166).

Detoxification of 3DG

3DG can be detoxified in the body by at least two pathways. In one pathway, 3DG is reduced to 3-deoxyfructose (3DF) by aldehyde reductase, and the 3DF is then efficiently excreted in urine (Takahashi et al., 1995, Biochemistry 34:1433). Another detoxification reaction oxidizes 3DG to 3-deoxy-2-ketogluconic acid (DGA) by oxoaldehyde dehydrogenase (Fujii et al., 1995, Biochem. Biophys. Res. Comm. 210:852).

Results of studies to date show that the efficiency of at least one of these enzymes, aldehyde reductase, is adversely affected in diabetes. When isolated from diabetic rat liver, this enzyme is glycated on lysine at positions 67, 84 and 140 and has a low catalytic efficiency when compared with the normal, unmodified enzyme (Takahashi et al., 1995, Biochemistry 34:1433). Since diabetic patients have higher ratios of glycated proteins than normoglycemic individuals they are likely to have both higher levels of 3DG and a reduced ability to detoxify this reactive molecule by reduction to 3DF. It has also been found that overexpression of aldehyde reductase protects PC12 cells from the cytotoxic effects of methylglyoxal or 3DG (Suzuki et al., 1998, J. Biochem. 123:353-357).

The mechanism by which aldehyde reductase works has been studied. These studies demonstrated that this important detoxification enzyme is inhibited by aldose reductase inhibitors (ARIs) (Barski et al., 1995, Biochemistry 34:11264). ARIs are currently under clinical investigation for their potential to reduce diabetic complications. These compounds, as a class, have shown some effect on short term diabetic complications. However, they lack clinical effect on long term diabetic complications and they worsen kidney function in rats fed a high protein diet. This finding is consistent with the newly discovered metabolic pathway for lysine recovery. For example, a high protein diet will increase the consumption of fructose-lysine, which in turn undergoes conversion into 3DG by the kidney lysine recovery pathway. The detoxification of the resulting 3DG by reduction to 3DF will be inhibited by ARIs therapy. Inhibiting 3DG detoxification will lead to increased 3DG levels, with a concomitant increase in kidney damage, as compared to rats not receiving AR's. This is because inhibition of the aldose reductase by the AR's would reduce availability of aldose reductase for reducing 3DG and 3DF.

Aminoguanidine, an agent which detoxifies 3DG pharmacologically via formation of rapidly excreted covalent derivatives (Hirsch et al., 1992, Carbohydr. Res. 232:125-130), has been shown to reduce AGE-associated retinal, neural, arterial, and renal pathologies in animal models (Brownlee et al., 1994, Diabetes 43:836-841; Brownlee et al., 1986, Science 232:1629-1632; Ellis et al., 1991, Metabolism 40:1016-1019; Soulis-Liparota et al., 1991, Diabetes 40:1328-1334; and Edelstein et al., 1992, Diabetologia 35:96-97).

To date, no one has studied or identified 3DG in skin, therefore, the role of 3DG in skin diseases, disorders, or conditions has not been elucidated. Skin aging, wrinkling, and the like, are the subject of much research and there is a long felt need in the art for the development of new methods to treat wrinkling or aging skin, as well as diseased skin. The present invention satisfies this need.

SUMMARY OF THE INVENTION

The present invention, as described in the disclosure provided herein, is based on the discovery that 3DG is present in skin. The invention is further based on the discovery of a metabolic pathway in which a specific kinase present in the skin and elsewhere converts fructose-lysine into fructose-lysine-3-phosphate (FL3P) in an ATP dependent reaction, and that FL3P then breaks down to form 3DG, inorganic phosphate, and free lysine. The invention therefore includes compositions and methods to inhibit enzymatically induced 3DG synthesis and accumulation in skin, compositions and methods to inhibit 3DG function or to remove 3DG from skin, as well as compositions and methods to increase the rate of detoxification and removal of 3DG from skin, based on the metabolic pathways and compositions and methods described herein.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 8, comprising FIG. 8A is an image of a photomicrograph of a glomerulus from a rat fed the glycated diet for 8 months. The glomerulus shows segmental sclerosis of the glomerular tuft with adhesion of the sclerotic area to Bowman's capsule (lower left). There is also tubular metaplasia of the parietal epithelia from approximately 9 to 3 o'clock. These sclerotic and metaplastic changes are reminiscent of the pathologies observed in diabetic kidney disease. FIG. 8B is an image from a rat on the control diet for 8 months, comprising a histologically normal glomerulus.

FIG. 10 is an image depicting the nucleic acid sequence (SEQ ID NO:1) of human amadorase (fructosamine-3-kinase), NCBI accession number NM_022158. The accession number for the human gene on chromosome 17 is NT_010663.

FIG. 11 is an image depicting the amino acid sequence (SEQ ID NO:2) of human amadorase (fructosamine-3-kinase), NCBI accession number NP_071441.

DETAILED DESCRIPTION OF THE INVENTION

General Description

The invention relates generally to methods to inhibit the production or function of 3DG in skin and to methods to remove 3DG from skin. Excess 3DG has been shown to be involved in the pathology of diabetes and other diseases, but until the present invention, the presence or absence of 3DG in the skin has not been examined. A role for 3DG in normal skin function and in skin diseases has also not been examined. It has been discovered in the present invention that 3DG is present in human skin and that the gene encoding the enzyme regulating the synthesis of 3DG is expressed in skin. The present invention further discloses compounds that can inhibit 3DG from causing crosslinking and other problems associated with wrinkling, aging, diseases, and disorders of the skin.

Definitions—

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "accumulation of 3DG" or "accumulation of alpha-dicarbonyl sugars" as used herein refers to an increase in the levels of 3DG or alpha-dicarbonyl sugars.

"Alpha-dicarbonyl sugars," as used herein, refers to a family of compounds, including 3-Deoxyglucosone, glyoxal, methyl glyoxal and glucosone.

"Alpha-dicarbonyl sugar associated parameter of wrinkling, aging, disease or disorder of the skin," as used herein, refers to the biological markers described herein, including 3DG levels, 3DF levels, fructosamine kinase levels, protein crosslinking, and other markers or parameters associated with alpha-dicarbonyl sugar associated wrinkling, aging, diseases or disorders of the skin.

Figure 1:
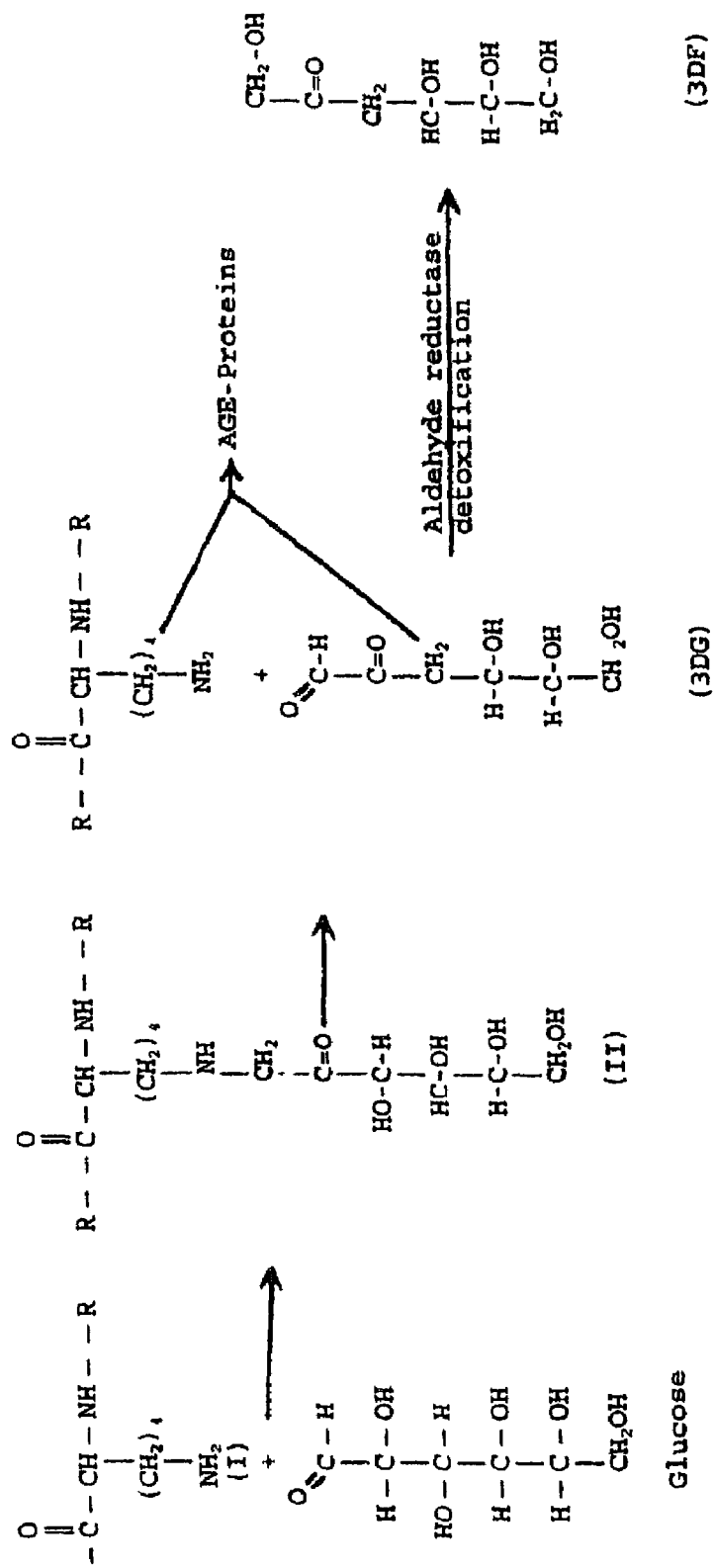
FIG. 1 is a schematic diagram depicting the initial step involved in the multi-step reaction leading to crosslinking of proteins.
Figure 2:
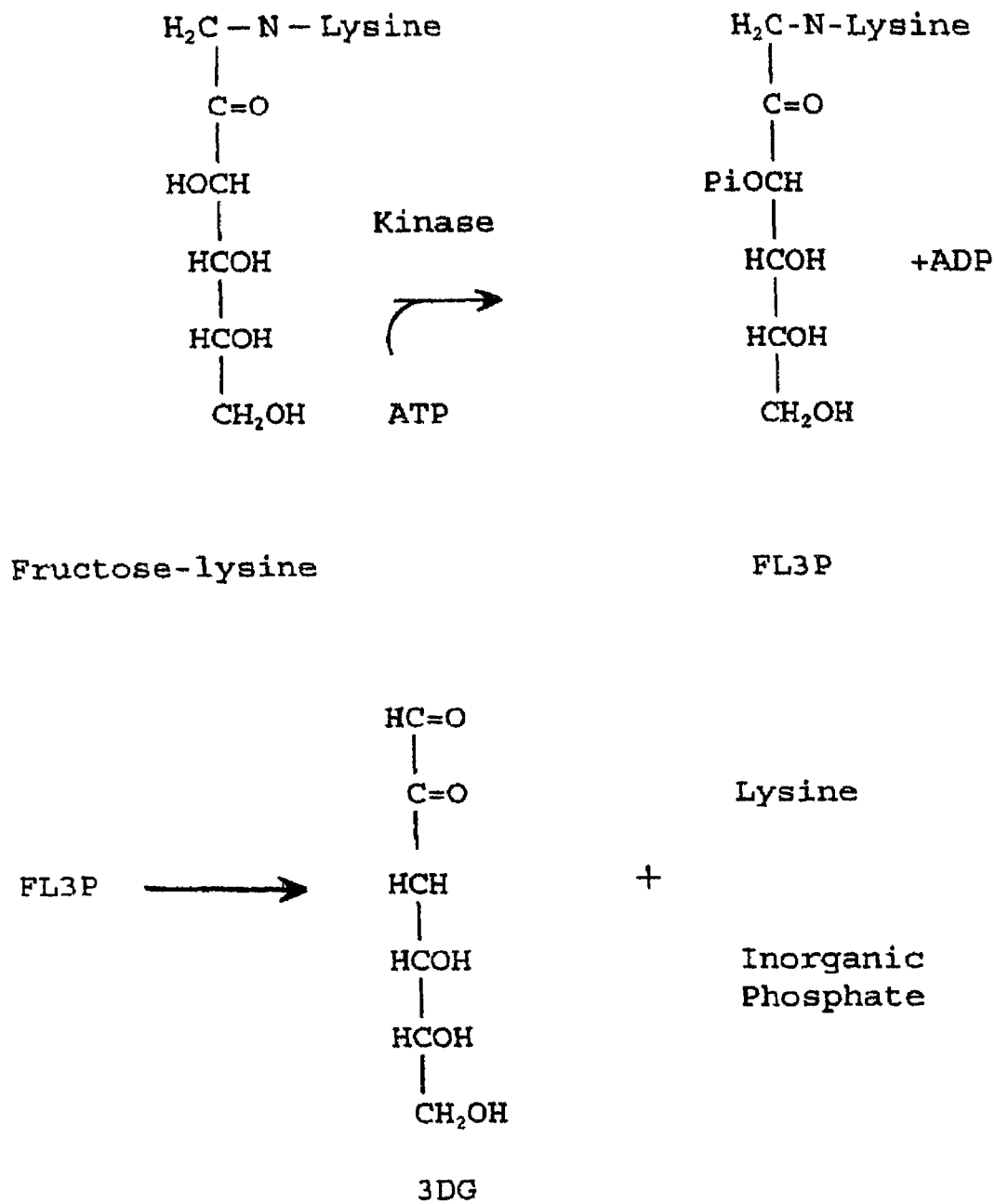
FIG. 2 is a schematic diagram which illustrates the reactions involved in the lysine recovery pathway. Fructose-lysine (FL) is phosphorylated by a fructosamine kinase such as amadorase to form fructoselysine 3-phosphate (FL3P). FL3P spontaneously decomposes into lysine, Pi, and 3DG (Brown et al., U.S. Pat. No. 6,004,958).

"3-Deoxyglucosone" or "3DG," as used herein, refers to the 1,2-dicarbonyl-3-deoxysugar (also known as 3-deoxyhexulosone) which can be formed via an enzymatic pathway or can be formed via a nonenzymatic pathway. For purposes of the present description, the term 3-deoxyglucosone is an alpha-dicarbonyl sugar which can be formed by pathways including the nonenzymatic pathway described in FIG. 1 and the enzymatic pathway resulting in breakdown of FL3P described in FIG. 2. Another source of 3DG is diet. 3DG is a member of the alpha-dicarbonyl sugar family, also known as 2-oxoaldehydes.

A "3DG associated" or "3DG related" disease or disorder as used herein, refers to a disease, condition, or disorder which is caused by or associated with 3DG, including defects related to enhanced synthesis, production, formation, and accumulation of 3DG, as well as those caused by or associated with decreased levels of degradation, detoxification, binding, and clearance of 3DG.

"A 3DG inhibiting amount" or an "alpha-dicarbonyl inhibiting amount" of a compound refers to that amount of compound which is sufficient to inhibit the function or process of interest, such as synthesis, formation or function of 3DG or another alpha-dicarbonyl sugar.

"3-O-methyl sorbitollysine (3-O-Me-sorbitollysine)," is an inhibitor of fructosamine kinases, as described herein. It is used interchangeably with the term "DYN 12".

As used herein, "alleviating a disease or disorder symptom," means reducing the severity of the symptom.

The term "AGE-proteins" (Advanced Glycation End product modified proteins), as used herein, refers to a product of the reaction between sugars and proteins (Brownlee, 1992, Diabetes Care, 15: 1835; Niwa et al., 1995, Nephron, 69: 438). It is clear that the reaction, for example, between protein lysine residues and glucose does not stop with the formation of fructose-lysine (FL). FL can undergo multiple dehydration and rearrangement reactions to produce non-enzymatic 3DG, which reacts again with free amino groups, leading to cross-linking and browning of the protein involved. Indeed, there is reasonable evidence that 3DG, as defined above, is a central intermediate in this modification reaction.

"Amadorase," as used herein, refers to a fructosamine kinase responsible for the production of 3-DG. More specifically it refers to a protein which can enzymatically convert FL to FL3P, as defined above, when additionally supplied with a source of high energy phosphate.

The term "Amadori product," as used herein, refers to a ketoamine such as fructoselysine, which is a rearrangement product forming following glucose interaction with the ε-NH2 groups of lysine-containing proteins.

As used herein, "amino acids" are represented by the full name thereof, by the three-letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The tern "Biological sample," as used herein, refers to samples obtained from a subject, including skin, hair, tissue, blood, plasma, cells, sweat and urine.

The term "clearance," as used herein refers to the physiological process of removing a compound or molecule, such as by diffusion, exfoliation, removal via the bloodstream, and excretion in urine or other vehicles such as sweat.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above, or modified versions or derivatives of the compound.

As used herein, the terms "conservative variation" or "conservative substitution" refer to the replacement of an amino acid residue by another, biologically similar residue. Conservative variations or substitutions are not likely to significantly change the shape of the peptide chain. Examples of conservative variations, or substitutions, include the replacement of one hydrophobic residue such as isoleucine, valine, leucine or alanine for another, or the substitution of one charged amino acid for another, such as the substitution of arginine for lysine, glutamic for aspartic acid, or glutamine for asparagine, and the like.

"Detoxification" of 3DG refers to the breakdown or conversion of 3DG to a form which does not allow it to perform its normal function. Detoxification can be brought about or stimulated by any composition or method, including "pharmacologic detoxification", or metabolic pathway which can cause detoxification of 3DG.

"Pharmacologic detoxification of 3DG" or other alpha-dicarbonyl sugars refers to a process in which a compound binds with or modifies 3DG, which in turn causes it to be become inactive or to be removed by metabolic processes such as excretion.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

An "effective amount" or "therapeutically effective amount" of a compound is that amount of compound which is sufficient to provide a beneficial effect to the subject to which the compound is administered.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "floating," as used herein, refers to bonds of a substituent to a ring structure, such that the substituent can be attached to the ring structure at any available carbon juncture. A "fixed" bond means that a substituent is attached at a specific site.

The term "formation of 3DG" refers to 3DG which is not necessarily formed via a synthetic pathway, but can be formed via a pathway such as spontaneous or induced breakdown of a precursor.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment," as applied to a nucleic acid, can ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

The term "fructose-lysine" (FL) is used herein to signify any glycated-lysine, whether incorporated in a protein/peptide or released from a protein/peptide by proteolytic digestion. This term is specifically not limited to the chemical structure commonly referred to as fructose-lysine, which is reported to form from the reaction of protein lysine residues and glucose. As noted above, lysine amino groups can react with a wide variety of sugars. Indeed, one report indicates that glucose is the least reactive sugar out of a group of sixteen (16) different sugars tested (Bunn et al., Science, 213: 222 (1981)). Thus, tagatose-lysine formed from galactose and lysine, analogously to glucose is included wherever the term fructose-lysine is mentioned in this description, as is the condensation product of all other sugars, whether naturally-occurring or not. It will be understood from the description herein that the reaction between protein-lysine residues and sugars involves multiple reaction steps. The final steps in this reaction sequence involve the crosslinking of proteins and the production of multimeric species, known as AGE-proteins, some of which are fluorescent. Once an AGE protein forms, then proteolytic digestion of such AGE-proteins does not yield lysine covalently linked to a sugar molecule. Thus, these species are not included within the meaning of "fructose-lysine", as that term is used herein.

The term "Fructose-lysine-3-phosphate," as used herein, refers to a compound formed by the enzymatic transfer of a high energy phosphate group from ATP to FL. The term fructose-lysine-3-phosphate (FL3P), as used herein, is meant to include all phosphorylated fructose-lysine moieties that can be enzymatically formed whether free or protein-bound.

"Fructose-lysine-3-phosphate kinase" (FL3K), as used herein, refers to one or more proteins, such as amadorase, which can enzymatically convert FL to FL3P, as described herein, when supplied with a source of high energy phosphate. The term is used interchangeably with "fructose-lysine kinase (FLK)" and with "amadorase".

The term "FL3P Lysine Recovery Pathway," as used herein, refers to a lysine recovery pathway which exists in human skin and kidney, and possibly other tissues, and which regenerates unmodified lysine as a free amino acid or as incorporated in a polypeptide chain.

The term "Glycated Diet," as used herein, refers to any given diet in which a percentage of normal protein is replaced with glycated protein. The expressions "glycated diet" and "glycated protein diet" are used interchangeably herein.

"Glycated lysine residues," as used herein, refers to the modified lysine residue of a stable adduct produced by the reaction of a reducing sugar and a lysine-containing protein. The majority of protein lysine residues are located on the surface of proteins as expected for a positively charged amino acid. Thus, lysine residues on proteins, which come in contact with serum, or other biological fluids, can freely react with sugar molecules in solution. This reaction occurs in multiple stages. The initial stage involves the formation of a Schiff base between the lysine free amino group and the sugar keto-group. This initial product then undergoes the Amadori rearrangement, to produce a stable ketoamine compound.

This series of reactions can occur with various sugars. When the sugar involved is glucose, the initial Schiff base product will involve imine formation between the aldehyde moiety on C-1 of the glucose and the lysine ε-amino group. The Amadori rearrangement will result in formation of lysine coupled to the C-1 carbon of fructose, 1-deoxy-1-(ε-aminolysine)-fructose, herein referred to as fructose-lysine or FL. Similar reactions will occur with other aldose sugars, for example galactose and ribose (Dills, 1993, Am. J. Clin. Nutr. 58:S779). For the purpose of the present invention, the early products of the reaction of any reducing sugar and the ε-amino residue of protein lysine are included within the meaning of glycated-lysine residue, regardless of the exact structure of the modifying sugar molecule.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homologous" or homology" are used synonymously with "identity". The determination of percent identity or homology between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator "www(dot)ncbi(dot)nlm(dot)nih(dot)gov/BLAST/".

BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See "www(dot)ncbi(dot)nlm(dot)nih(dot)gov".

The percent identity between two sequences can be determined using techniques similar to those described above, with or without allowing gaps. In calculating percent identity, typically exact matches are counted. The term "induction of 3DG" or "inducing 3DG," as used herein, refers to methods or means which start or stimulate a pathway or event leading to the synthesis, production, or formation of 3DG or increase in its levels, or stimulate an increase in function of 3DG. Similarly, the phrase "induction of alpha-dicarbonyl sugars", refers to induction of members of the alpha-dicarbonyl sugar family, including 3DG, glyoxal, methyl glyoxal, and glucosone.

"Inhibiting 3DG" as described herein, refers to any method or technique which inhibits 3DG synthesis, production, formation, accumulation, or function, as well as methods of inhibiting the induction or stimulation of synthesis, formation, accumulation, or function of 3DG. It also refers to any metabolic pathway which can regulate 3DG function or induction. The term also refers to any composition or method for inhibiting 3DG function by detoxifying 3DG or causing the clearance of 3DG. Inhibition can be direct or indirect. Induction refers to induction of synthesis of 3DG or to induction of function. Similarly, the phrase "inhibiting alpha-dicarbonyl sugars", refers to inhibiting members of the alpha-dicarbonyl sugar family, including 3DG, glyoxal, methyl glyoxal, and glucosone.

The term "inhibiting accumulation of 3DG," as used herein, refers to the use of any composition or method which decreases synthesis, increases degradation, or increases clearance, of 3DG such that the result is lower levels of 3DG or functional 3DG in the tissue being examined or treated, compared with the levels in tissue not treated with the composition or method. Similarly, the phrase "inhibiting accumulation of alpha-dicarbonyl sugars", refers to inhibiting accumulation of members of the alpha-dicarbonyl sugar family, including 3DG, glyoxal, methyl glyoxal, and glucosone.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound invention or be shipped together with a container which contains the identified compound. Alternatively, the instructional material can be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence. "Modified" compound, as used herein, refers to a modification or derivation of a compound, which may be a chemical modification, such as in chemically altering a compound in order to increase or change its functional ability or activity.

The term "mutagenicity" refers to the ability of a compound to induce or increase the frequency of mutation. The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequences (i.e., A, T, G, C), this also includes an RNA sequence (i.e., A, U, G, C) in which "U" replaces "T."

The term "peptide" typically refers to short polypeptides.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream. "Permeation enhancer" is used interchangeably with "penetration enhancer".

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

A "polynucleotide" means a single strand or parallel and anti-parallel strands of a nucleic acid. Thus, a polynucleotide may be either a single-stranded or a double-stranded nucleic acid.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

The term "protein" typically refers to large polypeptides.

"Removing 3-deoxyglucosone," as used herein, refers to any composition or method, the use of which results in lower levels of 3-deoxyglucosone (3DG) or lower levels of functional 3DG. Lower levels of 3DG could result from decreased synthesis or formation, increased degradation, increased clearance, or a combination of the three. Lower levels of functional 3DG could result from modifying the 3DG molecule such that it can no longer function in the process of glycation or could result from binding with another molecule which blocks its ability to function. Lower levels of 3DG can also result from increased clearance and excretion in urine. The term is also used interchangeably with inhibiting accumulation of 3DG. Similarly, the phrase "removing alpha-dicarbonyl sugars", refers to removal of members of the alpha-dicarbonyl sugar family, including 3DG, glyoxal, methyl glyoxal, and glucosone.

Also, the terms glycated-lysine residue, glycated protein and glycosylated protein or lysine residue are used interchangeably herein, which is consistent with current usage in scientific journals where such expressions are often used interchangeably.

The term "skin," as used herein, refers to the commonly used definition of skin, e.g., the epidermis and dermis, and the cells, glands, and connective tissue which comprise the skin.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "susceptible test animal," as used herein, refers to a strain of laboratory animals which, due to the presence of certain genetic mutations, have a higher propensity toward a property of choice, such as diabetes, cancer, etc.

"Synthesis of 3DG", as used herein refers to the formation or production of 3DG. 3DG can be formed based on an enzyme dependent pathway or a non-enzyme dependent pathway. Similarly, the phrase "synthesis of alpha-dicarbonyl sugars", refers to synthesis or spontaneous formation of members of the alpha-dicarbonyl sugar family, including 3DG, glyoxal, methyl glyoxal, and glucosone.

"Synthetic peptides or polypeptides" mean a non-naturally occurring peptide or polypeptide. Synthetic peptides or polypeptides can be synthesized, for example, using an automated polypeptide synthesizer. Those of skill in the art know of various solid phase peptide synthesis methods.

A "therapeutic" treatment is a treatment administered to a subject who exhibits signs of pathology, for the purpose of diminishing or eliminating those signs.

By "transdermal" delivery is intended both transdermal (or "percutaneous") and transmucosal administration, i.e., delivery by passage of a drug through the skin or mucosal tissue and into the bloodstream. Transdermal also refers to the skin as a portal for the administration of drugs or compounds by topical application of the drug or compound thereto.

The term "topical application", as used herein, refers to administration to a surface, such as the skin. This term is used interchangeably with "cutaneous application".

The term to "treat," as used herein, means reducing the frequency with which symptoms are experienced by a patient or subject or administering an agent or compound to reduce the frequency with which symptoms are experienced.

As used herein, "treating a disease or disorder" means reducing the frequency with which a symptom of the disease or disorder is experienced by a patient. Disease and disorder are used interchangeably herein.

As used herein, the term "wild-type" refers to the genotype and phenotype that is characteristic of most of the members of a species occurring naturally and contrasting with the genotype and phenotype of a mutant.

Methods of Inhibiting Synthesis, Formation, and Accumulation of 3DG and Other Alpha-dicarbonyl Sugars in Skin It has been discovered in the present invention that an enzyme which is involved in the enzymatic synthetic pathway of 3DG production is present at high levels in skin (see Example 20). Furthermore, it has also been discovered in the present invention that 3DG is present at high levels in skin (see Example 19). Accordingly, the invention includes compositions and methods which interfere with both enzymatic and nonenzymatic based synthesis or formation of 3DG in skin, and which also interfere with the function of 3DG in skin. 3DG is a member of a family of compounds called alpha-dicarbonyl sugars. Other members of the family include glyoxal, methyl glyoxal, and glucosone. The present invention also relates to compositions and methods for inhibiting accumulation of 3DG and other alpha-dicarbonyl sugars in skin and for inhibiting 3DG dependent or associated skin wrinkling, skin aging, or other skin diseases or disorders, as well as skin wrinkling, skin aging, or other skin diseases and disorders associated with other alpha-dicarbonyl sugars. The invention also includes inhibiting accumulation of 3DG in skin using compositions and methods for stimulating the pathways, or components of the pathways, leading to 3DG detoxification, degradation, or clearance from the skin.

It should be noted that 3DG is a member of the alpha-dicarbonyl sugar family of molecules. It should also be noted that other members of the alpha-dicarbonyl sugar family can perform functions similar to 3DG, as described herein, and that like 3DG functions, the functions of other members of the alpha-dicarbonyl sugar family are inhibitable as well. Thus, the invention should be construed to include methods of inhibiting synthesis, formation, and accumulation of other alpha-dicarbonyl sugars as well.

Inhibition of 3DG synthesis, formation, and accumulation in skin can be direct or indirect. For example, direct inhibition of 3DG synthesis refers to blocking an event that occurs immediately prior to or upstream in a pathway of 3DG synthesis or formation, such as blocking amadorase or the conversion of fructose-lysine-3-phosphate (FL3P) to 3DG, lysine, and inorganic phosphate. Indirect inhibition can include blocking or inhibiting upstream precursors, enzymes, or pathways, which lead to the synthesis of 3DG. Components of an upstream pathway, for example, include the amadorase gene and amadorase mRNA. The invention should not be construed to include inhibition of only the enzymatic and nonenzymatic pathways described herein, but should be construed to include methods of inhibiting other enzymatic and nonenzymatic pathways of 3DG synthesis, formation and accumulation in skin as well. The invention should also be construed to include the other members of the alpha-dicarbonyl sugar family, including glyoxal, methyl glyoxal, and glucosone where applicable.

Various assays described herein may be used to directly measure 3DG synthesis or levels of 3DG, or assays may be used which are correlative of 3DG synthesis or levels, such as measurement of its breakdown product, 3DF.

The present invention includes novel methods for the inhibition of 3DG synthesis in skin. Preferably, the skin is mammalian skin, and more preferably, the mammal skin is human skin.

In one aspect, the inhibitor inhibits an enzyme involved in the synthesis of 3DG. In one embodiment the enzyme is a fructosamine kinase. In yet another embodiment the fructosamine kinase is amadorase, as disclosed in U.S. Pat. No. 6,004,958.

In yet another aspect of the invention the inhibitor inhibits the nonenzymatic synthesis and formation of 3DG in the skin.

In one embodiment of the invention, the inhibitor inhibits the accumulation of 3DG in the skin. In one aspect, the 3DG is synthesized or formed in the skin. However, the inhibitor can also inhibit accumulation of 3DG in the skin, where the source of 3DG is other than the skin. In one aspect, the source of the 3DG is dietary, i.e., it is derived from an external source rather than an internal source, and then accumulates in the skin. Thus, this aspect of the invention includes the inhibition of 3DG synthesis or formation in the skin and/or inhibition of accumulation of 3DG in the skin. In the latter case, the source of 3DG may be enzymatic synthesis of 3DG directly in the skin, enzymatic synthesis of 3DG in a tissue other than skin, nonenzymatic synthesis or formation of 3DG in the skin or in a non-skin tissue, or the source of the 3DG may be external, such as, for example, dietary. The methods to be used for inhibiting accumulation of 3DG or other alpha-dicarbonyl sugars via any one of these pathways are more fully described elsewhere herein.

Methods of Removing 3DG from Skin

The present invention also relates to compositions and methods for removing 3DG and other alpha-dicarbonyl sugars from skin and for inhibiting 3DG dependent or associated skin wrinkling, skin aging, or other skin diseases or disorders, as well as skin wrinkling, skin aging, or other skin diseases and disorders associated with other alpha-dicarbonyl sugars. To this end, the invention includes compositions and methods for inhibiting the production, synthesis, formation, and accumulation of 3DG in skin. The invention also includes compositions and methods for stimulating the pathways, or components of the pathways, leading to 3DG detoxification, degradation, or clearance from the skin.

Using Antibodies to Inhibit 3DG Synthesis

In one aspect of the invention, the inhibitor of a fructosamine kinase is an antibody. The antibody can be an antibody that is known in the art or it can be an antibody prepared using known techniques and the published sequence of the fructosamine kinase/amadorase (Accession No. NP_071441). The antibody may also be one which is prepared against any of the precursors of 3DG or against molecules which regulate 3DG synthesis upstream from fructosamine kinase or the precursors of 3DG.

In one aspect, the antibody is selected from the group consisting of a polyclonal antibody, a monoclonal antibody, a humanized antibody, a chimeric antibody, and a synthetic antibody.

The invention includes a method by which an antibody inhibitor can be generated and used as an inhibitor of 3DG synthesis or function. Antibodies can be prepared against a fructosamine kinase or other proteins of the enzymatic pathway of 3DG synthesis or against other molecules which are part of the pathway, including precursors of 3DG. The preparation and use of antibodies to inhibit protein synthesis or function or to inhibit other molecules or their synthesis is well known to those skilled in the art, and is described for example in Harlow et al. (Harlow et al., 1988, *Antibodies: A Laboratory Manual,* Cold Spring Harbor, N.Y.; Harlow et al., 1999, Using Antibodies: A Laboratory Manual, Cold Spring Harbor Laboratory Press, NY). Antibodies of the invention can also be used to detect proteins or other molecules which may be components of the 3DG pathway.

The generation of polyclonal antibodies is accomplished by inoculating the desired animal with the antigen and isolating antibodies which specifically bind the antigen therefrom.

Monoclonal antibodies can be used effectively intracellularly to avoid uptake problems by cloning the gene and then transfecting the gene encoding the antibody. Such a nucleic acid encoding the monoclonal antibody gene obtained using the procedures described herein may be cloned and sequenced using technology which is available in the art.

Monoclonal antibodies directed against full length or peptide fragments of a protein or peptide may be prepared using any well known monoclonal antibody preparation procedure. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide or other molecules are generated from mice immunized with the peptide using standard procedures as referenced herein. A nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the existing technology described in, for example, Wright et al., id., and in the references cited therein, and in Gu et al. (1997, Thrombosis and Hematocyst 77:755-759), and other methods of humanizing antibodies well-known in the art or to be developed. Techniques are also well known in the art which allow such an antibody to be modified to remain in the cell. The invention encompasses administering a nucleic acid encoding the antibody, wherein the molecule further comprises an intracellular retention sequence. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11-17).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In one embodiment, the antibodies are made against amadorase (SEQ ID NO:2), or against derivatives or fragments thereof. In another embodiment, the antibody is made against 3DG. In another aspect of the invention, antibodies can be made against other components of the 3DG pathway. Such an antibody may be prepared to bind and inhibit function of its cognate antigen. In another embodiment, the antibodies will be made against the other members of the alpha-dicarbonyl sugar family of molecules.

Inhibiting 3DG Synthesis, Production, Accumulation and Function by Inhibiting Fructosamine Kinase Function Using Antisense Techniques In one embodiment, antisense nucleic acids complementary to fructosamine kinase mRNA can be used to block the expression or translation of the corresponding mRNA (see SEQ ID NO:1) (see Examples 20 and 22). Antisense oligonucleotides as well as expression vectors comprising antisense nucleic acids complementary to nucleic acids encoding a fructosamine kinase such as amadorase can be prepared and used based on techniques routinely performed by those of skill in the art, and described, for example, in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. (eds., 1994, Methods for General and Molecular Bacteriology, American Society for Microbiology, Washington, D.C.). The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497). Oligonucleotides which contain at least one phosphorothioate modification are known to confer upon the oligonucleotide enhanced resistance to nucleases. Specific examples of modified oligonucleotides include those which contain phosphorothioate, phosphotriester, methyl phosphonate, short chain alkyl or cycloalkyl intersugar linkages, or short chain heteroatomic or heterocyclic intersugar ("backbone") linkages. In addition, oligonucleotides having morpholino backbone structures (U.S. Pat. No. 5,034,506) or polyamide backbone structures (Nielsen et al., 1991, Science 254: 1497) may also be used.

The examples of oligonucleotide modifications described herein are not exhaustive and it is understood that the invention includes additional modifications of the antisense oligonucleotides of the invention which modifications serve to enhance the therapeutic properties of the antisense oligonucleotide without appreciable alteration of the basic sequence of the antisense oligonucleotide.

Phosphorothioate oligonucleotides, which have very low sensitivity to nuclease degradation, may be used. Some oligonucleotides may be prepared lacking CG motifs, which should help reduce toxicity for in vivo use.

In another aspect, antisense nucleic acids complementary to fructosamine kinase mRNAs, such as amadorase mRNAs, can be used to block fructosamine kinase function, and subsequently 3DG synthesis and function, by inhibiting translation of a fructosamine kinase mRNA. This can be done by transfecting an appropriate antisense sequence. Fructosamine kinase genes have been sequenced and based on these data, antisense nucleic acids may be readily prepared using techniques known to those skilled in the art.

The antisense oligonucleotide inhibitors of fructosamine kinase may be used independently in the cell culture systems essentially as described herein (see Examples 20-22) or administered to animals. In one embodiment of the invention, the inhibitor of fructosamine kinase is an oligonucleotide, preferably from 5 to 25 nucleotides in length. In another embodiment, the oligonucleotide is from 25 to 50 nucleotides in length. In yet another embodiment, the oligonucleotide is from 50 to 100 nucleotides in length. In a further embodiment, the oligonucleotide is 100-400 nucleotides in length.

Phosphorothioate oligonucleotides enter cells readily without the need for transfection or electroporation, which avoids subjecting the cells to nonspecific inducers of a stress response that might confound the experiment. The oligonucleotides may be administered using several techniques known to those of skill in the art and described herein. Effective inhibitory concentrations for phosphorothioates range between 1 and 50 μM, so a titration curve for diminution of fructosamine kinase signal in western blots can be done to establish effective concentrations for each oligonucleotide used. Once inside the cells, the phosphorothioate-oligonucleotides hybridize with the nascent mRNA very close to the transcriptional start site, a site having maximum effect for antisense oligonucleotide inhibition.

The ability to selectively inhibit transcription of fructosamine kinase or other genes with specific antisense molecules is expected to also allow the inhibition of induction of increased fructosamine kinase synthesis or other proteins involved in the synthesis or induction of 3DG in skin diseases or disorders. Thus, the invention provides methods for the use of antisense oligonucleotides that will be effective at diminishing steady-state levels of the protein of interest. Furthermore, inhibition of fructosamine kinase or other important proteins will reduce steady-state synthesis of proteins involved in the synthesis, production, accumulation, or function of 3DG. The invention should be construed to include other members of the alpha-dicarbonyl sugar family of molecules as well, and not just 3DG.

The invention should not be construed to include only fructosamine kinase inhibition using antisense techniques, but should also be construed to include inhibition of other genes and their proteins which are involved in a 3DG synthetic pathway. Furthermore, the invention should not be construed to include only these particular antisense methods described herein.

Using Compounds to Inhibit 3DG Synthesis

In one embodiment the invention includes a method of inhibiting 3DG synthesis in the skin of a mammal, said method comprising administering to a mammal an effective amount of an inhibitor of 3DG synthesis, or a derivative or modification thereof, thereby inhibiting 3DG synthesis in the skin of a mammal. Preferably, the mammal is a human.

In one embodiment, the inhibitor comprises from about 0.0001% to about 15% by weight of the pharmaceutical composition. In one aspect, the inhibitor is administered as a controlled-release formulation. In another aspect the pharmaceutical composition comprises a lotion, a cream, a gel, a liniment, an ointment, a paste, a toothpaste, a mouthwash, an oral rinse, a coating, a solution, a powder, and a suspension. In yet another aspect, the composition further comprises a moisturizer, a humectant, a demulcent, oil, water, an emulsifier, a thickener, a thinner, a surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

The invention should be construed to include various methods of administration, including topical, oral, intramuscular, and intravenous.

In one aspect of the invention, the inhibitor of 3DG synthesis is an inhibitor of fructosamine kinase/amadorase. The inhibitor of fructosamine kinase can be a compound such as those of the formula (Formula XIX):

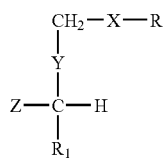

XIX wherein X is $-NR'-$, $-S(O)-$, $-S(O)_2-$, or $-O-$, R' being selected from the group consisting of H, and linear or branched chain alkyl group ($C_1$-$C_4$) and an unsubstituted or substituted aryl group ($C_6$-$C_{10}$) or aralkyl group ($C_7$-$C_{10}$) or $CH_2(CHOR_2)_nCH_2OR_2$ with n=1-5 or $CH(CH_2OR_2)(CHOR_2)_nCH_2OR_2$ with n=1-4 where $R_2$ is H, alkyl ($C_1$-$C_4$) or an unsubstituted or substituted aryl group ($C_6$-$C_{10}$) or araalkyl group ($C_7$-$C_{10}$); R is a substituent selected from the group consisting of H, an amino acid residue, a polyaminoacid residue, a peptide chain, a linear or branched chain aliphatic group ($C_1$-$C_8$), which is unsubstituted or substituted with at least one nitrogen- or oxygen-containing substituent, a linear or branched chain aliphatic group ($C_1$-$C_8$), which is unsubstituted or substituted with at least one nitrogen- or oxygen-containing substituent and interrupted by at least one $-O-$, $-NH-$, or $-NR_3-$ moiety, $R_3$ being linear or branched chain alkyl group ($C_1$-$C_6$) and an unsubstituted or substituted aryl group ($C_6$-$C_{10}$) or aralkyl group ($C_7$-$C_{10}$), with the proviso that when X represents $-NR_1-$, R and $R_1$, together with the nitrogen atom to which they are attached, may also represent a substituted or unsubstituted heterocyclic ring having from 5 to 7 ring atoms, with at least one of nitrogen and oxygen being the only heteroatoms in said ring, said aryl group ($C_6$-$C_{10}$) or aralkyl group ($C_7$-$C_{10}$) and said heterocyclic ring substituents being selected from the group consisting of H, alkyl ($C_1$-$C_6$), halogen, $CF_3$, CN, $NO_2$ and $-O$-alkyl ($C_1$-$C_6$).

Other appropriate reactants include without limitation unsubstituted or substituted aryl ($C_6$-$C_{10}$) compounds, wherein the substituent may be alkyl ($C_1$-$C_3$), alkoxy, carboxy, nitro or halogen groups, unsubstituted or substituted alkanes, wherein the substituent may be at least one alkoxy group; or unsubstituted or substituted nitrogen-containing heterocyclic compounds, wherein the substituents may be alkyl ($C_1$-$C_3$), aryl ($C_6$-$C_{10}$), alkoxy, carboxy, nitro or halogen groups. Illustrative examples of the last-mentioned group of reactants include m-methyl-, p-methyl-, m-methoxy-, o-methoxy- and m-nitro-aminobenzenes, o- and p-aminobenzoic acids; n-propylamine, n-butylamine, 3-methoxypropylamine; morpholine and piperdine.

In one aspect of the invention, representative inhibitor compounds having the above formula include galactitol lysine, 3-deoxy sorbitol lysine, 3-deoxy-3-fluoro-xylitol lysine, and 3-deoxy-3-cyano sorbitol lysine and 3-O-methyl sorbitollysine. Examples of known compounds that may be used as inhibitors in practicing this invention include, without limitation, meglumine, sorbitol lysine, galactitol lysine, and mannitol lysine. A preferred inhibitor is 3-O-methyl sorbitol-lysine.

The compounds of the invention may be administered to, for example, a cell, a tissue, or a subject by any of several methods described herein and by others which are known to those of skill in the art.

The invention should not be construed to include only the modifications, derivatives, or substitutions of Formula XIX and the representative compounds described herein. The invention should also be construed to include other modifications not described herein, as well as compounds not described herein which are representative of Formula XIX.

In one aspect, an inhibitor of the invention which inhibits enzymatic synthesis of 3DG may be synthesized in vitro using techniques known in the art (see Example 8).

Compounds and Methods Useful for Inhibiting 3DG Function

Figure 12:
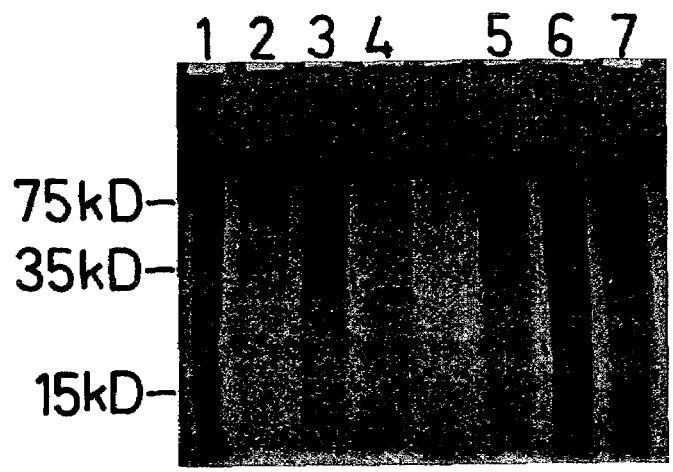
FIG. 12 is an image of a polyacrylamide gel demonstrating the effects of 3DG on collagen crosslinking and the inhibition of 3DG induced crosslinking by arginine. Collagen type I was treated with 3DG in the presence or absence of arginine. The samples were subjected to cyanogen bromide (CNBr) digestion, electrophoresed on a 16.5% SDS Tris-tricine gel, and then the gels were processed using silver stain techniques to visualize the proteins. Lane 1 contains molecular weight marker standards. Lanes 2 and 5 contain 10 and 20 µl of the collagen mixture following CNBr digestion. Lanes 3 and 6 contain the collagen mixture treated with 3DG and then digested with CNBr, and loaded at 10 and 20 µl, respectively. Lanes 4 and 7 contain the mixture of collagen incubated with 5 mM 3DG and 10 mM arginine and then digested with CNBr, and loaded at 10 and 20 µl, respectively.

The invention, as disclosed herein, relates to the involvement of 3DG in causing various skin diseases and disorders and to methods of inhibiting the function of 3DG in order to alleviate or treat 3DG associated skin diseases and disorders. The invention also relates to the involvement of 3DG in other diseases and disorders, such as gum diseases and disorders. Such gingival diseases and disorders include, but are not limited to, gingivitis, receding gums, and other 3DG or other alpha-dicarbonyl sugar associated gingival diseases and disorders. As described above, inhibition of 3DG function can be direct or indirect. Therefore, 3DG function may be inhibited or caused to decrease using many approaches as described herein. Inhibition of 3DG function may be assayed or monitored using techniques described herein as well as others known to those of skill in the art. Function can be measured directly or it can be estimated using techniques to measure parameters which are known to be correlative of 3DG function. For example, protein crosslinking and protein production can be measured directly using techniques such as electrophoretic analysis (see FIG. 12 and Examples 7 and 18) as well as other techniques (see Examples 21-24). The invention should be construed to include not only compounds useful for preventing 3DG induced crosslinking of molecules such as collagen, elastin, and proteoglycans, but it should also be construed to include compounds which inhibit crosslinking of other molecules as well. The invention should also be construed to include the use of compounds to modulate other 3DG functions as well, such as apoptosis and formation of reactive oxygen species. It is known that in macrophage-derived cells apoptotic cell death can be induced by methylglyoxal and 3DG (Okado et al., 1996, Biochem. Biophys. Res. Commun. 225:219-224). In yet another aspect of the invention, an inhibitor of 3DG inhibits an active oxygen species (Vander Jagt et al., 1997, Biochem. Pharmacol. 53:1133-1140). The invention should be construed to include other alpha-dicarbonyl sugars as well. 3DG and its detoxification product 3DF can be measured several ways using cell, tissue, blood, plasma, and urine samples (see Examples 4, 5, 6, 14, 15, and 17) and FL, a product produced during the synthesis of 3DG, can also be measured (see Examples 5), as can a precursor, FL3P (see FIGS. 1 and 2 and Examples 1, 2, and 3).

The invention discloses methods which are useful for inhibiting 3DG function in the skin. Such a method includes administering an effective amount of one or more inhibitors of 3DG function, or modifications or derivatives thereof, in a pharmaceutical composition to a subject.

In one aspect of the invention the 3DG function inhibitor inhibits protein crosslinking. In another aspect, the inhibitor inhibits formation of advanced glycation end product modified proteins. In yet another aspect, the 3DG function inhibitor comprises a structure of one of structural formulas I-XIX or is arginine or a derivative or modification thereof.

In one embodiment, the inhibitor comprises from about 0.0001% to about 15% by weight of the pharmaceutical composition. In one aspect, the inhibitor is administered as a controlled-release formulation. In another aspect the pharmaceutical composition comprises a lotion, a cream, a gel, a liniment, an ointment, a paste, a toothpaste, a mouthwash, an oral rinse, a coating, a solution, a powder, and a suspension. In yet another aspect, the composition further comprises a moisturizer, a humectant, a demulcent, oil, water, an emulsifier, a thickener, a thinner, a surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

The invention should be construed to include various methods of administration, including topical, oral, intramuscular, and intravenous.

By way of example, an inhibitor of 3DG function may be an isolated nucleic acid encoding a nucleic acid which is complementary to a fructosamine kinase mRNA and in an antisense orientation. Other inhibitors include an antisense oligonucleotide, an antibody, or other compounds or agents such as small molecules.

It should be understood that compositions and methods for inhibiting pathways, events, and precursors leading to the synthesis or production of 3DG, may inhibit not only 3DG synthesis, but also its accumulation, and ultimately its function. The invention should be construed to include compositions and methods to inhibit all pathways and precursors leading to 3DG synthesis (see FIGS. 1 and 2).

In another embodiment of the invention, the disclosure provides methods for directly inhibiting function of 3DG which is associated with various skin diseases and disorders. In one aspect, the method of inhibiting 3DG function in skin includes inhibiting 3DG with compounds such as those comprising structural formulas I-XVIII described herein. Compounds comprising these formulas can bind to 3DG and/or inhibits its function, as described herein. In addition, the invention includes other molecules which can bind to and block 3DG function, such as antibodies.

The method of the invention includes use of the following compounds, as illustrated by their structural formulas, to inhibit or block 3DG function.

Compounds which may be used in the practice of this invention include one or more (i.e., combinations) of the following:

Formula I comprises a structure wherein $R_1$ and $R_2$ are independently hydrogen, lower alkyl, lower alkoxy or an aryl group, or together with the nitrogen atom form a heterocyclic ring containing from 1 to 2 heteroatoms and 2 to 6 carbon atoms, the second of said heteroatoms being selected from the group consisting of nitrogen, oxygen and sulfur, and includes their biocompatible and pharmaceutically acceptable acid addition salts.

The lower alkyl groups in the compounds of Formula (I) contain 1-6 carbon atoms and include methyl, ethyl, propyl, butyl, pentyl, hexyl, and the corresponding branched chain isomers thereof The lower alkoxy groups have 1-6 carbon atoms and include methoxy, ethoxy, propoxy, butoxy, penthyloxy, and hexyloxy and branched chain isomers thereof. The aryl groups include both substituted and unsubstituted phenyl and pyridyl groups. Typical aryl group substituents are those such as lower alkyl groups, fluoro, chloro, bromo, and iodo atoms.

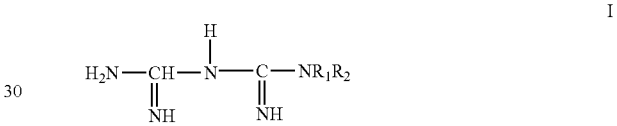

I

Of the compounds encompassed by Formula I, certain combinations of substituents are preferred. For instance, when $R_1$ is a hydrogen atom, then $R_2$ is preferably hydrogen or an aryl group.

When $R_1$ and $R_2$ are both alkyl groups, then the compounds having identical $R_1$ and $R_2$ alkyl groups are preferable.

When $R_1$ and $R_2$ together with the nitrogen atom form a heterocyclic ring containing from 1 to 2 heteroatoms, said heteroatoms being selected from the group consisting of nitrogen, oxygen and sulfur, the preferred heterocyclic rings will be morpholino, piperazinyl, piperidinyl and thiomorpholino, with the morpholino being most preferred.

Representative of the compounds of formula (I) are:
N,N-dimethylimidodicarbonimidic diamide; imidodicarbonimidic diamide;
N-phenylimidodicarbonimidic diamide;
N-(aminoiminomethyl)-4-morpholinecarboximidamide;
N-(aminoiminomethyl)-4-thiomorpholinecarboximidamide;
N-(aminoiminomethyl)-4-methyl-1-piperazinecarboximidamide;
N-(aminoiminomethyl)-1-piperidinecarboximidamide;
N-(aminoiminomethyl)-1-pyrrolidinecarboximidamide;
N-(aminoiminomethyl)-1-hexahydroazepinecarboximidamide;(aminominomethyl)-1-hexahydroazepinecarboximidamide
N-4-pyridylimidodicarbonimidic diamide;
N,N-di-n-hexylimidodicarbonimidic diamide;
N,N-di-n-pentylimidodicarbonimidic diamide;
N,N-d-n-butylimidodicarbonimidic diamide;
N,N-dipropylimidodicarbonimidic diamide;
N,N-diethylimidodicarbonimidic diamide; and the pharmaceutically acceptable acid addition salts thereof.

Formula II comprises a structure wherein Z is N or CH—; X, Y and Q are each independently a hydrogen, amino, heterocyclo, amino lower alkyl, lower alkyl or hydroxy group, and $R_3$ is hydrogen or an amino group, their corresponding 3-oxides, and includes their biocompatible and pharmaceutically acceptable salts.

The compounds of Formula II, wherein the X, Y or Q substituent is on a nitrogen of the ring, exist as tautomers, i.e., 2-hydroxypyrimidine can exist also as 2 (1H)-pyrimidine. Both forms may be used in practicing this invention.

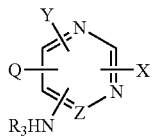

II

The lower alkyl groups of the compounds of formula II contain 1-6 carbon atoms and include methyl, ethyl, propyl, butyl, pentyl, hexyl, and the corresponding branched chain isomers thereof. The heterocyclic groups of the compounds of formula II contain from 3-6 carbon atoms and are exemplified by groups such as pyrrolidinyl, -methylpyrrolidinyl, piperidinol, 2-methylpiperidino morpholino, and hexamethyleneamino.

The "floating" X, Y, Q and $NHR_3$ bonds in Formula II indicate that these variants can be attached to the ring structure at any available carbon juncture. The hydroxy variant of X, Y and Q can also be present on a nitrogen atom.

Of the compounds encompassed by Formula II, certain combinations of substituents are preferred. For instance, compounds having $R_3$ as hydrogen, as a CH group, and at least one of X, Y or Q as another amino group, are preferred. The group of compounds where $R_3$ is hydrogen, Z is a CH group and one of X or Y is an amino lower alkyl group are also preferred. Another preferred group of compounds is those where R is hydrogen and Z is N (nitrogen). Certain substitution patterns are preferred, i.e., the 6-position (IUPAC numbering, Z. dbd. CH) is preferably substituted, and most preferably by an amino or a nitro containing group. Also preferred are compounds where two or more of X, Y and Q are other than hydrogen.

Representative of the compounds of formula II are:

4,5-diaminopyrimidine; 4-amino-5-aminomethyl-2-methylpyrimidine; 6-(piperidino)-2,4-diaminopyrimidine 3-oxide; 4,6-diaminopyrimidine; 4,5,6-triaminopyrimidine; 4,5-diamino-6-hydroxy pyrimidine; 2,4,5-triamino-6-hydroxypyrimidine; 2,4,6-triaminopyrimidine; 4,5-diamino-2-methylpyrimidine; 4,5-diamino-2,6-dimethylpyrimidine; 4,5-diamino-2-hydroxy-pyrimidine; and 4,5-diamino-2-hydroxy-6-methylpyrimidine.

Formula III comprises a structure wherein $R_4$ is hydrogen or acyl, $R_5$ is hydrogen or lower alkyl, Xa is a substituent selected from the group consisting of lower alkyl, carboxy, carboxymethyl, or a phenyl or pyridyl group, optionally substituted by halogen, lower alkyl, hydroxy lower alkyl, hydroxy, or acetylamino with the proviso that when X is a phenyl or pyridyl group, optionally substituted, then $R_5$ is hydrogen and includes their biocompatible and pharmaceutically acceptable acid addition salts.

The lower alkyl groups in the compounds of Formula III contain 1-6 carbon atoms and include methyl, ethyl, propyl, butyl, pentyl, hexyl, and the corresponding branched chain isomers thereof. The halo variants can be fluoro, chloro, bromo, or iodo substituents.

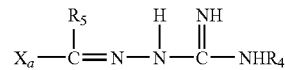

III

Equivalent to the compounds of Formula III for the purpose of this invention are the biocompatible and pharmaceutically acceptable salts thereof.

Such salts can be derived from a variety of organic and inorganic acids including but not limited to methanesulfonic, hydrochloric, toluenesulfonic, sulfuric, maleic, acetic and phosphoric acids.

Of the compounds encompassed by Formula III, certain substituents are preferred. For instance, $R_4$ is preferably a methyl group and Xa is preferably a phenyl or substituted phenyl group.

Representative of the compounds of Formula III are:

N-acetyl-2-(phenylmethylene)hydrazinecarboximidamide; 2-(phenylmethylene)hydrazinecarboximidamide; 2-(2,6-dichlorophenylmethylene) hydrazinecarboximidamide pyridoxal guanylhydrazone; pyridoxal phosphate guanylhydrazone; 2-(1-methylethylidene)hydrazinecarboximidamide; pyruvic acid guanylhydrazone; 4-acetamidobenzaldehyde guanylhydrazone; 4-acetamidobenzaldehyde N-acetylguanylhydrazone; acetoacetic acid guanylhydrazone; and the biocompatible and pharmaceutically acceptable salts thereof.

Formula IV comprises a structure wherein $R_6$ is hydrogen or a lower alkyl group, or a phenyl group, optionally substituted by 1-3 halo, amino, hydroxy or lower alkyl groups, $R_7$ is hydrogen, a lower alkyl group, or an amino group and $R_8$ is hydrogen or a lower alkyl group and includes their biocompatible and pharmaceutically acceptable acid addition salts.

The lower alkyl groups in the compounds of Formula IV contain 1-6 carbon atoms and include methyl, ethyl, propyl, butyl, pentyl, hexyl, and the corresponding branched chain isomers thereof. The halo variants can be fluoro, chloro, bromo, or iodo substituents. Where the phenyl ring is substituted, the point or points of substitution may be ortho meta or para to the point of attachment of the phenyl ring to the straight chain of the molecule.

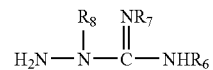

IV

Representative of the compounds of Formula IV are: equival n-butanehydrazonic acid hydrazide; 4-methylbenzamidrazone; N-methylbenzenecarboximidic acid hydrazide; benzenecarboximidic acid 1-methylhydrazide; 3-chlorobenzamidrazone; 4-chlorobenzamidrazone; 2-fluorobenzamidrazone; 3-fluorobenzamidrazone; 4-fluorobenzamidrazone; 2-hydroxybenzamidrazone; 3-hydroxybenzamidrazone, 4-hydroxybenzamidrazone: 2-aminobenzamidrazone; benzenecarbohydrazonic acid hydrazide; benzenecarbohydrazonic acid 1-methylhydrazide; and the biocompatible and pharmaceutically acceptable salts thereof.

Formula V comprises a structure wherein $R_9$ and $R_{10}$ are independently hydrogen, hydroxy, lower alkyl or lower alkoxy, with the proviso that the "floating" amino group is adjacent to the fixed amino group, and includes their biocompatible and pharmaceutically acceptable acid addition salts.

The lower alkyl groups of the compounds of Formula V contain 1-6 carbon atoms and include methyl, ethyl, propyl, butyl, pentyl, hexyl, and the corresponding branched chain isomers thereof. Likewise, the lower alkoxy groups of the compounds of formula V contain 1-6 carbon atoms and include methoxy, ethoxy, propoxy, butoxy pentoxy, hexoxy, and the corresponding branched chain isomers thereof.

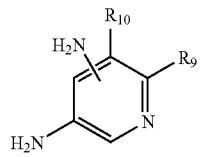

V

Equivalent to the compounds of Formula V for the purpose of this invention are the biocompatible and pharmaceutically acceptable salts thereof.

Such salts can be derived from a variety of organic and inorganic acids including but not limited to methanesulfonic, hydrochloric, toluenesulfonic, sulfuric, maleic, acetic and phosphoric acids.

Of the compounds encompassed by Formula V, certain substituents are preferred. For instance, when $R_9$ is hydrogen then $R_{10}$ is preferably also hydrogen.

Representative of the compounds of Formula V are: 3,4-diaminopyridine; 2,3-diaminopyridine; 5-methyl-2,3-diaminopyridine; 4-methyl-2,3-diaminopyridine; 6-methyl-2,3-pyridinediamine; 4,6-dimethyl-2,3-pyridinediamine; 6-hydroxy-2,3-diaminopyridine; 6-ethoxy-2,3-diaminopyridine; 6-dimethylamino-2,3-diaminopyridine; diethyl 2-(2,3-diamino-6-pyridyl) malonate; 6 (4-methyl-1-pyperazinyl)-2,3-pyridinediamine; 6-(methylthio)-5 (trifluoromethyl)-2,3-pyridinediamine; 5-(trifluoromethyl)-2,3-pyridinediamine; 6-(2,2,2-trifluorethoxy)-5-(trifluoromethyl)-2,3-pyridinediamine; 6-chloro-5-(trifluoromethyl)-2,3-pyridinediamine; 5-methoxy-6-(methylthio)-2,3-pyridinediamine; 5-bromo-4-methyl-2,3-pyridinediamine; 5-(trifluoromethyl-2,3-pyridinediamine; 6-bromo-4-methyl-2,3-pyridinedlamine; 5-bromo-6-methyl-2,3-pyridinediamine; 6-methoxy-3,4-pyridinediamine; 2-methoxy-3,4-pyridinediamine; 5-methyl-3,4-pyridinediamine; 5-methoxy-3,4-pyridinediamine; 5-bromo-3,4-pyridinediamine; 2,3,4-pyridinetriamine; 2,3,5-pyridinetriamine; 4-methyl-2,3,6-pyridinetriamine; 4-(methylthio)-2,3,6-pyridinetriamine; 4-ethoxy-2,3,6-pyridinetriamine; 2,3,6-pyridinetriamine; 3,4,5-pyridinetriamine; 4-methoxy-2,3-pyridinediamine; 5-methoxy-2,3-pyridinediamine; 6-methoxy-2,3-pyridinediamine; and the biocompatible and pharmaceutically acceptable salts thereof.

Formula VI comprises a structure wherein n is 1 or 2, $R_{11}$ is an amino group or a hydroxyethyl group, and $R_{12}$ is an amino, a hydroxyalkylamino, a lower alkyl group or a group of the formula alk-Ya wherein alk is a lower alkylene group and Ya is selected from the group consisting of hydroxy, lower alkoxy, lower alkylthio, lower alkylamino and heterocyclic groups containing 4-7 ring members and 1-3 heteroatoms; with the proviso that when $R_{11}$ is a hydroxyethyl group then R, is an amino group; their biocompatible and pharmaceutically acceptable acid addition salts.

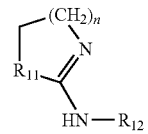

VI

The lower alkyl, lower alkylene and lower alkoxy groups referred to herein contain 1-6 carbon atoms and include methyl, methylene, methoxy, ethyl, ethylene, ethoxy, propyl, propylene, propoxy, butyl, butylene, butoxy, pentyl, pentylene, pentyloxy, hexyl, hexylene, hexyloxy and the corresponding branched chain isomers thereof. The heterocyclic groups referred to herein include 4-7 member rings having at least one and up to 3 heteroatoms therein.

Representative heterocyclic groups are those such as morpholino, piperidino, piperazino, methylpiperazino, and hexamethylenimino.

Equivalent to the compounds of Formula VI for the purpose of this invention are the biocompatible and pharmaceutically acceptable salts thereof.

Such salts can be derived from a variety of organic and inorganic acids including but not limited to, methanesulfonic, hydrochloric, toluenesulfonic, sulfuric, maleic, acetic and phosphoric acids.

Of the compounds encompassed by Formula VI, certain combinations of substituents are preferred. For instance, when $R_{11}$ is a hydroxyethyl group, then $R_{12}$ is an amino group. When $R_1$ is an amino group, then $R_{12}$ is preferably a hydroxy lower alkylamino, a lower alkyl group or a group of the formula alk-Y, wherein alk is a lower alkylene group and Y is selected from the group consisting of hydroxy, lower alkoxy, lower alkylthio, lower alkylamino and heterocyclic groups containing 4-7 ring members and 1-3 heteroatoms.

Representative of the compounds of Formula VI are: 1-amino-2-[2-(2-hydroxyethyl) hydrazino]-2-imidazoline; 1-amino-[2-(2-hydroxyethyl) hydrazino]-2-imidazoline; 1-amino-2-(2-hydroxyethylamino)-2-imidazoline; 1-(2-hydroxyethyl)-2-hydrazino-1,4,5,6-tetrahydropyrimidine; 1-(2-hydroxyethyl) 2-hydrazino-2-imidazoline; 1-amino-2-([2-(4-morpholino) ethyl]amino) imidazoline; ([2-(4-morpholino) ethyl]amino) imidazoline; 1-amino-2-([3-(4-morpholino) propyl]amino) imidazoline; 1-amino-2-([3-(4-methylpiperazin-1-yl) propyl]-amino) imidazoline; 1-amino-2-([3-(dimethylamino)propyl]amino)imidazoline; 1-amino-2-[(3-ethoxypropyl) amino] imidazoline; 1-amino-2-([3-(1-imidazolyl)propyl]amino) imidazoline; 1-amino-2-(2-methoxyethylamino)-2-imidazoline; (2-methoxyethylamino)-2-imidazoline; 1-amino-2-(3-isopropoxypropylamino)-2-imidazoline; 1-amino-2-(3-methylthiopropylamino)-2-imidazoline; 1-amino-2 [3-(1-piperidino) propylamino) imidazoline; 1-amino-2-[2,2-dimethyl-3-(dimethylamino) propylamino]-2-imidazoline; 1-amino-2-(neopentylamino)-2-imidazoline; and the biocompatible and pharmaceutically acceptable salts thereof.

Formula VII comprises a structure wherein $R_{13}$ is a hydrogen or an amino group, $R_{14}$ and $R_{15}$ are independently an amino group, a hydrazino group, a lower alkyl group, or an aryl group with the proviso that one of $R_{13}$, $R_{14}$ and $R_{15}$ must be an amino or a hydrazino group, and includes their biologically or pharmaceutically acceptable acid or alkali addition salts.

The lower alkyl groups referred to above preferably contain 1-6 carbon atoms and include methyl, ethyl, propyl, butyl, pentyl, hexyl, and the corresponding branched-chain isomers thereof.

The aryl groups encompassed by the Formula VII are those containing 6-10 carbon atoms, such as phenyl and lower alkyl substituted-phenyl, e.g. tolyl and xylyl, and phenyl substituted by 1-2 halo, hydroxy or lower alkoxy groups.

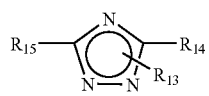

VII

The halo atoms in the Formula VII may be fluoro, chloro, bromo, or iodo. The lower alkoxy groups contain 1-6, and preferably 1-3, carbon atoms and are illustrated by methoxy, ethoxy, n-propoxy, isopropoxy and the like.

For the purposes of this invention equivalent to the compounds of Formula VII are the biologically and pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic and related acids.

Of the compounds encompassed by Formula VII, certain combinations of substituents are preferred. For instance, when $R_{13}$ is hydrogen, then $R_{14}$ is preferably an amino group. When $R_{14}$ is a hydrazino group, then R is preferably an amino group.

Representative of the compounds of Formula VII are: 3,4-diamino-5-methyl-1,2,4-triazole; 3,5-dimethyl-4H-1,2,4-triazol-4-amine; 4-triazol-4-amine; 4-triazol-4-amine; 4-triazol-4-amine; 2,4-triazole-3,4-diamine; 5-(1-ethylpropyl)-4H-1,2,4-triazole-3,4-di amine; 5-isopropyl-4H-1,2,4-triazole-3,4-diamine; 5-cyclohexyl-4H-1,2,4-triazole-3,4-diamine; 5-methyl-4H-1,2,4-triazole-3,4-diamine; 5-phenyl-4H-1,2,4-triazole-3,4-diamine; 5-propyl-4H-1,2,4-triazole-3,4-diamine; 5-cyclohexyl-4H-1,2,4-triazole-3,4-diamine.

Formula VIII comprises a structure wherein $R_{16}$ is hydrogen or an amino group, $R_{17}$ is an amino group or a guanidino group when $R_{16}$ is hydrogen, or $R_{17}$ is an amino group when $R_{16}$ is an amino group, $R_{18}$ and $R_{19}$ are independently hydrogen, hydroxy, a lower alkyl group, a lower alkoxy group, or an aryl group, and includes their biologically or pharmaceutically acceptable acid or alkali addition salts.

The lower alkyl groups in the compounds of Formula VIII preferably contain 1-6 carbon atoms and include methyl, ethyl, propyl, butyl, pentyl, hexyl, and the corresponding branched chain isomers thereof The lower alkoxy groups likewise contain 1-6, and preferably 1-3, carbon atoms, and are illustrated by methoxy, ethoxy, n-propoxy, isopropoxy and the like.

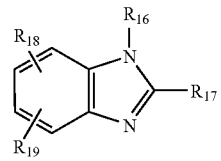

VIII

The aryl groups encompassed by the above formula are those containing 6-10 carbon atoms, such as phenyl and lower alkyl substituted-phenyl, e.g., tolyl and xylyl, and phenyl substituted by 1-2 halo, hydroxy or lower alkoxy groups.

The halo atoms in the above Formula VIII may be fluoro, chloro, bromo or iodo.

The biologically or pharmaceutically acceptable salts of the compounds of Formula VIII are those tolerated by the mammalian body and include acid addition salts derived from a variety of organic and inorganic acids such as sulfuric, phosphoric, hydrochloric, sulfamic, citric, lactic, maleic, succinic, tartaric, cinnamic, acetic, benzoic, gluconic, ascorbic and related acids. Of the compounds encompassed by Formula VIII, certain substituents are preferred. For instance, the compounds wherein R, is an amino group are preferred group.

Representative of the compounds of Formula VIII are: 2-guanidinobenzimidazole; 1,2-diaminobenzimidazole; 1,2-diaminobenzimidazole hydrochloride; 5-bromo-2-guanidinobenzimidazole; 5-methoxy-2-guanidinobenzimidazole; 5-methylbenzimidazole-1,2-diamine; 5-chlorobenzimidazole-1,2-diamine; and 2,5-diaminobenzimidazole;

Formula IX, comprising $R_{20}$—CH— (NHR21)—COOH (IX), is a structural formula wherein $R_{20}$ is selected from the group consisting of hydrogen; lower alkyl, optionally substituted by one or two hydroxyl, thiol, phenyl, hydroxyphenyl, lower alkylthiol, carboxy, aminocarboxy or amino groups and $R_{21}$, is selected from the group of hydrogen and an acyl group; and their biocompatible and pharmaceutically acceptable acid addition salts.

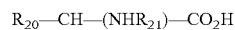

$R_{20}$—CH—(NHR$_{21}$)—CO$_2$H    IX

The lower alkyl groups of the compounds of Formula IX contain 1-6 carbon atoms and include methyl, ethyl, propyl, butyl, pentyl, hexyl and the corresponding branched chain isomers thereof.

The acyl groups referred to herein are residues of lower alkyl, aryl and heteroaryl carboxylic acids containing 2-10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group e.g., glutaryl or succinyl.

The amino acids utilized herein can possess either the L & D; stereochemical configuration or be utilized as mixtures thereof. However, the L-configuration is preferred.

Equivalent to the compounds of Formula IX for the purposes of this invention are the biocompatible and pharmaceutically acceptable salts thereof. Such salts can be derived from a variety of inorganic and organic acids such as methanesulfonic, hydrochloric, toluenesulfonic, sulfuric, maleic, acetic, phosphoric and related acids.

Representative compounds of the compounds of Formula IX are: lysine; 2,3-diaminosuccinic acid; cysteine and the biocompatible and pharmaceutically acceptable salts thereof.

Formula X comprises a structure wherein $R_{22}$ and $R_{23}$ are independently hydrogen, an amino group or a mono-or diamino lower alkyl group, $R_{24}$ and $R_{25}$ are independently hydrogen, a lower alkyl group, an aryl group, or an acyl group with the proviso one of $R_{22}$ and $R_{23}$ must be an amino group or an mono-or diamino lower alkyl group, and includes their biologically or pharmaceutically acceptable acid or alkali addition salts.

The lower alkyl groups of the compounds of Formula X contain 1-6 carbon atoms and include methyl, ethyl, propyl, butyl, pentyl, hexyl, and the corresponding branched-chain isomers thereof. The mono-or di-amino alkyl groups are lower alkyl groups substituted in the chain by one or two amino groups.

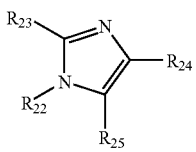

X

The aryl groups referred to herein encompass those containing 6-10 carbon atoms, such as phenyl and lower alkyl substituted-phenyl, e.g., tolyl and xylyl, and phenyl substituted by 1-2 halo, hydroxy and lower alkoxy groups. The acyl groups referred to herein are residues of lower alkyl, aryl and heteroaryl carboxylic acids containing 2-10 carbon atoms. They are typified by acetyl, propionyl, butanoyl, valeryl, hexanoyl and the corresponding higher chain and branched chain analogs thereof. The acyl radicals may also contain one or more double bonds and/or an additional acid functional group, e.g., glutaryl or succinyl.

The heteroaryl groups referred to above encompass aromatic heterocyclic groups containing 3-6 carbon atoms and one or more heteroatoms such as oxygen, nitrogen or sulfur.

The halo atoms in the above Formula X may be fluoro, chloro, bromo and iodo. The lower alkoxy groups contain 1-6, and preferably 1-3, carbon atoms and are illustrated by methoxy, ethoxy, propoxy, isopropoxy and the like.

The term biologically or pharmaceutically acceptable salts refers to salts which are tolerated by the mammalian body and are exemplified by acid addition salts derived from a variety of organic and inorganic acids such as sulfuric, phosphoric, hydrochloric hydrobromic, hydroiodic, sulfamic, citric, lactic, maleic, succinic, tartaric, cinnamic, acetic, benzoic, gluconic, ascorbic and related acids.

Of the compounds encompassed by Formula X, certain combinations of substituents are preferred. For instance, when $R_{22}$ and $R_{23}$ are both amino groups, then $R_{24}$ and $R_{25}$ are preferably both hydrogen atoms. When $R_{22}$ or $R_{23}$ is amino group and one of $R_{24}$ or $R_{25}$ is an aryl group, the other of $R_{24}$ and $R_{25}$ is preferably hydrogen.

Representative compounds of Formula X are: 1,2-diamino-4-phenyl[1H]imidazole; 1,2-diaminoimidazole; 1-(2, 3-diaminopropyl) imidazole trihydrochloride; 4-(4-bromophenyl)imidazole-1,2-diamine; 4-(4-chlorophenyl) imidazole-1,2-diamine; 4-(4-hexylphenyl)imidazole-1,2-diamine; 4-(4-methoxyphenyl)imidazole-1,2-diamine; 4-phenyl-5-propylimidazole-1,2-diamine; 1,2-diamino-4-methylimidazole; 1,2-diamino-4,5-dimethylimidazole; and 1,2-diamino-4-methyl-5-acetylimidazole.

Formula XI comprises a structure wherein $R_{26}$ is a hydroxy, lower alkoxy, amino, amino lower alkoxy, monolower alkylamino lower alkoxy, di-lower alkylamino lower alkoxy or hydrazino group, or a group of the formula—$NR_{29}R_{30}$, wherein $R_{29}$ is hydrogen or lower alkyl, and $R_{30}$ is an alkyl group of 1-20 carbon atoms, an aryl group, a hydroxy lower alkyl group, a carboxy lower alkyl group, cyclo lower alkyl group or a heterocyclic group containing 4-7 ring members and 1-3 heteroatoms; or $R_{29}$ and $R_{30}$ together with the nitrogen form a morpholino, piperidinyl, or piperazinyl group; or when $R_{29}$ is hydrogen, then $R_{30}$ can also be a hydroxy group; $R_{27}$ is 0-3 amino or nitro groups, and/or a hydrazino group, a hydrazinosulfonyl group, a hydroxyethylamino or an amidino group; $R_{28}$ is hydrogen or one or two fluoro, hydroxy, lower alkoxy, carboxy, lower alkylamino, di-lower alkylamino or a hydroxy lower alkylamino groups; with the proviso that when $R_{26}$ is hydroxy or lower alkoxy, then $R_{27}$ is a non-hydrogen substituent; with the further proviso that when $R_{26}$ is hydrazino, then there must be at least two non-hydrogen substituents on the phenyl ring; and with the further proviso that when $R_{28}$ is hydrogen, then $R_{30}$ can also be an aminoimino, guanidyl, aminoguanidinyl or diaminoguanidyl group, and includes their pharmaceutically acceptable salts and hydrates.

The lower alkyl groups of the compounds of Formula XI contain 1-6 carbon atoms and include methyl, ethyl, propyl, butyl, pentyl, hexyl, and the corresponding branched-chain isomers thereof. The cycloalkyl groups contain 4-7 carbon atoms and are exemplified by groups such as cyclobutyl, cyclopentyl, cyclohexyl, 4-methylcyclohexyl and cycloheptyl groups.

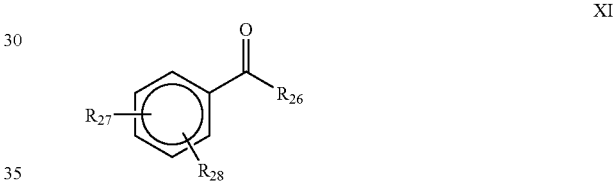

XI

The heterocyclic groups of the compounds of Formula XI include 4-7 membered rings having at least one and up to 3 heteroatoms, e.g., oxygen, nitrogen, or sulfur, therein, and including various degrees of unsaturation.

Representatives of such heterocyclic groups are those such as morpholino, piperidino, homopiperidino, piperazino, methylpiperazino, hexamethylenimino, pyridyl, methylpyridyl, imidazolyl, pyrrolidinyl, 2,6-dimethylmorpholino, furfural, 1,2,4-triazoylyl, thiazolyl, thiazolinyl, methylthiazolyl, and the like.

Equivalent to the compounds of Formula XI for the purposes of this invention are the biocompatible and pharmaceutically acceptable salts and hydrates thereof. Such salts can be derived from a variety of organic and inorganic acids, including, but not limited to, methanesulfonic, hydrochloric, hydrobromic, hydroiodic, toluenesulfonic, sulfuric, maleic, acetic and phosphoric acids.

When the compounds of Formula XI contain one or more asymmetric carbon atoms, mixtures of enantiomers, as well as the pure (R) or (S) enantiomeric form can be utilized in the practice of this invention.

In addition, compounds having a 3,4-diamino- or 2,3-diamino-5-fluoro substituent pattern on the phenyl ring are highly preferred.

Representative compounds of formula XI of the present invention are: 4-(cyclohexylamino-carbonyl)-o-phenylene diamine hydrochloride; 3,4-diaminobenzhydrazide; 4-(n-butylamino-carbonyl)-o-phenylene-diamine dihydrochloride; 4-(ethylamino-carbonyl)-o-phenylene-diamine dihydrochloride; 4-carbamoyl-o-phenylene diamine hydrochloride;

4-(morpholino-carbonyl)-o-phenylene-diamine hydrochloride; 4-[(4-morpholino)hydrazino-carbonyl]-o-phenylenediamine; 4-(1-piperidinylamino-carbonyl)-o-phenylenediamine dihydrochloride; 2,4-diamino-3-hydroxybenzoic acid; 4,5-diamino-2-hydroxybenzoic acid; 3,4-diaminobenzamide; 3,4-diaminobenzhydrazide; 3,4-diamino-N,N-bis(1-methylethyl) benzamide; 3,4-diamino-N,N-diethylbenzamide; 3,4-diamino-N,N-dipropylbenzamide; 3,4-diamino-N-(2-furanylmethyl) benzamide 3,4-diamino-N-(2-methylpropyl) benzamide; benzamide; 3,4-diamino-N-(5-methyl-2-thiazolyl) benzamide; 3,4-diamino-N-(6-methoxy-2-benzothiazolyl)benzamide; 3,4-diamino-N-(6-methoxy-8-quinolinyl)benzamide; 3,4-diamino-N-(6-methyl-2-pyridinyl)benzamide; 3,4-diamino-N-(1H-benzimidazol-2-yl)benzamide; 3,4-diamino-N-(2-pyridinyl)benzamide; 3,4-diamino-N-(2-thiazolyl) benzamide; 3,4-diamino-N-(4-pyridinyl)benzamide; 3,4-diamino-N-[9H-pyrido(3,4-b)indol-6-yl] benzamide 3,4-diamino-N-butylbenzamide; 3,4-diamino-N-cyclohexylbenzamide; 3,4-diamino-N-cyclopentylbenzamide; 3,4-diamino-N-decylbenzamide; 3,4-diamino-N-dodecylbenzamide; 3,4-diamino-N-methylbenzamide; 3,4-diamino-N-octylbenzamide; 3,4-diamino-N-pentylbenzamide; 3,4-diamino-N-phenylbenzamide; 4-(diethylamino-carbonyl)-o-phenylene diamine; 4-(tert-butylamino-carbonyl)-o-phenylene diamine; 4-isobutylamino-carbonyl)-o-phenylene diamine; 4-(neopentylamino-carbonyl)-o-phenylene diamine; 4-(dipropylamino-carbonyl)-o-phenylene diamine; 4-(n-hexylamino-carbonyl)-o-phenylene diamine; 4-(n-decylamino-carbonyl)-o-phenylene diamine; 4-(n-dodecylamino-carbonyl)-o-phenylene diamine; 4-(1-hexadecylamino-carbonyl)-o-phenylene diamine; 4-(octadecylamino-carbonyl)-o-phenylene diamine; 4-(hydroxylamino-carbonyl)-o-phenylene diamine; 4-(2-hydroxyethylamino-carbonyl)-o-phenylene; 4-[(2-hydroxyethylamino)ethylamino-carbonyl]-o-phenylene diamine; 4-[(2-hydroxyethyloxy)ethylamino-carbonyl]-o-phenylene diamine; 4-(6-hydroxyhexylamino-carbonyl)-o-phenylene diamine; 4-(3-ethoxypropylamino-carbonyl)-o-phenylene diamine; 4-(3-isopropoxypropylamino-carbonyl)-o-phenylene diamine; 4-(3-dimethylaminopropylamino-carbonyl)-o-phenylene diamine; 4-[4-(2-aminoethyl) morpholino-carbonyl]-o-phenylene diamine; 4-[4-(3-aminopropyl) morpholino-carbonyl]-o-phenylene diamine; 4-N-(3-aminopropyl)pyrrolidino-carbonyl]-o-phenylene diamine; 4-[3-(N-piperidino)propylamino-carbonyl]-o-phenylene diamine; 4-[3-(4-methylpiperazinyl)propylamino-carbonyl]-o-phenylene diamine; 4-(3-imidazoylpropylamino-carbonyl)-o-phenylene diamine; 4-(3-phenylpropylamino-carbonyl)-o-phenylenediamine; 4-[2-(N,N-diethylamino) ethylamino-carbonyl]-o-phenylene diamine; 4-(imidazolylamino-carbonyl)-o-phenylene diamine; 4-(pyrrolidinyl-carbonyl)-o-phenylene diamine; 4-(piperidino-carbonyl)-o-phenylene diamine; 4-(1-methylpiperazinyl-carbonyl)-o-phenylene diamine; 4-(2,6-dimethylmorpholino-carbonyl)-o-phenylenediamine; 4-(pyrrolidin-1-ylamino-carbonyl)-o-phenylene diamine; 4-(homopiperidin-1-ylamino-carbonyl)-o-phenylene diamine; 4-(4-methylpiperazine-1-ylamino-carbonyl)-o-phenylene diamine; 4-(1,2,4-triazol-1-ylamino-carbonyl)-o-phenylene diamine; 4-(guanidinyl-carbonyl)-o-phenylene diamine; 4-(guanidinylamino-carbonyl)-o-phenylene diamine; 4-aminoguanidinylamino-carbonyl)-o-phenylene diamine; 4-(diaminoguanidinylamino-carbonyl)-o-phenylene diamine; 3,4-aminosalicylic acid 4-guanidinobenzoic acid; 3,4-diaminobenzohydroxamic acid; 3,4,5-triaminobenzoic acid; 2,3-diamino-5-fluoro-benzoic acid; and 3,4-diaminobenzoic acid; and their pharmaceutically acceptable salts and hydrates.

Formula XII comprises a structure wherein $R_{31}$, is hydrogen, a lower alkyl or hydroxy group; $R_{32}$ is hydrogen, hydroxy lower alkyl, a lower alkoxy group, a lower alkyl group, or an aryl group; $R_{33}$ is hydrogen or an amino group; and their biologically or pharmaceutically acceptable acid addition salts.

The lower alkyl groups of the compounds of Formula XII contain 1-6 carbon atoms and include methyl, ethyl, propyl, butyl, pentyl, hexyl, and the corresponding branched-chain isomers thereof. Likewise, the lower alkoxy groups contain 1-6, and preferably 1-3, carbon atoms and include methoxy, ethoxy, isopropoxy, propoxy, and the like. The hydroxy lower alkyl groups include primary, secondary and tertiary alcohol substituent patterns.

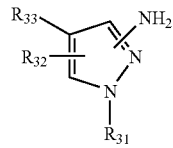

XII

The aryl groups of the compounds of Formula XII encompass those containing 6-10 carbon atoms, such as phenyl and lower alkyl substituted-phenyl, e.g., tolyl and xylyl, and phenyl substituted by 1-2 halo, hydroxy and lower alkoxy groups.

The halo atoms in the above Formula XII may be fluoro, chloro, bromo, and iodo.

The term biologically or pharmaceutically acceptable salts refers to salts which are tolerated by the mammalian body and are exemplified by acid addition salts derived from a variety of organic and inorganic acids such as sulfuric, phosphoric, hydrochloric hydrobromic, hydroiodic, sulfamic, citric, lactic, maleic, succinic, tartaric, cinnamic, acetic, benzoic, gluconic, ascorbic and related acids.

Of the compounds encompassed by Formula XII, certain substituents are preferred. For instance, the compounds wherein R32 is hydroxy and $R_{33}$ is an amino group are preferred.

Representative of the compounds of Formula XII are: 3,4-diaminopyrazole; 3,4-diamino-5-hydroxypyrazole; 3,4-diamino-5-methylpyrazole 3,4-diamino-5-methoxypyrazole; 3,4-diamino-5-phenylpyrazole; 1-methyl-3-hydroxy-4,5-diaminopyrazole; 1-(2-hydroxyethyl)-3-hydroxy-4,5-diaminopyrazole; 1-(2-hydroxyethyl)-3-phenyl-4,5-diaminopyrazole; 1-(2-hydroxyethyl)-3-methyl-4,5-diaminopyrazole; 1-(2-hydroxyethyl)-4,5-diaminopyrazole; 1-(2-hydroxypropyl)-3-hydroxy-4,5-diaminopyrazole; 3-amino-5-hydroxypyrazole; and 1-(2-hydroxy-2-methylpropyl)-3-hydroxy-4,5-diaminopyrazole; and their biologically and pharmaceutically acceptable acid addition salts.

Formula XIII comprises a structure where n=1-6, wherein X is $-NR_1-$, $-S(O)-$, $-S(O)_2-$, or $-O-$, $R_1$ being selected from the group consisting of H, linear chain alkyl group $(C_1-C_6)$ and branched chain alkyl group $(C_1-C_6)$. $Y=-N-$, $-NH-$, or $-O-$ and Z is selected from the group consisting of H, linear chain alkyl group $(C_1-C_6)$ and branched chain alkyl group $(C_1-C_6)$.

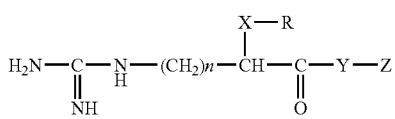

XIII

For Formula XIV, wherein $R_{37}$ is a lower alkyl group, or a group of the formula NR41NR42, wherein $R_{41}$, is hydrogen and $R_{42}$ is a lower alkyl group or a hydroxy (lower) alkyl group; or $R_{41}$, and $R_{42}$ together with the nitrogen atom are a heterocyclic group containing 4-6 carbon atoms and, in addition to the nitrogen atom, 0-1 oxygen, nitrogen or sulfur atoms; $R_{38}$ is hydrogen or an amino group; $R_{39}$ is hydrogen or an amino group; $R_{40}$ is hydrogen or a lower alkyl group; with the proviso that at least one of $R_{38}$, $R_{39}$, and $R_{40}$ is other than hydrogen; and with the further proviso that $R_{37}$ and $R_{38}$ cannot both be amino groups; and their pharmaceutically acceptable acid addition salts.

The lower alkyl groups of the compounds of Formula XIV contain 1-6 carbon atoms and include methyl, ethyl, propyl, butyl, pentyl, hexyl, and the corresponding branched-chain isomers thereof.

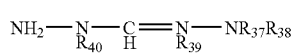

XIV

The heterocyclic groups formed by the NR41 $R_{42}$ group are 4-7 membered rings having at 0-1 additional heteroatoms, e.g., oxygen, nitrogen, or sulfur, therein, and including various degrees of unsaturation. Representatives of such heterocyclic groups are those such as morpholino, piperidino, hexahydroazepino, piperazino, methylpiperazino, hexamethylenimino, pyridyl, methylpyridyl, imidazolyl, pyrrolidinyl, 2,6-dimethylmorpholino, 1,2,4-triazoylyl, thiazolyl, thiazolinyl, and the like.

Equivalent to the compounds of Formula XIV for the purposes of this invention are the biocompatible and pharmaceutically acceptable salts thereof. Such salts can be derived from a variety of organic and inorganic acids, including, but not limited to, methanesulfonic, hydrochloric, hydrobromic, hydroiodic, toluenesulfonic, sulfuric, maleic, acetic and phosphoric acids.

When the compounds of Formula XIV contain one or more asymmetric carbon atoms, mixtures of enantiomers, as well as the pure (R) or (S) enantiomeric form can be utilized in the practice of this invention.

Of the compounds encompassed by Formula XIV, certain combinations of substituents are preferred. For instance, compounds wherein $R_{37}$ is a heterocyclic group, and particularly a morpholino or a hexahydroazepino group, are highly preferred.

Representative of the compounds of Formula XIV are: 2-(2-hydroxy-2-methylpropyl)hydrazinecarboximidic hydrazide; N-(4-morpholino)hydrazinecarboximidamide; 1-methyl-N-(4-morpholino)hydrazinecarboximidamide; 1-methyl-N-(4-piperidino)hydrazinecarboximidamide; 1-(N-hexahydroazepino) hydrazinecarboximidamide; N,N-dimethylcarbonimidic dihydrazide; 1-methylcarbonimidic dihydrazide; 2-(2-hydroxy-2-methylpropyl) carbohydrazonic dihydrazide; and N-ethylcarbonimidic dihydrazide.

Formula XV is a structure comprising (R43HN=) CR44-W-CR45 (=NHR43) (XV); wherein $R_{43}$ is pyridyl, phenyl or a carboxylic acid substituted phenyl group of the formula;

wherein $R_{46}$ is hydrogen, lower alkyl or a water-solubilizing ester moiety; W is a carbon-carbon bond or an alkylene group of 1-3 carbon atoms, $R_{44}$ is a lower alkyl, aryl, or heteroaryl group and $R_{45}$ is hydrogen, a lower alkyl, aryl or heteroaryl group; and it includes their biologically or pharmaceutically acceptable acid addition salts.

The lower alkyl groups of the compounds of Formula XV preferably contain 1-6 carbon atoms and include methyl, ethyl, propyl, butyl, pentyl, hexyl, and the corresponding branched-chain isomers thereof. These groups are optionally substituted by one or more halo, hydroxy, amino or lower alkylamino groups.

The alkylene groups of the compounds of Formula XV likewise can be straight or branched chain, and are thus exemplified by ethylene, propylene, butylene, pentylene, hexylene, and their corresponding branched chain isomers.

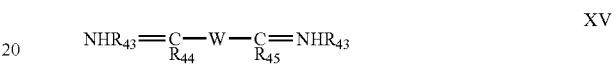

XV

In the R groups which are a carboxylic acid substituted phenyl group of the formula:

wherein $R_{44}$ is hydrogen, lower alkyl or a water-solubilizing ester moiety, the water solubilizing ester moiety can be selected from a variety of such esters known in the art. Typically, these esters are derived from dialkylene or trialkylene glycols or ethers thereof, dihydroxyalkyl groups, arylalkyl group, e.g., nitrophenylalkyl and pyridylalkyl groups, and carboxylic acid esters and phosphoric acid esters of hydroxy and carboxy-substituted alkyl groups. Particularly preferred water solubilizing ester moieties are those derived from 2,3-dihydroxypropane, and 2-hydroxyethylphosphate.

The aryl groups encompassed by the above Formula XV are those containing 6-10 carbon atoms, such as phenyl and lower alkyl substituted-phenyl, e.g., tolyl and xylyl, and are optionally substituted by 1-2 halo, nitro, hydroxy or lower alkoxy groups.

Where the possibility exists for substitution of a phenyl or aryl ring, the position of the substituents may be ortho, meta, or para to the point of attachment of the phenyl or aryl ring to the nitrogen of the hydrazine group.

The halo atoms in the above Formula XV may be fluoro, chloro, bromo or iodo. The lower alkoxy groups contain 1-6, and preferably 1-3, carbon atoms and are illustrated by methoxy, ethoxy, n-propoxy, isopropoxy and the like.

The heteroaryl groups in the above Formula XV contain 1-2 heteroatoms, i.e., nitrogen, oxygen or sulfur, and are exemplified by furyl, pyrrolinyl, pyridyl, pyrimidinyl, thienyl, quinolyl, and the corresponding alkyl substituted compounds.

For the purposes of this invention equivalent to the compounds of Formula XV are the biologically and pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by Formula XV, certain substituents are preferred. For instance, the compounds wherein W is a carbon-carbon bond, $R_{44}$ is a methyl group and $R_{45}$ is hydrogen are preferred.

Representative of the compounds of Formula XV are: methylglyoxal bis-(2-hydrazino-benzoic acid)hydrazone; methylglyoxal bis-(dimethyl-2-hydrazinobenzoate)hydrazone; methylglyoxal bis-(phenylhydrazine)hydrazone; methyl glyoxal bis-(dimethyl-2-hydrazinobenzoate)hydrazone; methylglyoxal bis-(4-hydrazinobenzoic acid)hydrazone; methylglyoxal bis-(dimethyl-4-hydrazinobenzoate) hydrazone; methylglyoxal bis-(2-pyridyl)hydrazone; methylglyoxal bis-(diethyleneglycol methylether-2-hydrazinobenzoate)hydrazone; methylglyoxal bis-[1-(2,3-dihydroxypropane)-2-hydrazinebenzoatehydrazone; methyl glyoxal bis-[1-(2-hydroxyethane)-2-hydrazinobenzoate]hydrazone; methylglyoxal bis-[(1-hydroxymethyl-1-acetoxy))-2-hydrazino-2-benzoate]hydrazone; methylglyoxal bis-[(4-nitrophenyl)-2-hydrazinobenzoate]hydrazone; methylglyoxal bis-[(4-methylpyridyl)-2-hydrazinobenzoate]hydrazone; methylglyoxal bis-(triethylene glycol 2-hydrazinobenzoate) hydrazone; and methylglyoxal bis-(2-hydroxyethylphosphate-2-hydrazinebenzoate)hydrazone.

Formula XVI comprises a structure wherein $R_{47}$ and $R_{48}$ are each hydrogen or, together, are an alkylene group of 2-3 carbon atoms, or, when $R_{47}$ is hydrogen, then $R_{48}$ can be a group of the formula alk—N—$R_{50}$ $R_{51}$, wherein alk is a straight or branched chain alkylene group of 1-8 carbon atoms, and $R_{50}$ and $R_5$, are independently each a lower alkyl group of 1-6 carbon atoms, or together with the nitrogen atom form a morpholino, piperdinyl or methylpiperazinyl group; $R_{49}$ is hydrogen, or when $R_{47}$ and $R_{48}$ are together an alkylene group of 2-3 carbon atoms, a hydroxyethyl group; W is a carbon-carbon bond or an alkylene group of 1-3 carbon atoms, and $R_{52}$ is a lower alkyl, aryl, or heteroaryl group and $R_{53}$ is hydrogen, a lower alkyl, aryl or heteroaryl group; with the proviso that when W is a carbon-carbon bond, then $R_{52}$ and $R_{53}$ together can also be a 1,4-butylene group; or W is a 1,2-, 1,3-, or 1,4-phenylene group, optionally substituted by one or two lower alkyl or amino groups, a 2,3-naphthylene group; a 2,5-thiophenylene group; or a 2,6-pyridylene group; and $R_{52}$ and $R_{53}$ are both hydrogen or both are lower alkyl groups; or W is an ethylene group and $R_{52}$ and $R_{53}$ together are an ethylene group; or W is an ethenylene group and $R_{52}$ and $R_{53}$ together are an ethenylene group; or W is a methylene group and $R_{52}$ and $R_{53}$ together are a group of the formula =C(—$CH_3$)—N—($H_3C$—) C=or —C—W—C-and $R_{52}$ and $R_{53}$ together form a bicyclo-(3,3,1)-nonane or a bicyclo-3,3,1-octane group and $R_{47}$ and $R_{48}$ are together an alkylene group of 2-3 carbon atoms and $R_{49}$ is hydrogen; and their biologically or pharmaceutically acceptable acid addition salts.

The lower alkyl groups of the compounds of Formula XVI preferably contain 1-6 carbon atoms and include methyl, ethyl, propyl, butyl, pentyl, hexyl, and the corresponding branched-chain isomers thereof. These groups are optionally substituted by one or more halo hydroxy, amino or lower alkylamino groups.

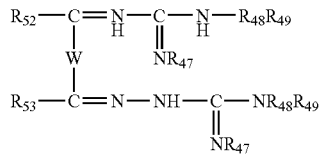

XVI

The alkylene groups of the compounds of Formula XVI likewise can be straight or branched chain, and are thus exemplified by ethylene, propylene, butylene, pentylene, hexylene, and their corresponding branched chain isomers.

The aryl groups encompassed by the above Formula XVI are those containing 6-10 carbon atoms, such as phenyl and lower alkyl substituted-phenyl, e.g. tolyl and xylyl, and are optionally substituted by 1-2 halo, hydroxy or lower alkoxy groups.

The halo atoms in the above Formula XVI may be fluoro, chloro, bromo or iodo. The lower alkoxy groups contain 1-6, and preferably 1-3, carbon atoms and are illustrated by methoxy, ethoxy, n-propoxy, isopropoxy and the like.

The heteroaryl groups in the above Formula XVI contain 1-2 heteroatoms, i.e. nitrogen, oxygen or sulfur, and are exemplified by be furyl, pyrrolinyl, pyridyl, pyrimidinyl, thienyl, quinolyl, and the corresponding alkyl substituted compounds.

For the purposes of this invention equivalent to the compounds of Formula XVI are the biologically and pharmaceutically acceptable acid addition salts thereof. Such acid addition salts may be derived from a variety of organic an inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by Formula XVI, certain substituents are preferred. For instance, the compounds wherein $R_{48}$ and $R_{49}$ are together an alkylene group of 2-3 carbon atoms are preferred. The compounds wherein $R_{52}$ and $R_{53}$ together are a butylene, ethylene, or an ethenylene group and those wherein $R_{52}$ and $R_{53}$ are both methyl or furyl groups are also highly preferred.

Representative of the compounds of Formula XVI are: methyl glyoxal bis guanylhydrazone); methyl glyoxal bis(2-hydrazino-2-imidazoline-hydrazone); terephthaldicarboxaldehyde bis(2-hydrazino-2-imidazoline hydrazone); terephaldicarboxaldehyde bis(guanylhydrazone); phenylglyoxal bis (2-hydrazino-2-imidazoline hydrazone); furylglyoxal bis(2-hydrazino-2-imidazoline hydrazone); methyl glyoxal bis (1-(2-hydroxyethyl)-2-hydrazino-2-imidazoline hydrazone); methyl glyoxal bis(1-(2-hydroxyethyl)-2-hydrazino-1,4,5,6-tetrahydropyrimidine hydrazone); phenyl glyoxal bis (guanylhydrazone); phenyl glyoxal bis(1-(2-hydroxyethyl)-2-hydrazino-2-imidazoline hydrazone); furyl glyoxal bis(1-(2-hydroxyethyl)-2-hydrazino-2-imidazoline hydrazone); phenyl glyoxal bis(1-(2-hydroxyethyl)-2-hydrazino-1,4,5,6-tetrahydropyrimidine hydrazone); furyl glyoxal bis(1-(2-hydroxyethyl)-2-hydrazino-1,4,5,6-tetrahydropyrimidine hydrazone); 2,3-butanedione bis (2-hydrazino-2-imidazoline hydrazone); 1,4-cyclohexanedione bis(2-hydrazino-2-imidazoline hydrazone); o-phthalic dicarboxaldehyde bis(2-hyd carboximidamide hydrazone); furylglyoxal bis(guanyl hydrazone)dihydrochloride dihydrate; 2,3-pentanedione bis (2-tetrahydropyrimidine)hydrazone dihydrobromide; 1,2-cyclohexanedione bis(2-tetrahydropyrimidine)hydrazone dihydrobromide; 2,3-hexanedione bis(2-tetrahydropyrimidine) hydrazone dihydrobromide; 1,3-diacetyl bis (2-tetrahydropyrimidine)hydrazone dihydrobromide; 2,3-butanedione bis(2-tetrahydropyrimidine)hydrazone dihydrobromide; 2,6-diacetylpyridine-bis-(2-hydrazino-2-imidazoline hydrazone)dihydrobromide; 2,6-diacetylpyridine-bis-(guanyl hydrazone)dihydrochloride; 2,6-pyridine dicarboxaldehyde-bis-(2-hydrazino-2-imidazoline hydrazone)dihydrobromide trihydrate); 2,6-pyridine dicarboxaldehyde-bis (guanyl hydrazone)dihydrochloride; 1,4-diacetyl benzene-bis-(2-hydrazino-2-imidazoline hydrazone)dihydrobromide dihydrate; 1,3-diacetyl benzene-bis-(2-hydrazino-2-imidazoline)hydrazone dihydrobromide; 1,3-diacetyl benzene-bis (guanyl)-hydrazone dihydrochloride; isophthalaldehyde-bis-(2-hydrazino-2-imidazoline) hydrazone dihydrobromide; isophthalaldehyde-bis-(guanyl)hydrazone dihydrochloride; 2,6-diacetylaniline bis-(guanyl)hydrazone dihydrochloride; 2,6-diacetyl aniline bis-(2-hydrazino-2-imidazoline)hydrazone dihydrobromide; 2,5-diacetylthiophene bis(guanyl)hydrazone dihydrochloride; 2,5-diacetylthiophene bis-(2-hydrazino-2-imidazoline)hydrazone dihydrobromide; 1,4-cyclohexanedione bis(2-tetrahydropyrimidine)hydrazone dihydrobromide; 3,4-hexanedione bis(2-tetrahydropyrimidine)hydrazone dihydrobromide; methylglyoxal-bis-(4-amino-3-hydrazino-1,2,4-triazole)hydrazone dihydrochloride; methylglyoxal-bis-(4-amino-3-hydrazino-5-methyl-1,2,4-triazole)hydrazone dihydrochloride; 2,3-pentanedione-bis-(2-hydrazino-3-imidazoline)hydrazone dihydrobromide; 2,3-hexanedione-bis-(2-hydrazino-2-imidazoline)hydrazone dihydrobromide; 3-ethyl-2,4-pentane dione-bis-(2-hydrazino-2-imidazoline) hydrazone dihydrobromide; methylglyoxal-bis-(4-amino-3-hydrazino-5-ethyl-1,2,4-triazole)hydrazone dihydrochloride; methylglyoxal-bis-(4-amino-3-hydrazino-5-isopropyl-1,2,4-triazole)hydrazone dihydrochloride; methyl glyoxal-bis-(4-amino-3-hydrazino-5-cyclopropyl-1,2,4-triazole) hydrazone dihydrochlorimethylglyoxal-bis-(4-amino-3-hydrazino-5-cyclobutyl-1,2,4-triazole) hydrazone dihydrochloride; 1,3-cyclohexanedione-bis-(2-hydrazino-2-imidazoline) hydrazone dihydrobromide; 6-dimethylpyridine bis(guanyl)hydrazone dihydrochloride; 3,5-diacetyl-1,4-dihydro-2,6-dimethylpyridine bis-(2-hydrazino-2-imidazoline hydrazone dihydrobromide; bicyclo-(3,3,1)nonane-3,7-dione bis-(2-hydrazino-2-imidazoline)hydrazone dihydrobromide; and cis-bicyclo-(3,3,1)octane-3,7-dione bis-(2-hydrazino-2-imidazoline)hydrazone dihydrobromide.

Figure XVII comprises a structure wherein $R_{54}$ and $R_{55}$ are independently selected from the group consisting of hydrogen, hydroxy (lower) alkyl, lower acyloxy (lower) alkyl, lower alkyl, or $R_{54}$ and $R_{55}$ together with their ring carbons may be an aromatic fused ring; Za is hydrogen or an amino group;

Ya is hydrogen, or a group of the formula-$CH_2C$ (=O)—$R_{56}$ wherein R is a lower alkyl, alkoxy, hydroxy, amino or aryl group; or a group of the formula—CHR' wherein R' is hydrogen, or a lower alkyl, lower alkynyl, or aryl group; and A is a halide, tosylate, methanesulfonate or mesitylenesulfonate ion.

The lower alkyl groups of the compounds of Formula XVII contain 1-6 carbon atoms and include methyl, ethyl, propyl, butyl, pentyl, hexyl, and the corresponding branched-chain isomers thereof. The lower alkynyl groups contain from 2 to 6 carbon atoms. Similarly, the lower alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or lower alkylamino groups.

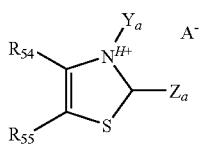

XVII

The lower acyloxy (lower) alkyl groups encompassed by the above Formula XVII include those wherein the acyloxy portion contain from 2 to 6 carbon atoms and the lower alkyl portion contains from 1 to 6 carbon atoms.

Typical acyloxy portions are those such as acetoxy or ethanoyloxy, propanoyloxy, butanoyloxy, pentanoyloxy, hexanoyloxy, and the corresponding branched chain isomers thereof. Typical lower alkyl portions are as described herein above. The aryl groups encompassed by the above formula are those containing 6-10 carbon atoms, such as phenyl and lower alkyl substituted-phenyl, e.g., tolyl and xylyl, and are optionally substituted by 1-2 halo, hydroxy, lower alkoxy or di (lower) alkylamino groups. Preferred aryl groups are phenyl, methoxyphenyl and 4-bromophenyl groups.

The halo atoms in the above Formula XVII may be fluoro, chloro, bromo, or iodo.

For the purposes of this invention, the compounds of Formula XVII are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Of the compounds encompassed by Formula XVII, certain substituents are preferred. For instance, the compounds wherein $R_{54}$ or $R_{55}$ are lower alkyl groups are preferred. Also highly preferred are the compounds wherein Ya is a 2-phenyl-2-oxoethyl or a 2-[4'-bromophenyl]-2-oxoethyl group.

Representative of the compounds of Formula XVII are: 3-aminothiazolium mesitylenesulfonate; 3-amino-4,5-dimethylaminothiazolium mesitylenesulfonate; 2,3-diaminothiazolinium mesitylenesulfonate; 3-(2-methoxy-2-oxoethyl)-thiazolium bromide; 3-(2-methoxy-2-oxoethyl)-4,5-dimethylthiazolium bromide; 3-(2-methoxy-2-oxoethyl)-4-methylthiazolium bromide; 3-(2-phenyl-2-oxoethyl)-4-methylthizolium bromide; 3-(2-phenyl-2-oxoethyl)-4,5-dimethylthiazolium bromide; 3-amino-4-methylthiazolium mesitylenesulfonate; 3-(2-methoxy-2-oxoethyl)-5-methylthiazolium bromide; 3-(3-(2-phenyl-2-oxoethyl)-5-methylthiazolium bromide; 3-[2-(4'-bromophenyl)-2-oxoethyl] thiazolium bromide; 3-[2-(4'-bromophenyl)-2-oxoethyl]-4-methylthiazolium bromide; 3-[2-(4'-bromophenyl)-2-oxoethyl]-5-methylthiazolium bromide; 3-[2-(4'bromophenyl)-2-oxoethyl]-4,5-dimethylthiazolium bromide; 3-(2-methoxy-2-oxoethyl)-4-methyl-5-(2-hydroxyethyl) thiazolium bromide; 3-(2-phenyl-2-oxoethyl)-4-methyl-5-(2-hydroxyethyl) thiazolium bromide; 3-[2-(4'-bromophenyl)-2-oxoethyl]-4-methyl-5-(2-hydroxyethyl) thiazolium bromide; 3,4-dimethyl-5-(2-hydroxyethyl) thiazolium iodide; 3-ethyl-5-(2-hydroxyethyl)-4-methylthiazolium bromide; 3-benzyl-5-(2-hydroxyethyl)-4-methylthiazolium chloride; 3-(2-methoxy-2-oxoethyl)benzothiazolium bromide; 3-(2-phenyl-2-oxoethyl)benzothiazolium bromide; 3-[2-(4'bromophenyl)-2-oxoethyl] benzothiazolium bromide; 3-(carboxymethyl) benzothiazolium bromide; 2,3-(diamino) benzothiazolium mesitylenesulfonate; 3-(2-amino-2-oxoethyl) thiazolium bromide; 3-(2-amino-2-oxoethyl)-4-methylthiazolium bromide; 3-(2-amino-2-oxoethyl)-5-methylthiazolium bromide; 3-(2-amino-2-oxoethyl) 4,5-dimethylthiazolium bromide; 3-(2-amino-2-oxoethyl) benzothiazolium bromide; 3-(2-amino-2-oxoethyl) 4-methyl-5-(2-hydroxyethyl)thiazolium bromide; 3-amino-5-(2-hydroxyethyl)-4-methylthiazolium mesitylenesulfonate; 3-(2-methyl-2-oxoethyl)thiazolium chloride; 3-amino-4-methyl-5-(2-acetoxyethyl)thiazolium mesitylenesulfonate; 3-(2-phenyl-2-oxoethyl)thiazolium bromide; 3-(2-methoxy-2-oxoethyl)-4-methyl-5-(2-acetoxyethyl)

thiazoliumbromide; 3-(2-amino-2-oxoethyl)-4-methyl-5-(2-acetoxyethyl)thiazolium bromide; 2-amino-3-(2-methoxy-2-oxoethyl) thiazolium bromide; 2-amino-3-(2-methoxy-2-oxoethyl) benzothiazolium bromide; 2-amino-3-(2-amino-2-oxoethyl)thiazolium bromide; 2-amino-3-(2-amino-2-oxoethyl)benzothiazolium bromide; 3-[2-(4'-methoxyphenyl)-2-oxoethyl]-thiazolinium bromide; 3-[2-(2',4'-dimethoxyphenyl)-2-oxoethyl]-thiazolinium bromide; 3-[2-(4'-fluorophenyl)-2-oxoethyl]-thiazolinium bromide; 3-[2-(2',4'-difluorophenyl)-2-oxoethyl]-thiazolinium bromide; 3-[2-(4'-diethylaminophenyl)-2-oxoethyl]-thiazolinium bromide; 3-propargyl-thiazolinium bromide; 3-propargyl-4-methylthiazolinium bromide; 3-propargyl-5-methylthiazolinium bromide; 3-propargyl-4,5-dimethylthiazolinium bromide; and 3-propargyl-4-methyl-5-(2-hydroxyethyl)-thiazolinium bromide.

Formula XVIII comprises a structure wherein, $R_{57}$ is OH, $NHCONR_{61}R_{62}$, or $N=C(NR_{61}R_{62})_2$;

$R_{61}$, and $R_{62}$ are each independently selected from the group consisting of: hydrogen; $C_{1-10}$ alkyl, straight or branched chain; aryl $C_{1-4}$ alkyl; and mono- or di-substituted aryl $C_{1-4}$ alkyl, where the substituents are fluoro, chloro, bromo, iodo or $C_{1-10}$ alkyl, straight or branched chain;

further wherein $R_{58}$ and $R_{59}$ are each independently selected from the group consisting of hydrogen, amino, and mono- or di-substituted amino where the substituents are $C_{1-10}$ alkyl, straight or branched chain $C_{3-8}$ cycloalkyl; provided that $R_{58}$ and $R_{59}$ may not both be amino or substituted amino; and $R_{60}$ is hydrogen, trifluoromethyl; fluoro; chloro; bromo; or iodo; or a pharmaceutically acceptable salt thereof.

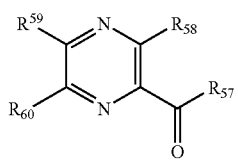

XVIII

In another aspect of the invention, the inhibitor of 3DG function can be a compound such as the amino acid arginine, which reacts irreversibly with 3DG to form a five membered ring called an imidazolone. Once the reaction occurs, 3DG cannot cause crosslinking because the active crosslinker has been removed. Thus, the binding of arginine with 3DG prevents protein crosslinking (see Example 18 and FIG. 12). As described herein, treatment of collagen with 3DG causes the collagen to migrate electrophoretically as if it had a higher molecular weight, which is indicative of crosslinking. However, treatment of a sample of collagen with 3DG in the presence of arginine prevented the appearance of more slowly migrating proteins (Example 18 and FIG. 12). Arginine should be construed to inhibit other alpha-dicarbonyl sugars as well. The invention should be construed to include not just arginine, but it should also be construed to include derivatives and modifications thereof. In one aspect of the invention, arginine may be derivatized or modified to ensure greater efficiency of penetration or passage into the skin or other tissues or to ensure a more efficacious result.

The amino acid arginine has the structure:

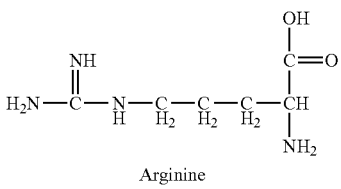

Arginine

In yet another aspect of the invention, the inhibitor of 3DG or other alpha-dicarbonyl sugar function may be L-cysteine or a derivative such as an α-amino-β,β-mercapto-β,β-dimethyl-ethane, or a derivative or modification thereof. Members of the α-amino-β,β-mercapto-β,β-dimethyl-ethane family include, but are not limited to, compounds such as D-penicillamine, L-penicillamine, and D,L-penicillamine (see Jacobson et al., WO 01/78718). The functions inhibited include, but are not limited to, the various functions described herein, such as inhibiting crosslinking of proteins and other molecules, as well as other functions which cause damage to molecules such as proteins, lipid and DNA. For example, damage to lipids may include lipid peroxidation and damage to DNA may include damage such as mutagenesis.

In one aspect of the invention, an α-amino-β,β-mercapto-β,β-dimethyl-ethane may be derivatized or modified to ensure greater efficiency of penetration or passage into the skin or other tissues or to ensure greater efficiency in inhibiting the desired function of 3DG and other alpha-dicarbonyl sugars.

For example, the α-amino-β,β-mercapto-β,β-dimethyl-ethane derivative, D-penicillamine, has the structure:

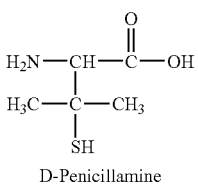

D-Penicillamine

It should be understood that the compounds described herein are not the only compounds capable of inhibiting 3DG function or of treating a 3DG associated skin disease or disorder or diseases and disorders of other tissues and cells. It will be recognized by one of skill in the art that the various embodiments of the invention as described herein related to inhibition of 3DG function, also encompass other methods and compounds useful for inhibiting 3DG function. It will also be recognized by one of skill in the art that other compounds and techniques can be used to practice the invention. The invention should be construed to include compounds and methods useful not merely for the their ability to inhibit 3DG function and to treat a 3DG associated skin disease or disorder, but should be construed to also include the ability to inhibit the function of other members of the alpha-dicarbonyl sugar family of compounds, including glyoxal, methyl glyoxal and glucosone. The invention should also be construed to include treating 3DG associated diseases and disorders other than those of skin, such as 3DG associated diseases and disorders of the gums.

Methods of Identifying Compounds Which Inhibit 3DG and Other Alpha-dicarbonyl Sugar Synthesis, Production, Accumulation, and Function The invention includes various methods for the identification of additional compounds that are useful as 3DG inhibitors. Such methods include the use of test compounds in screening assays that are designed to measure the effects of the test compounds on 3DG synthesis, production, formation, accumulation, function and detoxification. 3DG synthesis, production, formation, accumulation, function and detoxification may be measured in the various assays described herein, and thus the effect of a test compound on 3DG synthesis, production, formation, accumulation, function and detoxification may also be measured in these assays. Similarly, the ability of a test compound to affect the synthesis, production, formation, accumulation, function, and detoxification of other alpha-dicarbonyl sugars may be measured as well.

In one aspect, the method used for screening a potential inhibitor of 3DG synthesis includes the use of one or more assays for measuring fructosamine kinase/amadorase activity or amadorase mRNA levels (see Examples 17, 21, and 22). In another aspect, such an assay utilizes $^{31}$P NMR analysis to measure the conversion of FL3P to 3DG and FL (see Example 3). In yet another aspect, the method used for screening an inhibitor of 3DG synthesis includes a method for measuring the levels of 3DG in a sample or for measuring its degradation product, 3DF, in a sample. For example, 3DG obtained in a sample such as urine, saliva, plasma, blood, tissue, sweat, or cells can be measured using gas chromatography-mass spectroscopy and 3DF can be measured using HPLC, as described herein (see Examples 5, 14, and 15). FL can also be measured using HPLC. Assays to determine the levels of the various components described above can be performed on cells, tissues, blood, plasma, sweat, saliva, and urine samples obtained from an animal, preferably a human. In yet another embodiment, the invention includes the identification of compounds, including, but not limited to, small molecules, drugs or other agents, for their ability to disrupt 3DG function or the interactions of 3DG with other molecules to cause the formation of crosslinked proteins. One assay is based on the ability of 3DG to induce the formation of crosslinked proteins. The invention should be construed to include crosslinking of molecules such as collagen, elastin, and proteoglycans. In one aspect, the invention also includes the identification of compounds based on their ability to disrupt the function of other members of the alpha-dicarbonyl sugar family of compounds, including glyoxal, methyl glyoxal, and glucosone.

In one embodiment, the invention includes identification of compounds which inhibit a component of an enzymatic pathway of 3DG synthesis. Such compounds include those of structural formula XIX. In one aspect, the invention includes a method of identifying a compound which inhibits 3DG synthesis in the skin of a mammal. Such a method may comprise administering a test compound to said mammal and comparing the level of 3DG synthesis in the skin of said mammal with the level of 3DG synthesis in the skin of an otherwise identical mammal which was not administered said test compound. A lower level of 3DG synthesis in the animal administered said test compound is an indication that said test compound inhibits 3DG synthesis. Preferably, a test compound inhibits 3DG synthesis by at least 20% compared to a control group which receives no test compound. More preferably, a test compound inhibits 3DG synthesis by at least 50%.

In another embodiment, the invention includes the identification of compounds which bind to 3DG or directly block its ability to cause the formation of advanced glycation end product modified proteins and crosslinked proteins, such as those compounds comprising the structural formulas I-XVIII.

In yet another embodiment, the invention includes the identification of compounds which inhibit a nonenzymatic pathway of 3DG synthesis.

In another embodiment of the invention, the invention includes the identification of compounds which inhibit accumulation and function of members of the alpha-dicarbonyl sugar family of compounds, including glyoxal, methyl glyoxal and glucosone. In yet another aspect of the invention, the invention includes the identification of compounds which inhibit an enzymatic pathway of alpha-dicarbonyl sugar synthesis.

In general, methods for the identification of a compound which effects the synthesis, production, accumulation or function of 3DG (or other alpha-dicarbonyl sugars), include the following general steps:

The test compound is administered to a cell, tissue, sample, or subject, in which the measurements are to be taken. A control is a cell, tissue, sample, or subject in which the test compound has not been added. A higher or lower level of the indicator or parameter being tested, i.e., 3DG levels, synthesis, function, degradation, etc., in the presence of the test compound, compared with the levels of the indicator or parameter in the sample which was not treated with the test compound, is an indication that the test compound has an effect on the indicator or parameter being measured, and as such, is a candidate for inhibition of the desired activity. Test compounds may be added at varying doses and frequencies to determine the effective amount of the compound which should be used and effective intervals in which it should be administered. In another aspect, a derivative or modification of the test compound may be used.

In one aspect of the invention the 3DG function inhibitor inhibits protein crosslinking. In another aspect, the inhibitor inhibits formation of advanced glycation end product modified proteins. In yet another aspect, the 3DG function inhibitor comprises a structure of one of structural formulas I-XIX or is arginine or a derivative or modification thereof.

In one embodiment, the inhibitor comprises from about 0.0001% to about 15% by weight of the pharmaceutical composition. In one aspect, the inhibitor is administered as a controlled-release formulation. In another aspect the pharmaceutical composition comprises a lotion, a cream, a gel, a liniment, an ointment, a paste, a toothpaste, a mouthwash, an oral rinse, a coating, a solution, a powder, and a suspension. In yet another aspect, the composition further comprises a moisturizer, a humectant, a demulcent, oil, water, an emulsifier, a thickener, a thinner, a surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

The invention should be construed to include various methods of administration, including topical, oral, intramuscular, and intravenous.

Assays for Testing Inhibition of 3DG and Other Alpha-dicarbonyl Sugar Synthesis, Formation, Accumulation, and Function The present disclosure provides a series of assays for identifying inhibitors of 3DG synthesis, formation, accumulation, and function, as well as measuring the effects of the various inhibitors on 3DG synthesis, formation, accumulation, and function. The assays also include those used to measure 3DG degradation, detoxification, and clearance. The assays of the invention include, but are not limited to, HPLC assays, electrophoretic assays, gas chromatographic-mass spectroscopic assays, amino acid analysis, enzyme activity assays, advanced glycation assays, protein crosslinking assays, NMR analysis, ion exchange chromatography, various chemical analyses, various labeling techniques, surgical and gross dissection techniques, RNA isolation, RT-PCR, histologic techniques, various chemical, biochemical, and molecular synthesis techniques, teratogenicity, mutagenicity, and carcinogenicity assays, urine assays, excretion assays, and a variety of animal, tissue, blood, plasma, cell, biochemical, and molecular techniques. Synthetic techniques may be used to produce compounds, such as: chemical and enzymatic production of FL3P (Examples 1, 2 and 3); polyollysine (Example 4); 3-O-methylsorbitol lysine (Example 8); fructosyl spermine (Example 9); and glycated protein diet (Example 13). Other techniques may be used which are not described herein, but are known to those of skill in the art.

In one embodiment of the invention, standards may be used when testing new agents or compounds or when measuring the various parameters described herein. For example, fructose-lysine is a known modulator of 3DG and 3DF and it can be administered to a group or subject as a standard or control against which the effects of a test agent or compound can be compared. In addition, when measuring a parameter, measurement of a standard can include measuring parameters such as 3DG or 3DF concentrations in a tissue or fluid obtained from a subject before the subject is treated with a test compound and the same parameters can be measured after treatment with the test compound. In another aspect of the invention, a standard can be an exogenously added standard which is an agent or compound that is added to a sample and is useful as an internal control, especially where a sample is processed through several steps or procedures and the amount of recovery of a marker of interest at each step must be determined. Such exogenously added internal standards are often added in a labeled form, i.e., a radioactive isotope.

Methods for Diagnosing 3DG Associated Skin Diseases or Disorders

The present invention discloses the presence of 3DG in skin and methods for measuring 3DG levels in the skin and for measuring an enzyme responsible for 3DG synthesis in the skin (see Examples 19 and 20). The invention also encompasses methods which may be used to diagnose changes in 3DG levels in the skin which may be associated with wrinkling, aging, or various other skin diseases or disorders. The invention should not be construed to include only methods for diagnosing 3DG associated skin diseases and disorders, but should be construed to include methods for diagnosing skin diseases and disorders associated with other alpha-dicarbonyl sugars as well. The invention should also be construed to include methods for diagnosing 3DG associated diseases or disorders of other cells and tissues as well, including, but not limited to, gum diseases and disorders.

In one embodiment of the invention, a patient with skin wrinkling, skin aging, or another skin disease or disorder, may be subjected to a diagnostic test to determine, for example, the levels of 3DG, the functional activity of 3DG, the levels of 3DF, a 3DF/3DG ratio, the amount of amadorase protein or mRNA present, or the levels of amadorase activity in their skin. Such a test is based on the various methods and assays described herein, or known to those of skill in the art. A higher level of 3DG or amadorase, or their activities, or lower levels of 3DF, compared to a non-affected area of skin or to skin of a normal patient, would be an indication that the skin wrinkling, skin aging, or other skin disease or disorder, is associated with 3DG and that a 3DG inhibitor of the present invention would be an appropriate treatment for the problem. The invention should also be construed to include skin diseases and disorders associated with molecules of the alpha-dicarbonyl sugar family other than 3DG.

In one aspect of the invention, additional markers of 3DG associated skin diseases or disorders can be measured, including, but not limited to, measuring 3DF and FL levels, crosslinked protein levels, as well as levels of other alpha-dicarbonyl sugars such as glyoxal, methyl glyoxal, and glucosone.

A multitude of assays for measuring 3DG levels and function, including measuring its precursors, are described throughout the present disclosure (see Examples 1-22). However, the invention should not be construed to include only the assays described herein, but should be construed to include other assays to measure 3DG levels or function, including assays or techniques which are indirect measures of 3DG levels or functional activity. For example, in one aspect of the invention, indirect measurement of 3DG levels and function can be determined by measuring such things as levels of 3DF, protein crosslinking, proteoglycan crosslinking, or any other assay shown to be correlative of 3DG levels.

In one aspect of the invention, the sample to be used for measuring 3DG levels, etc., is a skin sample. Skin samples may be obtained by methods which include, but are not limited to, punch biopsies, scraping, and blistering techniques.

In another aspect of the invention, indirect assays for 3DG levels or function in the skin which are correlative of 3DG associated skin diseases or disorders may be used. The assays may include, but are not limited to, assays for measuring 3DG levels or function in other tissues, sweat, blood, plasma, saliva, or urine.

The invention discloses a method for diagnosing a 3DG or other alpha-dicarbonyl sugar associated skin disease or disorder comprising acquiring a biological sample from a test subject and comparing the level of 3DG or other alpha-dicarbonyl sugar associated parameter of wrinkling, aging, disease, or disorder of the skin with the level of the same parameter in an otherwise identical biological sample from a control subject. The control can be from an unaffected area of the same subject or from a subject not affected by a 3DG or other alpha-dicarbonyl sugar associated skin disease or disorder. A higher level of the parameter in the test subject is an indication that the test subject has a 3DG or other alpha-dicarbonyl sugar associated wrinkling, aging, disease, or disorder of the skin. The parameters which can be measured are described herein or are known to those of skill in the art, and include, but are not limited to, 3DG, protein crosslinking, proteoglycan crosslinking, advanced glycation end product modified proteins, 3DF, fructosamine kinase/amadorase levels and activity, and fructosamine kinase/amadorase mRNA.

In yet another aspect of the invention, 3DG or other alpha-dicarbonyl sugars may be associated with skin diseases or disorders selected from the group comprising skin aging, photoaging, skin wrinkling, skin cancer, hyperkeratosis, hyperplasia, acanthosis, papillomatosis, dermatosis, hyperpigmentation, rhinophyma, scleroderma, and rosacea. In another aspect of the invention, 3DG is associated with functions including, but not limited to, protein crosslinking, mutagenicity, teratogenicity, apoptosis, oxidative damage caused by formation of reactive oxygen species, and cytotoxicity. It is understood that 3DG and other alpha-dicarbonyl sugars are associated with functions causing damage to not only proteins, but to lipids and DNA as well. In aspect of the invention, 3DG or other alpha-dicarbonyl sugars may also be associated with diseases and disorders other than skin diseases, including, but not limited to, gum diseases and disorders.

In yet another aspect of the invention, the assays for measuring 3DG levels and function may be used in conjunction with other methods for measuring skin diseases and disorders, such as measuring the thickness or elasticity of the skin. Many of these assays are described herein. One of skill in the art will appreciate that other assays not described herein may be used in conjunction with the 3DG assays to form a complete diagnosis of the type of skin problem involved and whether or not it is a 3DG associated skin problem.

The invention should not be construed to include diagnosing a skin disease, condition or disorder merely by measuring levels of the alpha-dicarbonyl sugar 3DG, it should also be construed to include measuring levels of other members of the alpha-dicarbonyl sugar family as well.

Thus, the use of a diagnostic assay to determine an association between 3DG and a skin disease or disorder will allow the selection of appropriate subjects before initiating treatment with an inhibitor of 3DG.

Methods for Inhibiting or Treating 3DG or Other Alpha-dicarbonyl Sugar Associated Skin Wrinkling Skin Aging, or Other Skin Disease or Disorder The invention also discloses methods for inhibiting or treating 3DG related skin diseases or disorders. Some examples of 3DG associated diseases or disorders include, but are not limited to, skin cancer, psoriasis, aging, wrinkling, hyperkeratosis, hyperplasia, acanthosis, papillomatosis, dermatosis, rhinophyma, and rosacea. A cancer or other disease or disorder may belong to any of a group of cancers or other diseases or disorders, which have been described herein, as well as any other related cancer or other disease or disorder known to those of skill in the art.

The invention should not be construed as being limited solely to these examples, as other 3DG associated diseases or disorders which are at present unknown, once known, may also be treatable using the methods of the invention. One of skill in the art would appreciate that 3DG inhibitors may be used prophylactically for some diseases or disorders of the skin, wherein 3DG is known, or it becomes known, that 3DG is associated with a skin disease or disorder. For example, 3DG inhibitors may be applied to prevent wrinkling or other skin problems in subjects who are exposed to harsh environmental elements such as the sun (photoaging/photodamage), heat, chemicals, or cold. Such problems can be due to damage to proteins or other molecules such as lipids or nucleic acids caused by 3DG or alpha-dicarbonyl sugars.

The invention also includes methods for inhibiting or treating skin diseases or disorders associated with members of the alpha-dicarbonyl sugar family of compounds other than 3DG.

In one aspect of the invention, various changes in the skin can be measured following treatment with inhibitors of 3DG. The skin topography can be defined by parameters such as: (a) number of wrinkles; (b) total area of wrinkles; (c) total length of wrinkles; (d) mean length of wrinkles; and (e) mean depth of wrinkles. The type of wrinkles can be determined on the basis of depth, length, and area. These properties can be used when evaluating the changes in skin due to disease or disorder or the effects of a treatment on the skin. The effects of changes in 3DG levels and function on various skin qualities can be determined based on techniques known in the art. Methods to measure skin quality include, but are not limited to, measuring viscoelastic properties with instruments such as a ballistometer, measuring the mechanical/vertical deformation properties of the skin with an instrument such as a cutometer, or measuring changes in skin capacitance resulting from changes in the degree of hydration using a comeometer.

The invention relates to the administration of an identified compound in a pharmaceutical composition to practice the methods of the invention, the composition comprising the compound or an appropriate derivative or fragment of the compound and a pharmaceutically-acceptable carrier. For example, a chemical composition with which an appropriate inhibitor of enzyme dependent or nonenzyme dependent production of 3DG, or inhibitor of 3DG accumulation or function, or stimulator of 3DG removal, detoxification, or degradation, is combined, is used to administer the appropriate compound to an animal. The invention should be construed to include the use of one, or simultaneous use of more than one, inhibitor of 3DG or stimulator of 3DG removal, degradation, or detoxification. When more than one stimulator or inhibitor is used, they can be administered together or they can be administered separately.

In one embodiment, the pharmaceutical compositions useful for practicing the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 100 g/kg/day.

Pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer compounds according to the methods of the invention.

Compounds which are identified using any of the methods described herein may be formulated and administered to a mammal for treatment of skin aging, skin wrinkling, and various skin related diseases, disorders, or conditions described herein.

The invention encompasses the preparation and use of pharmaceutical compositions comprising a compound useful for treatment of various skin related diseases, disorders, or conditions described herein, including skin aging, photoaging, and wrinkling of the skin. The invention also encompasses 3DG associated diseases and disorders other than those of the skin, including, but not limited to, gum diseases and disorders. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, chelating agents, bleaching agents, tyrosinase inhibitors and other known depigmentation agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically-or naturally-derived.

Liquid derivatives and natural extracts made directly from biological sources may be employed in the compositions of this invention in a concentration (w/v) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound for use in the invention in the aqueous gel formulation. Preferred antioxidants for some compounds are BHT, BHA, alphatocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefor as would be known to those skilled in the art.

Controlled-release preparations may also be used and the methods for the use of such preparations are known to those of skill in the art.

In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, an "oily" liquid is one which comprises a carbon-containing liquid molecule and which exhibits a less polar character than water.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, a paste, a gel, a toothpaste, a mouthwash, a coating, an oral rinse, or an emulsion. The terms oral rinse and mouthwash are used interchangeably herein.

A pharmaceutical composition of the invention may be prepared, packaged, or sold in a formulation suitable for oral or buccal administration. Such a formulation may comprise, but is not limited to, a gel, a liquid, a suspension, a paste, a toothpaste, a mouthwash or oral rinse, and a coating. For example, an oral rinse of the invention may comprise a compound of the invention at about 1.4%, chlorhexidine gluconate (0.12%), ethanol (11.2%), sodium saccharin (0.15%), FD&C Blue No. 1 (0.001%), peppermint oil (0.5%), glycerine (10.0%), Tween 60 (0.3%), and water to 100%. In another embodiment, a toothpaste of the invention may comprise a compound of the invention at about 5.5%, sorbitol, 70% in water (25.0%), sodium saccharin (0.15%), sodium lauryl sulfate (1.75%), carbopol 934, 6% dispersion in (15%), oil of spearmint (1.0%), sodium hydroxide, 50% in water (0.76%), dibasic calcium phosphate dihydrate (45%), and water to 100%. The examples of formulations described herein are not exhaustive and it is understood that the invention includes additional modifications of these and other formulations not described herein, but which are known to those of skill in the art.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which maybe included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

It will be recognized by one of skill in the art that the various embodiments of the invention as described above relating to methods of inhibiting 3DG or treating 3DG related diseases or conditions, includes other diseases and conditions not described herein.

Kits

The present invention should be construed to include kits for inhibiting or stimulating 3DG, treating 3DG associated skin diseases and disorders, kits for measuring 3DG and 3DG related parameters, and kits for diagnosing 3DG associated skin diseases and disorders. The invention should be construed to include kits for alpha-dicarbonyl sugars other than 3DG as well.

The invention includes a kit comprising an inhibitor of 3DG or a compound identified in the invention, a standard, and an instructional material which describes administering the inhibitor or a composition comprising the inhibitor or compound to a cell or an animal. This should be construed to include other embodiments of kits that are known to those skilled in the art, such as a kit comprising a standard and a (preferably sterile) solvent suitable for dissolving or suspending the composition of the invention prior to administering the compound to a cell or an animal. Preferably the animal is a mammal. More preferably, the mammal is a human.

The invention also includes a kit comprising a stimulator of 3DG degradation, detoxification, or clearance, or a such a stimulatory compound identified in the invention, a standard, and an instructional material which describes administering the stimulator or a composition comprising the stimulator or compound to a cell or an animal. This should be construed to include other embodiments of kits that are known to those skilled in the art, such as a kit comprising a standard and a (preferably sterile) solvent suitable for dissolving or suspending the composition of the invention prior to administering the compound to a cell or an animal.

In accordance with the present invention, as described above or as discussed in the Examples below, there can be employed conventional chemical, cellular, histochemical, biochemical, molecular biology, microbiology and recombinant DNA techniques which are known to those of skill in the art. Such techniques are explained fully in the literature. See for example, Sambrook et al., 1989 Molecular Cloning—a Laboratory Manual, Cold Spring Harbor Press; Glover, (1985) DNA Cloning: a Practical Approach; Gait, (1984) Oligonucleotide Synthesis; Harlow et al., 1988 Antibodies—a Laboratory Manual, Cold Spring Harbor Press; Roe et al., 1996 DNA Isolation and Sequencing: Essential Techniques, John Wiley; and Ausubel et al., 1995 Current Protocols in Molecular Biology, Greene Publishing.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Isolation and Identification of FL3P:

The following assays were performed in order to verify that fructoselysine (FL) could be identified in its phosphorylated state, e.g., FL3P. A $^{31}$P NMR analysis of a perchloric acid extract of diabetic rat kidneys was performed and showed a new sugar monophosphate resonance at 6.24 ppm which is not observed in non-kidney tissue and is present at greatly reduced levels in non-diabetic kidney. The compound responsible for the observed resonance was isolated by chromatography of the extract on a microcrystalline cellulose column using 1-butanol-acetic acid-water (5:2:3) as eluent. The structure was determined by proton 2D COSY to be fructoselysine 3-phosphate. This was later confirmed by injecting animals with FL, prepared as previously described (Finot and Mauson, 1969, Helv. Chim. Acta, 52:1488), and showing direct phosphorylation to FL3P.

Using FL specifically deuterated in position-3 confirmed the position of the phosphate at carbon-3. This was performed by analyzing the $^{31}$P NMR spectra, both coupled and decoupled. The normal P—O—C—H coupling produces a doublet in FL3P with a J value of 10.3 Hz; whereas P—O—

C-D has no coupling and produces a singlet both coupled and decoupled, as was found for 3-deuterated FL3P. A unique property of FL3P is that when treated with sodium borohydride it is converted into two new resonances at 5.85 and 5.95 ppm, which correspond to mannitol and sorbitol-lysine 3-phosphates.

Example 2

Synthesis of FL3P:

1 mmol of dibenzyl-glucose 3-phosphate and 0.25 mmol of α-carbobenzoxy-lysine was refluxed in 50 ml of MeOH for 3 hours. The solution was diluted with 100 ml water and chromatographed on a Dow-50 column (2.5×20 cm) in the pyridinium form and eluted first with water (200 ml) and then with 600 ml buffer (0.1M pyridine and 0.3M acetic acid). The target compound eluted at the end of the water wash and the beginning of the buffer wash. The results demonstrated that removal of the cbz and benzyl blocking groups with 5% Pd/C at 20 psi of hydrogen gave FL3P in 6% yield.

Example 3

Enzymatic Production of FL3P from FL and ATP and Assay for Screening Inhibitors:

Initially $^{31}$P NMR was used to demonstrate kinase activity in the kidney cortex. A 3 g sample of fresh pig kidney cortex was homogenized in 9 ml of 50 mM Tris.HCl containing 150 mM KCl, 5 mM DTT, 15 mM $MgCl_2$, pH 7.5. This was centrifuged at 10,000 g for 30 minutes, and then the supernatant was centrifuged at 100,000 g for 60 minutes. Ammonium sulfate was added to 60% saturation. After 1 hour at 4° C. the precipitate was collected by centrifugation and dissolved in 5 ml. of original buffer. A 2 ml aliquot of this solution was incubated with 10 mM ATP and 10 mM of FL (prepared as in Example 1, above) for 2 hours at 37° C. The reaction was quenched with 300 μl of perchloric acid, centrifuged to remove protein, and desalted on a column of Sephadex G 10 (5×10 cm). $^{31}$P NMR analysis of the reaction mixture detected formation of FL3P.

Based on the proof of kinase activity thus obtained, a radioactive assay was developed. This assay was designed to take advantage of the binding to Dow-50 cation exchange resin by FL3P. This characteristic of FL3P was discovered during efforts to isolate it. Since most phosphates do not bind to this resin, it was suspected that the bulk of all compounds that react with ATP as well as any excess ATP would not be bound. The first step was to determine the amount of resin required to remove the ATP in the assay. This was accomplished by pipetting the mixture into a suspension of 200 mg of Dow-1 in 0.9 ml $H_2O$, vortexing, and centrifuging to pack the resin. From this 0.8 ml of supernatant was pipetted onto 200 mg of fresh dry resin, vortexed and centrifuged. A 0.5 ml volume of supernatant was pipetted into 10 ml of Ecoscint A and counted. Residual counts were 85 cpm. This procedure was used for the assay. The precipitate from 60% ammonium sulfate precipitation of the crude cortex homogenate was redissolved in the homogenate buffer at 4° C. The assay contains 10 mM $\gamma^{33}$P-ATP (40,000 cpm), 10 mM FL, 150 mM KCl, 15 mM $MgCl_2$, 5 mM DTT in 0.1 ml of 50 mM Tris.HCl, pH 7.5. The relationship between rates of FL3P production and enzyme concentration was determined using triplicate determinations with 1, 2, and 4 mg of protein for 30 minutes at 37° C. Blanks run concurrently without FL were subtracted and the data recorded. The observed activity corresponds to an approximate FL3P synthesis rate of 20 mmols/hr/mg protein.

Example 4

Inhibition of the Formation of 3-deoxyglucosone by Meglumine and Various Polyollysines:

a. General Polyollysine Synthesis:

The sugar (11 mmoles), α-carbobenzoxy-lysine (10 mmols) and $NaBH_3CN$ (15 mmoles) were dissolved in 50 ml of MeOH—$H_2O$ (3:2) and stirred at 25° C. for 18 hours. The solution was treated with an excess of Dow-50 (H) ion exchange resin to decompose excess $NaBH_3CN$. This mixture (liquid plus resin) was transferred onto a Dow-50 (H) column (2.5×15 cm) and washed well with water to remove excess sugar and boric acid. The carbobenzoxy-polyollysine was eluted with 5% $NH_4OH$. The residue obtained upon evaporation was dissolved in water-methanol (9:1) and reduced with hydrogen gas (20 psi) using a 10% palladium on charcoal catalyst. Filtration and evaporation yields the polyollysine.

b. Experimental Protocol for Reduction of Urinary and Plasma 3-deoxyglucosone by Sorbitollysine, Mannitollysine and Galactitollysine:

Urine was collected from six rats for three hours. A plasma sample was also obtained. The animals were then given 10 μmols of either sorbitollysine, mannitollysine, or galactitollysine by intraperitoneal injection. Urine was collected for another three hours, and a plasma sample obtained at the end of the three hours.

a. 3-deoxyglucosone was measured in the samples, as described in Example 5, below, and variable volumes were normalized to creatinine. The average reduction of urinary 3-deoxyglucosone was 50% by sorbitollysine, 35% by mannitollysine and 35% by galactitollysine. Plasma 3-deoxyglucosone was reduced 40% by sorbitollysine, 58% by mannitollysine and 50% by galactitollysine.

b. Use of Meglumine to Reduce Urinary 3-deoxyglucosone:

Three rats were treated as in b), immediately above, except meglumine (100 μmols) was injected intraperitoneally instead of the above-mentioned lysine derivatives. Three hours after the injection the average 3-deoxyglucosone concentrations in the urine were decreased 42%.

Example 5

Elevation of Urinary FL, 3DG and 3DF in Humans Following Ingestion of Glycated Protein:

a. Preparation of Glycated Protein Containing Food Product:

260 g of casein, 120 g of glucose and 720 ml of water were mixed to give a homogeneous mixture. This mixture was transferred to a metal plate and heated at 65° C. for 68 hours. The resulting cake was then pulverized to a coarse powder.

This powder contained 60% protein as determined by the Kjeldahl procedure.

b. Measurement of Glycated Lysine Content:

One gram of the powder prepared as in step a., above, was hydrolyzed by refluxing with 6N HCl for 20 hours. The resulting solution was adjusted to pH 1.8 with NaOH solution and diluted to 100 ml. The fructoselysine content was measured on an amino acid analyzer as furosine, the product obtained from acid hydrolysis of fructoselysine. In this way, it was determined that the cake contained 5.5% (w/w) fructoselysine.

c. Experimental Protocol:

Volunteers spent two days on a fructoselysine-free diet and then consumed 22.5 g of the food product prepared as described herein, thus effectively receiving a 2 gram dose of fructoselysine. Urine was collected at 2 hour intervals for 14 hours and a final collection was made at 24 hours.

d. Measurement of FL, 3DG and 3DF in Urine:

FL was measured by HPLC with a Waters 996 diode Array using a Waters C18 Free Amino Acid column at 46° C. and a gradient elution system of acetonitrile-methyl alcohol-water (45:15:40) into acetonitrile-sodium acetate-water (6:2:92) at 1 ml/min. Quantitation employed an internal standard of meglumine.

3DF was measured by HPLC after deionization of the sample. Analyses were performed on a Dionex DX-500 HPLC system employing a PA1 column (Dionex) and eluting with 32 mM sodium hydroxide at 1 ml/min. Quantitation was performed from standard curves obtained daily with synthetic 3DF.

3DG was measured by GC-MS after deionization of the sample. 3DG was derivatized with a 10-fold excess of diaminonaphthalene in PBS. Ethyl acetate extraction gave a salt free fraction which was converted to the trimethyl silyl ethers with Tri-Sil (Pierce). Analysis was performed on a Hewlett-Packard 5890 selected ion monitoring GC-MS system. GC was performed on a fused silica capillary column (DB-5,25 mx.25 mm) using the following temperature program: injector port 250° C., initial column temperature 150° C. which is held for 1 minute, then increased to 290° C. at 16° C./minute and held for 15 minutes. Quantitation of 3DG employed selected ion monitoring using an internal standard of U-13C-3DG.

The results of the experiments described in this example are now presented.

Figure 3:
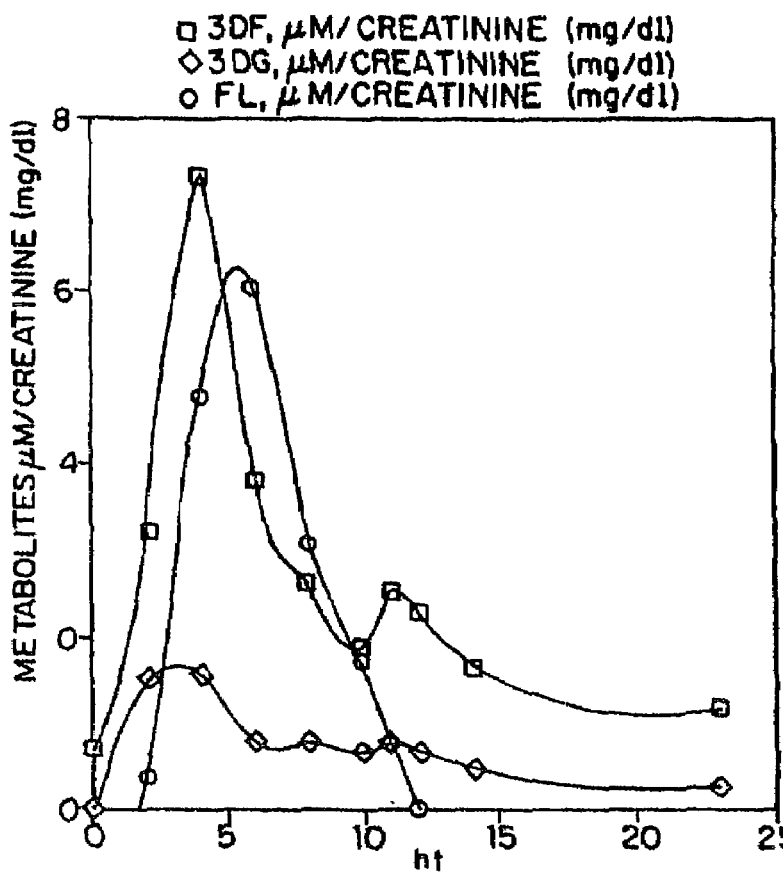
FIG. 3 is a graph representing a urinary profile showing the variation over time of 3DF, 3DG and FL from a single individual fed 2 grams of FL and followed for 24 hours (Brown et al., U.S. Pat. No. 6,004,958).

The graph depicted in FIG. 3 represents production of FL, 3DF, and 3DG in the urine of one volunteer after consuming the glycated protein. The rapid appearance of all three metabolites is clearly evident. Both 3DF and 3DG show a slight elevation even after twenty-four hours.

Figure 4:
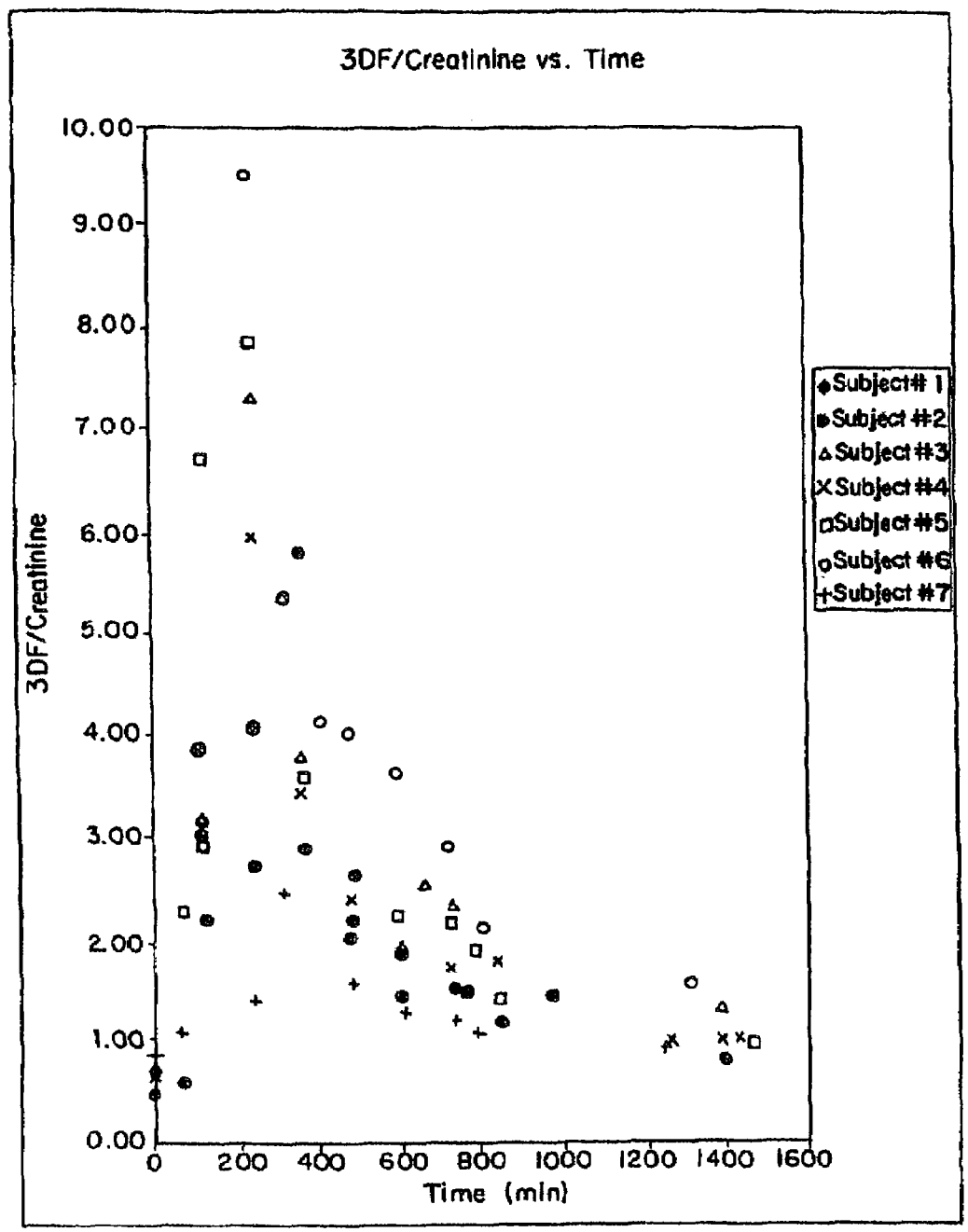
FIG. 4 is a graph representing 3DF excretion in urine over time from seven volunteers fed 2 grams of fructoselysine (Brown et al., U.S. Pat. No. 6,004,958).

The graph shown in FIG. 4 represents the formation of 3DF in each of the members of a seven-person test group. A similar pattern was seen in all cases. As demonstrated in FIG. 4, 3DF excretion peaks about 4 hours after the FL bolus and a slight elevation of 3DF is noticeable even 24 h after the bolus.

Example 6

Effects of Increased Dietary Uptake of Glycated Proteins:

N-acetyl-β-glucosamimidase (NAGase) is an enzyme excreted into the urine in elevated concentration in diabetics. It is thought to be an early marker of tubular damage, but the pathogenesis of increased NAGase in urine is not well understood. The increased urinary output of NAGase in diabetics has been proposed to be due to activation of lysosomes in proximal tubules induced by diabetes with an increased output into the urine rather than destruction of cells.

Figure 5:
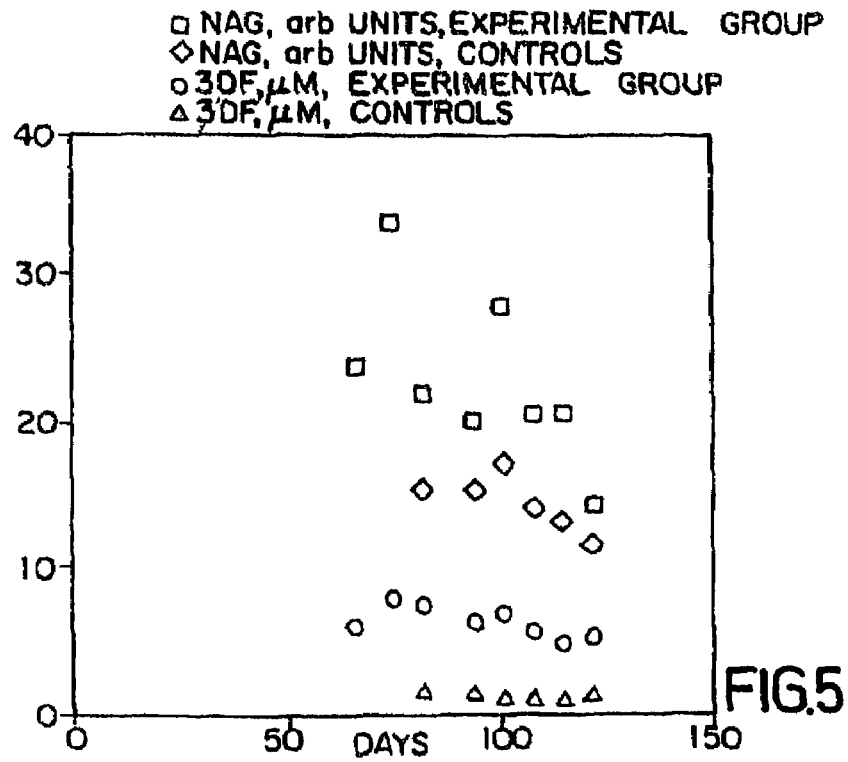
FIG. 5 graphically compares 3DF and N-acetyl-β-glucosamimidase (NAG) levels in control animals and an experimental group maintained on feed containing 0.3% glycated protein (Brown et al., U.S. Pat. No. 6,004,958).

Rats were fed a diet containing 0.3% glycated protein or control feed over several months. The urinary output of NAGase and 3DF were determined at various times, as indicated in FIG. 5. The amount of 3DG excreted in urine was also determined.

Figure 6:
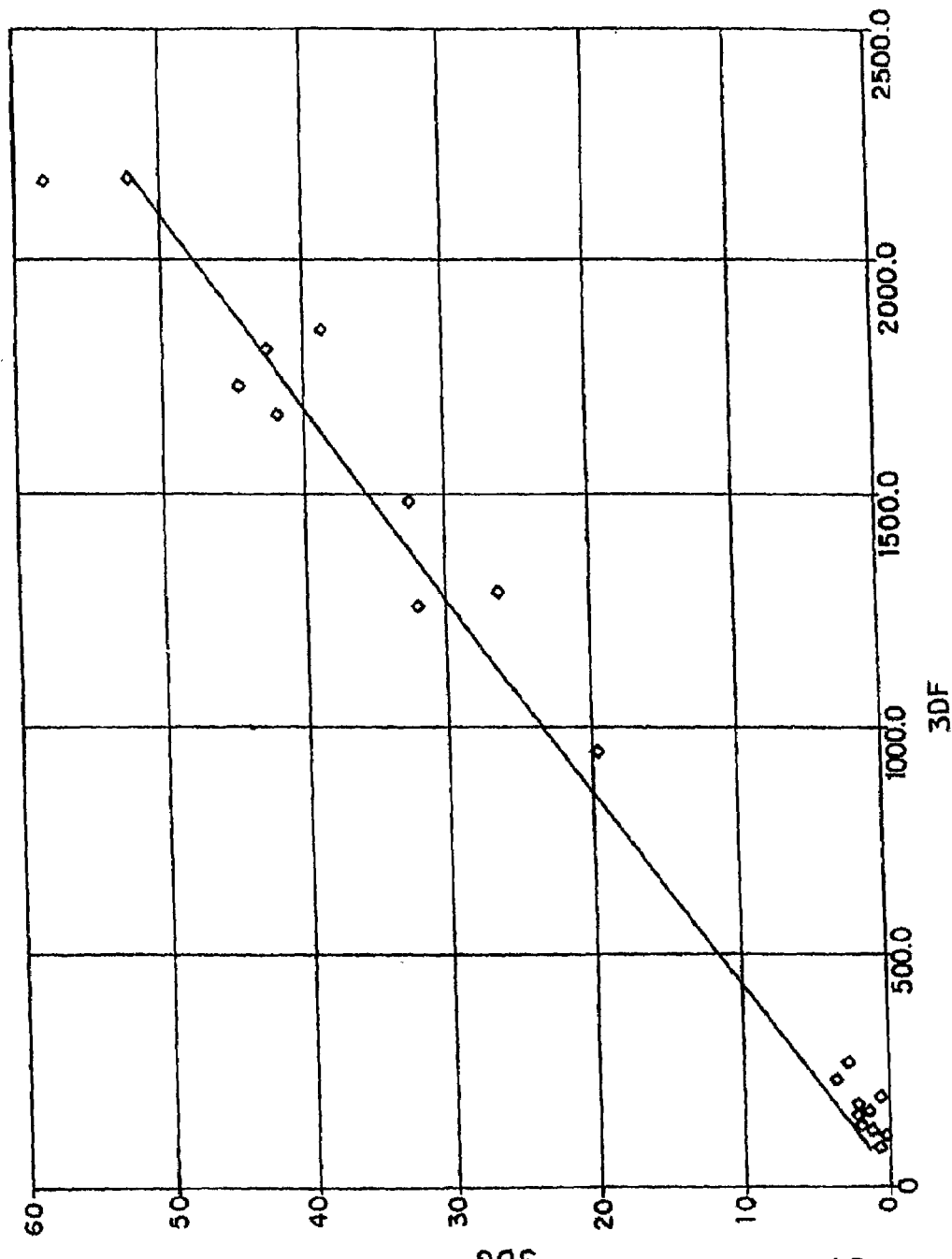
FIG. 6 is a graph which demonstrates the linear relationship between 3DF and 3DG levels in urine of rats fed either a control diet or a diet enriched in glycated protein (Brown et al., U.S. Pat. No. 6,004,958).
Figure 7A:
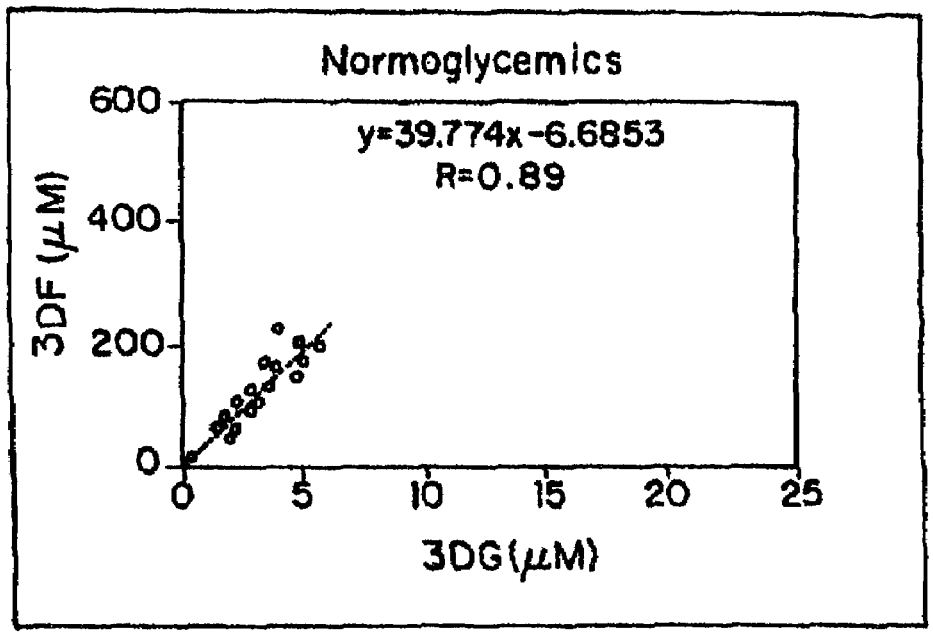
FIG. 7, comprising FIG. 7A and FIG. 7B, graphically depicts fasting levels of urinary 3DG in normal subjects and in diabetic patients, plotted against the fasting level of 3DF (Brown et al., U.S. Pat. No. 6,004,958).
Figure 7B:
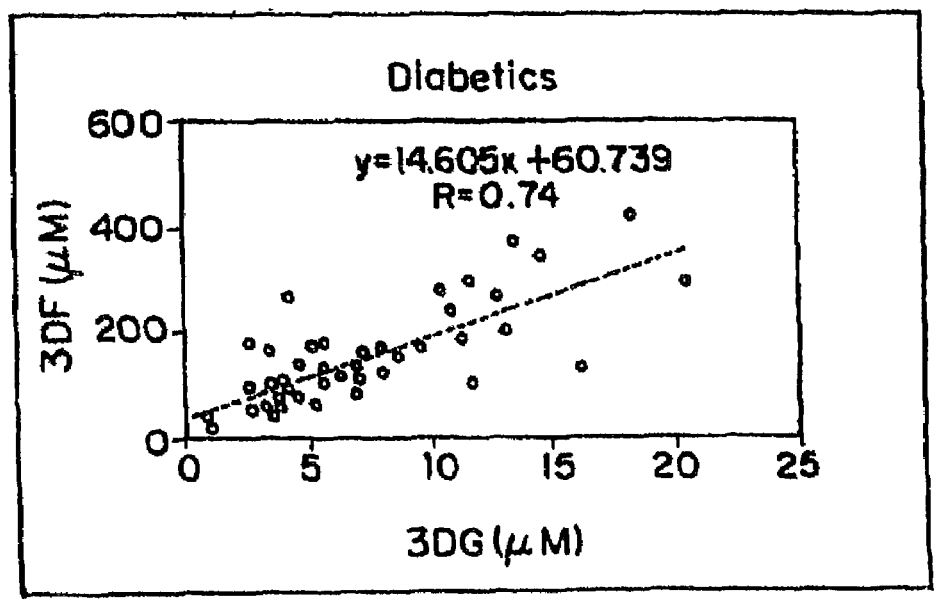
Figure 8A:
FIG. 8A and FIG. 8B, depicts images of photomicrographs illustrating the effects of a diet containing high levels of glycated protein on the kidney. Periodic acid and Schiff (PAS) stained kidney sections were prepared from a rat fed a diet enriched in mildly glycated protein (FIG. 8A) and a rat fed a normal diet (FIG. 8B). In this experiment, non-diabetic rats were fed a diet containing 3% glycated protein for 8 months. This diet substantially elevated levels of FL and its metabolites (>3-fold in the kidney).
Figure 8B:
Figure 9:
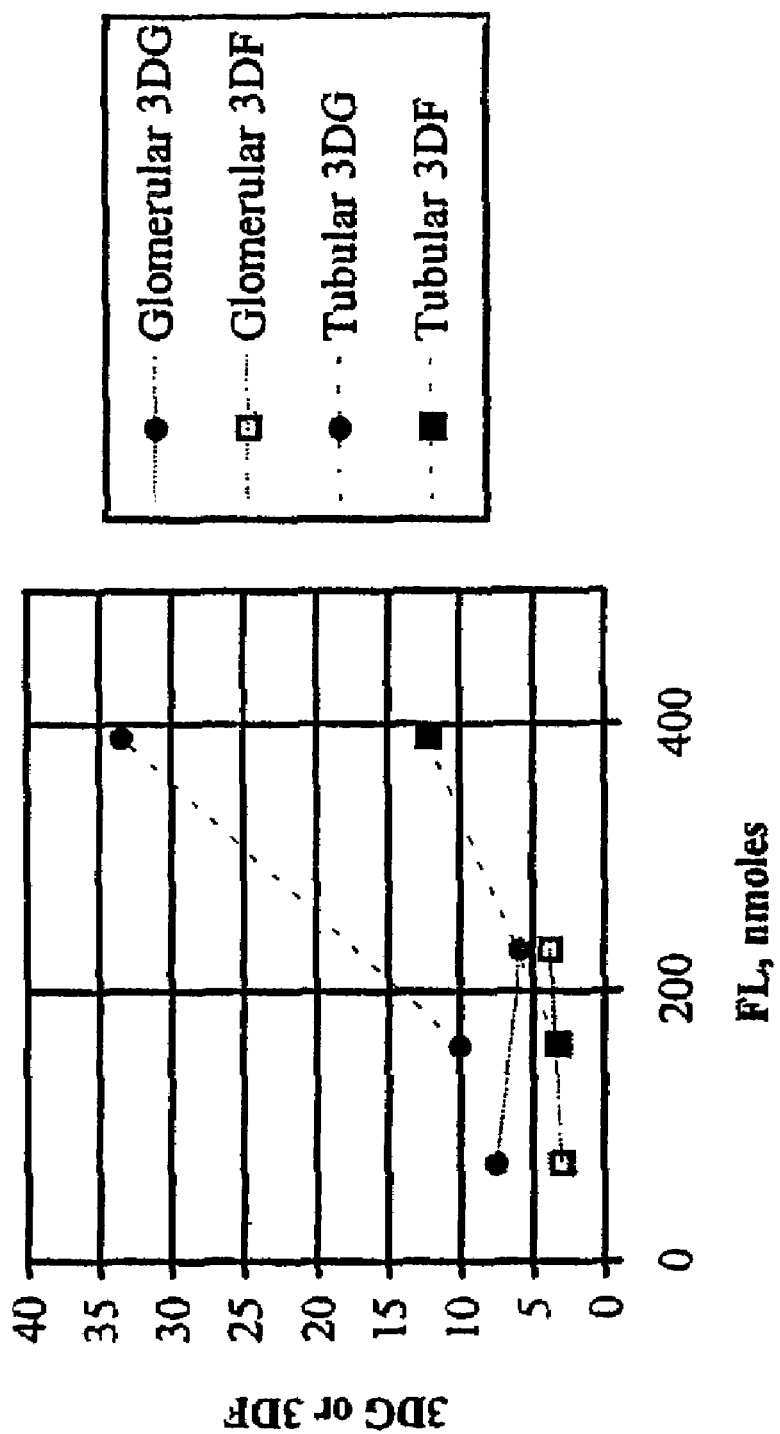
FIG. 9 is a graphic comparison of 3DG and 3DF levels in glomerular and tubular fractions from rat kidneys after FL feeding.

The results obtained in this example demonstrate that in all comparisons 3DF and NAGase levels are elevated in the experimental group relative to the control. Thus, animals fed glycated protein excrete excess NAGase into their urine, similar to results obtained with diabetics. NAGase output increased by approximately 50% in the experimental group, compared with control animals. The experimental animals also had a five-fold increase in urine 3DF compared with controls. Urinary 3DF was found to correlate extremely well with 3DG, as can be seen in FIGS. 5 and 6.

Example 7

Electrophoretic Analysis of Kidney Proteins:

Two rats were injected daily with 5 μmols of either FL or mannitol (used as a control) for 5 days. The animals were sacrificed and the kidneys removed and dissected into the cortex and medulla. Tissues were homogenized in 5 volumes of 50 mM Tris.HCl containing 150 mM KCl, 15 mM $MgCl_2$ and 5 mM DTT, pH 7.5. Cellular debris was removed by centrifugation at 10,000×g for 15 minutes, and the supernatant was then centrifuged at 150,000×g for 70 minutes. The soluble proteins were analyzed by SDS PAGE on 12% polyacrylamide gels as well as on 4-15 and 10-20% gradient gels.

It was found that in all cases, lower molecular weight bands were missing or visually reduced from the kidney extract of the animal injected with FL when compared with the animal injected with mannitol.

Example 8

Synthesis of 3-O-methylsorbitollysine (Structure XIX)

3-OMe glucose (25 grams, 129 mmol) and α-Cbz-lysine (12 grams, 43 mmol) were dissolved in 200 ml of water-methanol (2:1). Sodium cyanoborohydride (10 grams, 162 mmol) was added and the reaction stirred for 18 days at room temperature. Reaction of α-Cbz-lysine was monitored by thin layer chromatography on silica gel employing 1-butanol-acetic acid-water (4:1:1) using ninhydrin for visualization. The reaction was complete when no α-Cbz-lysine remained. The solution was adjusted to pH 2 with HCl to decompose excess cyanoborohydride, neutralized and then applied to a column (5×50 cm) of Dowex-50 (H+) and the column washed well with water to remove excess 3-O-me-glucose. The target compound was eluted with 5% ammonium hydroxide. After evaporation the residue was dissolved in 50 ml of water-methanol (2:1) and 10% Pd/C (0.5 gram) was added. The mixture was shaken under 20 psi of hydrogen for 1 hr. The charcoal was filtered off and the filtrate evaporated to a white powder (10.7 gram, 77% yield based on α-Cbz-lysine) that was homogeneous when analyzed by reversed phase HPLC as the phenylisothiocyanate derivative. Elemental analysis: Calculated for $C_{13}H_{28}N_2O_7 CH_3OH\ 2\ H_2O$ C, 42.86; H, 9.18; N, 7.14. Found: C, 42.94; H, 8.50; N, 6.95.

Other specific compounds having the structure of formula (XIX), above, may be made, e.g., by glycation of a selected nitrogen- or oxygen-containing starting material, which may be an amino acid, polyaminoacid, peptide or the like, with a glycating agent, such as fructose, which may be chemically modified, if desired, according to procedures well know to those skilled in the art.

Example 9

Additional Assay for FL3P Kinase Activity:

a. Preparation of Stock Solutions:

An assay buffer solution was prepared which was 100 mM HEPES pH 8.0, 10 mM ATP, 2 mM $MgCl_2$, 5 mM DTT, 0.5 mM PMSF. A fructosyl-spermine stock solution was prepared which was 2 mM fructosyl-spermine HCl. A spermine control solution was prepared which was 2 mM spermine HCl.

b. Synthesis of Fructosyl-Spermine:

Synthesis of fructosyl-spermine was performed by an adaptation of a known procedure (J. Hodge and B. Fisher, 1963, Methods Carbohydr. Chem., 2:99-107). A mixture of spermine (500 mg), glucose (500 mg), and sodium pyrosulfite (80 mg) was prepared in a molar ratio of 8:4:1 (spermine:glucose:pyrosulfite) in 50 ml of methanol-water (1:1) and refluxed for 12 hours. The product was diluted to 200 ml with water and loaded onto a DOW-50 column (5×90 cm). The unreacted glucose was removed by 2 column volumes of water and the product and unreacted spermine were removed with 0.1 M $NH_4OH$. Pooled peak fractions of the product were lyophilized and concentration of fructosyl-spermine was determined by measuring the integral of the C-2 fructosyl peak in a quantitative $^{13}C$ NMR spectrum of the product (NMR data collected with a 45° pulse, a 10 second relaxation delay and without NOE decoupling).

c. Kinase Assay to Determine Purification:

An incubation mixture was prepared including 10 μl of the enzyme preparation, 10 μl of assay buffer, 1.0 μCi of $^{33}P$ ATP, 10 μl of fructosyl-spermine stock solution and 70 μl of water and incubated at 37° C. for 1 hour. At the end of the incubation 90 μl (2×45 μl) of the sample was spotted onto two 2.5 cm diameter cellulose phosphate disks (Whatman P-81) and allowed to dry. The disks were washed extensively with water. After drying, the disks were placed in scintillation vials and counted.

Each enzyme fraction was assayed in duplicate with an appropriate spermine control.

Example 10

Kidney Pathology Observed in Test Animals on Glycated Protein Diet:

Three rats were maintained on a glycated protein diet (20% total protein; 3% glycated) for 8 months and compared to 9 rats of the same age maintained on a control diet. The glycated protein diet consisted of a standard nutritious diet to which 3% glycated protein had been substituted for nonglycated protein. The glycated protein was made by mixing together casein and glucose (2:1), adding water (2×the weight of the dried material), and baking the mixture at 60° C. for 72 hours. The control was prepared in the same way except that no water was used and the casein and glucose were not mixed prior to baking.

The primary finding was a substantial increase in damaged glomeruli in the animals on the glycated diet. Typical lesions observed in these animals were segmental sclerosis of the glomerular tuft with adhesion to Bowman's capsule, tubular metaplasia of the parietal epithelium and interstitial fibrosis. All animals on the glycated protein diet, and only one of the animals on the control diet showed more than 13% damaged glomeruli. The probability of this happening by chance is less than 2%. In addition to the pathological changes observed in the glomeruli, a number of hyalinated casts within tubules were observed. More of these hyalinated casts were found in animals on the glycated diet, although these were not quantitated. Increased levels of NAGase were also observed in the animals on the glycated diet.

Based on the results of this experiment, the glycated diet appeared to cause the test animals to develop a series of histological lesions similar to those seen in the diabetic kidney.

Example 12

Carcinogenic Effects of Fructoselysine Pathway:

To investigate the carcinogenic potential of metabolites formed in the fructoselysine pathway, experiments were conducted on a strain of rats with a high susceptibility to kidney carcinomas.

Four rats were put on a glycated protein diet and three rats on a control diet. After ten weeks on the diet, the animals were sacrificed and their kidneys examined.

In all four animals on the diet, kidney carcinomas of size greater than 1 mm were found, whereas no lesions this large were found in the control animals. The probability of this happening by chance is less than 2%.

The data demonstrate that there are elevated 3DG levels, caused by the excess fructoselysine coming from the glycated protein in the diet, in the kidney tubular cells (known to be the cell of origin of most kidney carcinomas), and the 3DG can interact with the cellular DNA, leading to a variety of mutagenic and ultimately carcinogenic events. The possibility exists that this process is important in the development of human cancers in the kidney and elsewhere.

Example 13

Dietary Effects of Glycated Protein Diet on Renal Cell Carcinoma in Susceptible Rats:

In addition to the experiments described above, experiments were performed to assess the relationship between a glycated protein diet and renal cell carcinoma.

Twenty-eight rats with a mutation making them susceptible to the development of kidney carcinoma were divided into two cohorts. One cohort was fed a glycated protein diet and the other cohort was on a control diet. The glycated protein diet consisted of a standard nutritious diet to which 3% glycated protein had been added. The glycated protein was made by mixing together casein and glucose (2:1), adding water (2×the weight of the dried material), and baking the mixture at 60° C. for 72 hours. The control was prepared in the same way except that no water was used and the casein and glucose were not mixed prior to baking. Rats were placed on the diets immediately following weaning at three weeks of age and maintained on the diets ad libitum for the next 16 weeks. The animals were then sacrificed, the kidneys fixed, and hematoxylin and eosin sections were prepared.

The histological samples were examined by a pathologist. Four types of lesions were identified. These include: cysts; very small collections of tumor-like cells, typically less than 10 cells; small tumors, 0.5 mm or less; and tumors greater than 0.5 mm. For the four types of lesions, more lesions were observed in the animals on the glycated diet than on the control diet, as shown in the following table (Table A).

TABLE A

|  | CYSTS | ≤10 CELLS | ≤0.5 mm | >0.5 mm | TOTAL |
| --- | --- | --- | --- | --- | --- |
| CONTROL | 2 | 9 | 9 | 3 | 23 |
| GLYCATED | 9 | 21 | 32 | 6 | 68 |

To summarize the results, the average number of lesions per kidney section was computed for each diet. These were 0.82±0.74 and 2.43±2.33 in the control and glycated diet, respectively. The likelihood of this happening by chance is about 2 in 100,000.

These results provide strong support for the premise that the effects of the lysine recovery pathway, the discovery of which underlies the present invention, extend to causing mutations, and thus produce a carcinogenic effect as well. These results provide a basis for the development of therapeutic methods and agents to inhibit this pathway in order to reduce cancer in the kidney as well as in other organs where this pathway may have similar effects.

Example 14

Urinary Excretion of 3-deoxy-fructose is Indicative of Progression to Microalbuminuria in Patients with Type I Diabetes:

As set forth herein, serum levels of the glycation intermediate, three deoxy-glucosone (3DG) and its reductive detoxification product, three deoxy-fructose (3DF), are elevated in diabetes. The relationship between baseline levels of these compounds and subsequent progression of microalbuminuria (MA) has been examined in a group of 39 individuals from a prospective cohort of patients at the Joslin Diabetes Center with insulin-dependent diabetes mellitus (IDDM) and microalbuminuria (based on multiple measurements during the two years of baseline starting between 1990-1993) and not on ACE inhibitors.

Baseline levels of 3DF and 3DG in random spot urines were measured by HPLC and GC-MS. Individuals that progressed to either a higher level of MA or proteinuria in the next four years (n=24) had significantly higher baseline levels of log 3DF/urinary creatinine ratios compared to non-progressors (n=15) (p=0.02).

Baseline levels determined in this study were approximately 0.24 μmole/mg of creatinine in the progressors vs. approximately 0.18 μmole/mg of creatinine ratios in the non-progressors. Baseline 3DG/urine creatinine ratios did not differ between the groups. Adjustment of the baseline level of $HgA_{Ic}$ (the major fraction of glycosylated hemoglobin) did not substantially alter these findings. These results provide additional evidence of the association between urinary 3DF and progression of kidney complications on diabetes.

a. Quantification of 3-deoxyfructose:

Samples were processed by passing a 0.3 ml aliquot of the test sample through an ion-exchange column containing 0.15 ml of AG 1-X8 and 0.15 ml of AG 50W-X8 resins. The columns were then washed twice with 0.3 ml deionized water, aspirated to remove free liquid and filtered through a 0.45 mm Millipore filter.

Injections (50 μl) of the treated samples were analyzed using a Dionex DX 500 chromatography system. A carbopac PA1 anion-exchange column was employed with an eluant consisting of 16% sodium hydroxide (200 mM) and 84% deionized water. 3DF was detected electrochemically using a pulsed amperometric detector. Standard 3DF solutions spanning the anticipated 3DF concentrations were run both before and after each unknown sample.

b. Measurement of Urine Creatinine:

Urine creatinine concentrations were determined by the end-point colorimetric method (Sigma Diagnostic kit 555-A) modified for use with a plate reader. Creatinine concentrations were assessed to normalize urine volumes for measuring metabolite levels present therein.

c. Measurement of Albumin in the Urine:

To assess albumin levels in the urine of the test subjects, spot urines were collected and immunoephelometry performed on a BN 100 apparatus with the N-albumin kit (Behring). Anti-albumin antibodies are commercially available. Albumin levels in urine may be assessed by any suitable assay including but not limited to ELISA assays, radioimmunoassays, Western, and dot blotting.

Based on the data obtained in the study of the Joslin Diabetes Center patients, it appears that elevated levels of urinary 3DF are associated with progression to microalbuminuria in diabetes. This observation provides a new diagnostic parameter for assessing the likelihood of progression to serious kidney complications in patients afflicted with diabetes.

Example 15

3-O-methyl Sorbitollysine Lowers Systemic Levels of 3DG in Normal and Diabetic Rats:

A cohort of twelve diabetic rats was divided into two groups of six. The first group received saline-only injections, and the second received injections of 3-O-methyl sorbitollysine (50 mg/kg body weight) in saline solution. The same procedure was conducted on a cohort of twelve non-diabetic rats.

As summarized in Table B, within one week, the 3-O-methyl sorbitollysine treatment significantly reduced plasma 3DG levels as compared to the respective saline controls in both diabetic and non-diabetic rats.

TABLE B

3-O-Methyl sorbitollysine (3-OMe) reduces plasma 3DG levels in diabetic and non-diabetic rats.

|  | Diabetic rats | Non-diabetic rats |
|---|---|---|
| Saline only | 0.94 ± 0.28 μM (n = 6) | 0.23 ± 0.07 μM (n = 6) |
| 3-OMe | 0.44 ± 0.10 μM (n = 6) | 0.13 ± 0.02 μM (n = 7) |
| % Reduction | 53% | 43% |
| t-test | p = 0.0006 | p = 0.0024 |

The ability of 3-O-methyl sorbitollysine to reduce systemic 3DG levels suggests that diabetic complications other than nephropathy (e.g., retinopathy and stiffening of the aorta) may also be controllable by amadorase inhibitor therapy.

Example 16

Locus of 3-O-methyl Sorbitollysine Uptake In Vivo is the Kidney:

Six rats were injected intraperitoneally with 13.5 mmoles (4.4 mg) of 3-O-methyl sorbitollysine. Urine was collected for 3 hours, after which the rats were sacrificed. The tissues to be analyzed were removed and freeze clamped in liquid nitrogen. Perchloric acid extracts of the tissues were used for metabolite analysis. The tissues examined were taken from the brain, heart, muscle, sciatic nerve, spleen, pancreas, liver, and kidney. Plasma was also analyzed.

The only tissue extract found to contain 3-O-methyl sorbitollysine was that of the kidney. The urine also contained 3-O-methyl sorbitollysine, but plasma did not. The percentage of the injected dose recovered from urine and kidney varied between 39 and 96%, as shown in Table C, below.

TABLE C

| Rat # | nmols 3OMeSL* Injected | Nmols 3OMeSL in urine | nmols 3OMeSL in kidneys | total 3OMeSL recovered | % 3OMeSL recovered |
|---|---|---|---|---|---|
| 2084 | 13500 | 2940 | 10071 | 13011 | 96.4 |
| 2085 | 13500 | 1675 | 6582 | 8257 | 61.2 |
| 2086 | 13500 | 1778 | 5373 | 7151 | 53.0 |
| 2087 | 13500 | 2360 | 4833 | 7193 | 53.3 |
| 2088 | 13500 | 4200 | 8155 | 12355 | 91.5 |
| 2089 | 13500 | 1355 | 3880 | 5235 | 38.8 |

*3-O-methyl sorbitollysine

Example 17

Amadorase/Fructosamine Kinase Activity Accounts for a Majority of 3DG Production:

Enzymatic production of 3DG was demonstrated in an in vitro assay with various key components (10 mM Mg-ATP, partially purified amadorase, 2.6 mM FL) omitted from the reaction in order to assess their importance in 3DG production.

The results show that 3DG production is 20-fold higher in the presence of kidney extract containing amadorase and its substrates (compare Table D, reactions 1 and 3). Clearly, the vast majority of 3DG production is enzymatically mediated in the presence of amadorase.

TABLE D

Amadorase-dependent production of 3DG after 24 hours

| Reaction | Amadorase | ATP | FL (mM) | FL3P (mM) | 3DG (mM) |
|---|---|---|---|---|---|
| 1 | + | + | 2.6 | 0.2 | 1.58 |
| 2 | + | − | 2.6 | 0 | 0.08 |
| 3 | − | + | 2.6 | 0 | 0.09 |
| 4 | − | − | 2.6 | 0 | 0.08 |
| 5 | + | + | 0 | 0 | 0 |
| 6 | − | + | 0 | 0 | 0 |

Example 18

Effects of 3DG, and Inhibition of 3DG, on Collagen Crosslinking:

Collagen is present at high levels in skin. To this end, it was determined what effect 3DG has on collagen crosslinking.

Collagen I was incubated in the presence or absence of 3DG in vitro. Calf skin collagen Type 1 (1.3 mg; Sigma) was incubated in 20 mM Na-phosphate buffer, pH 7.25, either alone, with 5 mM 3DG, or with 5 mM 3DG plus 10 mM arginine, in a total volume of 1 ml at 37° C. for 24 hours and then frozen and lyophilized. The residue was dissolved in 0.5 ml of 70% formic acid and cyanogen bromide was added (20:1, w/w). This solution was incubated at 30° C. for 18 hours. Samples were dialyzed against 0.125 M Tris, pH 6.8, containing 2% SDS and 2% glycerol, in dialysis tubing with a molecular weight cutoff of 10,000. The samples were all adjusted to a volume of 1 ml. The extent of collagen crosslinking was determined by applying equal volumes of sample and analyzing by SDS-PAGE electrophoresis (16.5% Tris-tricine gel), as determined by the effects of 3DG on the migration of collagen.

It was found that treatment of collagen with 3DG caused the collagen to migrate as if it had a higher molecular weight, which is indicative of crosslinking. The image of the silver-stained gel in FIG. 12 demonstrates that there are fewer high molecular bands in the groups containing collagen alone or collagen plus 3DG plus arginine. There are more high molecular weight bands in the group treated with 3DG, in the absence of a 3DG inhibitor. There appears to be more protein in the sample treated with 3DG alone. Because all three samples started with the same mount of protein, without being bound by theory, it can be concluded that during dialysis fewer peptides escaped from the 3DG treated sample because more crosslinks were produced and higher molecular weight proteins were retained. In other words, there appears to be less protein in the control and 3DG plus arginine groups, because smaller molecular peptides diffused out during dialysis.

Example 19

Localization of 3DG in Skin:

The invention as described in the present disclosure identifies for the first time the presence of 3DG in skin.

A mouse skin model was used. One centimeter (1 cm) squares of skin were prepared and subjected to extraction with perchloric acid. 3DG was measured as described above. Six mice were used and the average amount of 3DG detected in the skin was 1.46+/−0.3 µM. This value was substantially higher than the plasma concentrations of 3DG detected in the same animals (0.19+/−0.05 µM). These data, and the data described below in Example 20, suggest that the high levels of 3DG in the skin are due to production of 3DG in the skin.

Example 20

Localization of Amadorase mRNA in Skin:

Although high levels of 3DG were found in skin (see previous Example), it was not known whether the 3DG was formed locally and whether skin had the ability to produce 3DG enzymatically. The presence of amadorase mRNA was analyzed and was utilized as one measure of the ability of skin to produce the 3DG present in skin (see previous example).

PolyA+ messenger RNA isolated from human kidney and skin was purchased from Stratagene. The mRNA was used in RT-PCR procedures. Using the published sequence for amadorase (Delpierre et al., 2000, Diabetes 49:10:1627-1634; Szwergold et al., 2001, Diabetes 50:2139-2147), a reverse primer to the 3' terminal end of the gene (bp 930-912) was subjected to RT to create a cDNA template for PCR. This same primer was used along with a forward primer from the middle of the amadorase gene (bp 412-431) to amplify the amadorase gene from the cDNA template. The product of the PCR should be a 519 bp fragment. Human skin and kidney samples were subjected to RT-PCR and analyzed by agarose gel electrophoresis, as were controls which contained no cDNA templates.

Figure 13:
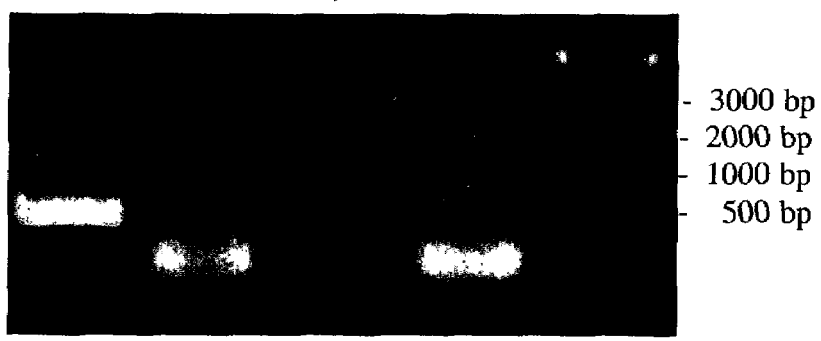
FIG. 13 is an image of an agarose gel demonstrating that the mRNA for amadorase/fructosamine kinase is present in human skin. RT-PCR was utilized and published amadorase sequences were used as the basis for preparing templates for PCR. Based on the primers used (see Examples) for the PCR reaction, the presence of a 519 bp fragment in the gel indicates the presence of amadorase mRNA. Expression of amadorase, as based on the presence of amadorase mRNA indicated by a 519 bp fragment, was found in the kidney (lane 1) and in the skin (lane 3). No 519 bp fragments were found in the control lanes, which contained primer but no template (lanes 2 and 4). Lane 5 contained DNA molecular weight markers.

The results demonstrate that skin does indeed express amadorase mRNA. Subsequent expression of the protein would account for production of 3DG in skin. As expected, a 519 bp product was observed (see FIG. 13). Not only was the 519 bp fragment found in kidney (lane 1), it was also found in skin (lane 3). The 519 bp fragment was not detected in the groups which received no cDNA template (lanes 2 and 4).

Example 21

Effects of Fructoselysine on Kidney Cells In Vitro:

As described above, a diet high in glycated proteins, e.g., fructoselysine, has a profound effect on metabolism in vivo. Therefore, the effects of fructoselysine were tested directly on kidney cells in vitro.

The results demonstrate that fructoselysine administered to kidney cells in vitro causes an increase in type IV collagen levels in the cells. Type IV collagen production was measured in mouse mesangial cells. Controls (grown with 10% glucose) produced 300 ng of Type IV collagen per 10,000 cells, whereas fructoselysine treated cells (5 or 10 mM fructoselysine with 10 mM glucose) produced 560 and 1100 ng/10,000 cells.

Example 22

Inhibition of 3DG by Inhibiting Amadorase mRNA and Protein:

3DG synthesis may be inhibited by inhibiting the components of the enzymatic pathway leading to its synthesis. This can be done in several ways. For example, the enzyme which leads to the synthesis of 3DG, called amadorase herein (a fructosamine-3-kinase) can be inhibited from acting using a compound as described above, but it can also be inhibited by blocking the synthesis of its message or protein or by blocking the protein itself, other than with a compound, as described above.

Amadorase mRNA and protein synthesis and function may be inhibited using compounds or molecules such as transcription or translation inhibitors, antibodies, antisense messages or oligonucleotides, or competitive inhibitors.

Nucleic Acid and Protein Sequences

The following represents the 988 bp mRNA-derived DNA sequence for amadorase (fructosamine-3-kinase), Accession No. NM_022158 (SEQ ID NO:1) (see FIG. 10):

The sequences identified above were submitted by Delpierre et al. (2000, Diabetes 49:16227-1634). The sequence data of Szwergold et al. (2001, Diabetes 50:2139-2147) are in excellent agreement with those of Delpierre et al. For example, the protein sequence deduced by Szwergold et al. (2001, Diabetes 50:2139-2147) is identical with the cloned human fructosamine-3-kinase sequence of Delpierre et al. (2000, Diabetes 49:16227-1634) in 307 of 309 amino acid residues. Thus, reliance on the published sequences of either group should not be a problem, however, to ensure that no problems arise when a sequence of the protein is to be used, only those portions of the sequence which are not different between the two published sequences will be used.

Example 23

Presence of Alpha-Dicarbonyl Sugars in Sweat

As disclosed herein, alpha-dicarbonyl sugars are present in skin, but their presence in sweat had not been determined.

```
  1 cgtcaagctt ggcacgaggc catggagcag ctgctgcgcg ccgagctgcg caccgcgacc
 61 ctgcgggcct tcggcggccc cggcgccggc tgcatcagcg agggccgagc ctacgacacg
121 gacgcaggcc cagtgttcgt caaagtcaac cgcaggacgc aggcccggca gatgtttgag
181 ggggaggtgg ccagcctgga ggccctccgg agcacgggcc tggtgcgggt gccgaggccc
241 atgaaggtca tcgacctgcc gggaggtggg gccgcctttg tgatggagca tttgaagatg
301 aagagcttga gcagtcaagc atcaaaactt ggagagcaga tggcagattt gcatctttac
361 aaccagaagc tcagggagaa gttgaaggag gaggagaaca cagtgggccg aagaggtgag
421 ggtgctgagc ctcagtatgt ggacaagttc ggcttccaca cggtgacgtg ctgcggcttc
481 atcccgcagg tgaatgagtg gcaggatgac tggccgacct ttttcgcccg gcaccggctc
541 caggcgcagc tggacctcat tgagaaggac tatgctgacc gagaggcacg agaactctgg
601 tcccggctac aggtgaagat cccggatctg ttttgtggcc tagagattgt ccccgcgttg
661 ctccacgggg atctctggtc gggaaacgtg gctgaggacg acgtggggcc cattatttac
721 gacccggctt ccttctatgg ccattccgag tttgaactgg caatcgcctt gatgtttggg
781 gggttcccca gatccttctt caccgcctac caccggaaga tccccaaggc tccgggcttc
841 gaccagcggc tgctgctcta ccagctgttt aactacctga accactggaa ccacttcggg
901 cgggagtaca ggagcccttc cttgggcacc atgcgaaggc tgctcaagta gcggcccctg
961 ccctcccttc ccctgtcccc gtccccgt
```

The following represents the 309 amino acid residue sequence of human amadorase (fructosamine-3-kinase), Accession No. NP_071441 (SEQ ID NO:2) (see FIG. 11):

One of the functions of skin is to act as an excretory organ, therefore, it was determined whether alpha-dicarbonyl sugars are excreted in sweat.

```
  1 meqllraelr tatlrafggp gagcisegra ydtdagpvfv kvnrrtqarq mfegevasle
 61 alrstglvrv prpmkvidlp gggaafvmeh lkmkslssqa sklgeqmadl hlynqklrek
121 lkeeentvgr rgegaepqyv dkfgfhtvtc cgfipqvnew qddwptffar hrlqaqldli
181 ekdyadrear elwsrlqvki pdlfcgleiv pallhgdlws gnvaeddvgp iiydpasfyg
241 hsefelaial mfggfprsff tayhrkipka pgfdqrllly qlfhylnhwn hfgreyrsps
301 lgtmrrllk
```

Samples of human sweat were analyzed for the presence of 3DG, as described above. Samples from four subjects were obtained and 3DG was determined to be present at levels of 0.189, 2.8, 0.312, and 0.11 µM, respectively. Therefore, the results demonstrate the presence of 3DG in sweat.

Example 24

Effects of DYN 12 (3-O-methylsorbitollysine) on Skin Elasticity

Administration of DYN 12, a small molecule inhibitor of amadorase, reduces 3DG levels in the plasma of diabetic and non-diabetic animals (Kappler et al., 2002, Diabetes Technol. Ther., Winter 3:4:606-609).

Experiments were performed to determine the effects of DYN 12 on the loss of skin elasticity associated with diabetes. To this end, two groups of STZ-diabetic rats and two groups of normal rats were subjected to treatment with DYN 12 or saline. One group of STZ-diabetic rats (n=9) received daily subcutaneous injections of DYN 12 at 50 mg/kg for eight weeks, as did one group of normal rats (n=6). A group of control diabetic rats (n=10) and a group of normal rats (n=6) received saline instead of DYN 12. One rat was removed from the diabetic DYN 12 group after 2 weeks because its blood glucose readings were inconsistent (too low) with other diabetic rats.

A non-invasive procedure based on CyberDERM, Inc. technology utilizing a skin elasticity measurement device was used to test the effects of DYN 12 treatment on skin elasticity. The procedure provides for non-invasive measurement of skin elasticity based upon the amount of vacuum pull required to displace skin. A suction cup probe is adhered to an area of shaved skin in order to form an airtight seal. Then, a vacuum is applied to the area of the skin inside the suction cup until the skin is displaced past a sensor located inside the probe. Accordingly, the more pressure that is required to displace the skin, the less elastic the skin is.

Figure 14:
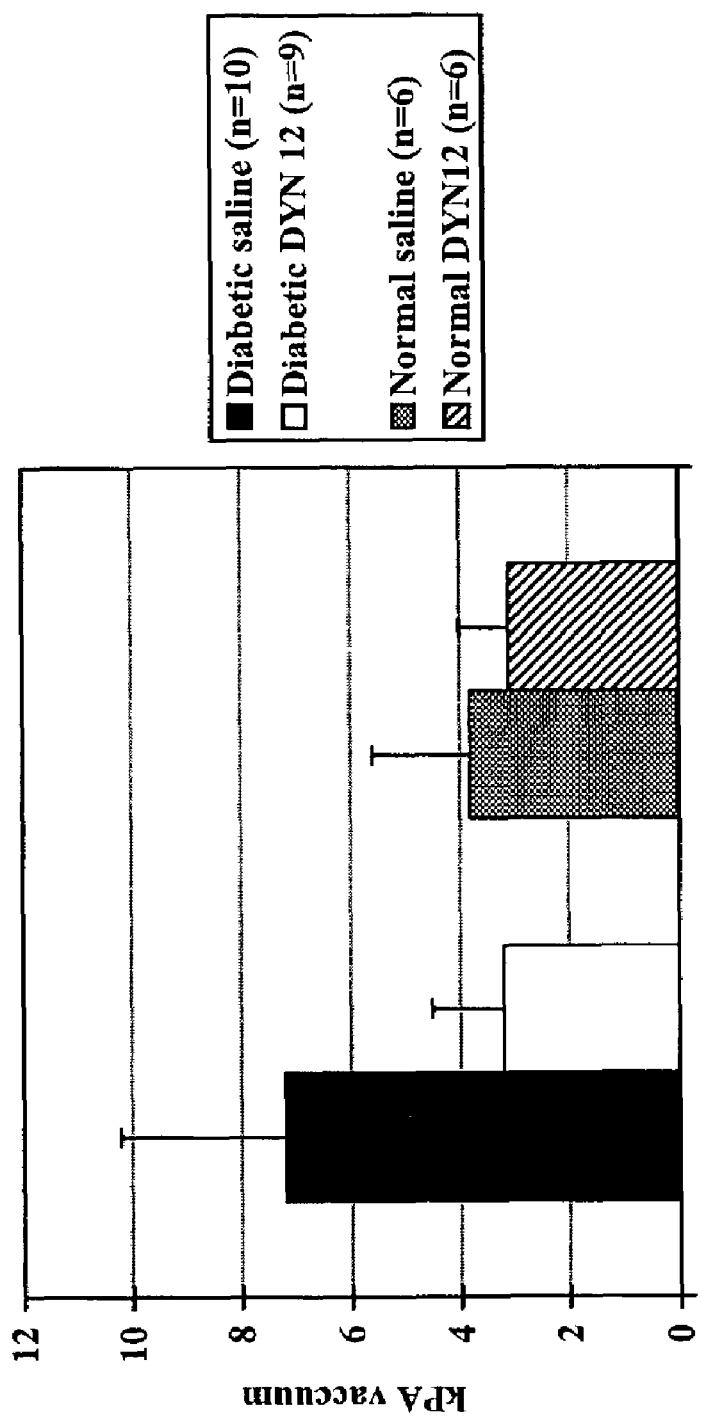
FIG. 14 is a graphic illustration of the effects of DYN 12 (3-O-methylsorbitollysine) treatment on skin elasticity. Diabetic or normal rats were treated with DYN 12 (50 mg/kg daily) or saline for eight weeks and then subjected to skin elasticity tests. The four groups used included diabetic controls (saline injection; solid black bar), diabetics treated with DYN 12 (open bar), normal animal controls (saline injections; stippled bar), and normal animals treated with DYN 12 (cross-hatched bar). Data are expressed in kilopascals (kPA).

The data demonstrate that after eight weeks of treatment skin elasticity in diabetic rats treated with DYN 12 was greater than skin elasticity in diabetic animals which were treated with saline. As seen in FIG. 14, the amount of pressure needed to displace the skin of diabetic rats treated with saline (7.2+/−3.0 kPA) was approximately 2 to 2.25 fold higher than the pressure needed to displace the skin of diabetic animals treated with DYN 12 (3.2+/−1.2 kPA). Also, the elasticity value observed in diabetic rats treated with DYN 12 was not statistically different from the value found in non-diabetic rats treated with saline (p=0.39) (Table E). Thus, the result of treatment of diabetic animals with DYN 12, an indirect inhibitor of 3DG, was skin with greater elasticity than skin in diabetic animals which received only saline.

TABLE E

Statistical Analysis and Comparison of Cohort Groups.

| Group 1 | Group 2 | p value |
|---|---|---|
| Diabetic saline | Non-diabetic saline | p = 0.01 |
| Diabetic saline | Diabetic DYN 12 | p = 0.001 |
| Diabetic saline | Non-diabetic DYN 12 | p = 0.003 |
| Diabetic DYN 12 | Non-diabetic DYN 12 | p = 0.39 |
| Diabetic DYN 12 | Non-diabetic saline | p = 0.26 |
| Non-diabetic saline | Non-diabetic DYN 12 | p = 0.20 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting 3-Deoxyglucosone (3DG) synthesis in the skin of a mammal, said method comprising administering to a mammal in need thereof an effective amount of meglumine or a salt thereof to inhibit said 3DG synthesis, further wherein said meglumine or salt thereof is administered via a topical route in a pharmaceutical composition, selected from the group consisting of a lotion, a cream, a gel, a liniment, an ointment, a paste, a solution, a powder, and a suspension.

2. The method of claim 1, wherein said meglumine or a salt thereof inhibits 3DG accumulation in said skin.

3. The method of claim 1, wherein said meglumine or a salt thereof inhibits induction of said 3DG synthesis.

4. A method of treating skin aging in a mammal, said method comprising, administering to a mammal in need thereof an effective amount of meglumine or a salt thereof which inhibits at least one of the members of the group consisting of the production of said 3DG, the accumulation of said 3DG and the function of said 3DG in skin, further wherein said meglumine or salt thereof is administered via a topical route in a pharmaceutical composition selected from the group consisting of a lotion, a cream, a gel, a liniment, an ointment, a paste, a solution, a powder, and a suspension.

5. The method of claim 1, wherein said composition further comprises a moisturizer, a humectant, a demulcent, oil, water, an emulsifier, a thickener, a thinner, a surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

6. The method of claim 4, wherein said meglumine or a salt thereof is administered at a frequency selected from the group consisting of once a day, twice a day, three times a day, four times a day, once a week, twice a week, once a month, and twice a month.

7. The method of claim 4, wherein said meglumine or a salt thereof is administered at a dosage ranging from about 1 ng/kg/application to about 100 g/kg/application.

8. The method of claim 4, wherein said meglumine or a salt thereof is administered at a dosage ranging from about 1 ng/kg/application to about 100 mg/kg/application.

9. The method of claim 4, wherein said meglumine or a salt thereof is administered as a controlled-release formulation.

10. The method of claim 9, wherein said meglumine or a salt thereof comprises from about 0.0001% to about 15% by weight of the composition.

11. The method of claim 1, wherein said meglumine or a salt thereof is administered at a frequency selected from the group consisting of once a day, twice a day, three times a day, four times a day, once a week, twice a week, once a month, and twice a month.

12. The method of claim 1, wherein said meglumine or a salt thereof is administered at a dosage ranging from about 1 ng/kg/application to about 100 g/kg/application.

13. The method of claim 1, wherein said meglumine or a salt thereof is administered at a dosage ranging from about 1 ng/kg/application to about 100 mg/kg/application.

14. The method of claim 1, wherein said meglumine or a salt thereof is administered as a controlled-release formulation.

15. The method of claim 14, wherein said meglumine or a salt thereof comprises from about 0.0001% to about 15% by weight of the composition.

16. The method of claim 4, wherein said composition further comprises a moisturizer, a humectant, a demulcent, oil, water, an emulsifier, a thickener, a thinner, a surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

17. The method of claim 1, wherein said mammal is a human.

18. The method of claim 4, wherein said mammal is a human.

\* \* \* \* \*

SEQUENCE LISTING

```
<160> NUMBER OF SEQ ID NOS: 2

<210> SEQ ID NO 1
<211> LENGTH: 988
<212> TYPE: DNA
<213> ORGANISM: Homo sapiens

<400> SEQUENCE: 1
cgtcaagctt ggcacgaggc catggagcag ctgctgcgcg ccgagctgcg caccgcgacc      60
ctgcgggcct tcggcggccc cggcgccggc tgcatcagcg agggccgagc ctacgacacg     120
gacgcaggcc cagtgttcgt caaagtcaac cgcaggacgc aggcccggca gatgtttgag     180
ggggaggtgg ccagcctgga ggccctccgg agcacgggcc tggtgcgggt gccgaggccc     240
atgaaggtca tcgacctgcc ggggaggtggg gccgcctttg tgatggagca tttgaagatg     300
aagagcttga gcagtcaagc atcaaaactt ggagagcaga tggcagattt gcatctttac     360
aaccagaagc tcagggagaa gttgaaggag gaggagaaca cagtgggccg aagaggtgag     420
ggtgctgagc ctcagtatgt ggacaagttc ggcttccaca cggtgacgtg ctgcggcttc     480
atcccgcagg tgaatgagtg gcaggatgac tggccgacct ttttcgcccg gcaccggctc     540
caggcgcagc tggacctcat tgagaaggac tatgctgacc gagaggcacg agaactctgg     600
```

-continued

```
tcccggctac aggtgaagat cccggatctg ttttgtggcc tagagattgt ccccgcgttg    660
ctccacgggg atctctggtc gggaaacgtg gctgaggacg acgtgggggcc cattatttac   720 gacccggctt ccttctatgg ccattccgag tttgaactgg caatcgcctt gatgtttggg   780
gggttcccca gatccttctt caccgcctac accggaagaa tccccaaggc tccgggcttc   840
gaccagcggc tgctgctcta ccagctgttt aactacctga accactggaa ccacttcggg   900
cgggagtaca ggagcccttc cttgggcacc atgcgaaggc tgctcaagta gcggcccctg   960
ccctcccttc cctgtcccc gtccccgt                                        988
```

<210> SEQ ID NO 2
<211> LENGTH: 309
<212> TYPE: PRT
<213> ORGANISM: Homo sapiens

<400> SEQUENCE: 2

```
Met Glu Gln Leu Leu Arg Ala Glu Leu Arg Thr Ala Thr Leu Arg Ala
1               5                   10                  15

Phe Gly Gly Pro Gly Ala Gly Cys Ile Ser Glu Gly Arg Ala Tyr Asp
                20                  25                  30

Thr Asp Ala Gly Pro Val Phe Val Lys Val Asn Arg Arg Thr Gln Ala
            35                  40                  45

Arg Gln Met Phe Glu Gly Glu Val Ala Ser Leu Glu Ala Leu Arg Ser
        50                  55                  60

Thr Gly Leu Val Arg Val Pro Arg Pro Met Lys Val Ile Asp Leu Pro
65                  70                  75                  80

Gly Gly Gly Ala Ala Phe Val Met Glu His Leu Lys Met Lys Ser Leu
                85                  90                  95

Ser Ser Gln Ala Ser Lys Leu Gly Glu Gln Met Ala Asp Leu His Leu
                100                 105                 110

Tyr Asn Gln Lys Leu Arg Glu Lys Leu Lys Glu Glu Asn Thr Val
                115                 120                 125

Gly Arg Arg Gly Glu Gly Ala Glu Pro Gln Tyr Val Asp Lys Phe Gly
            130                 135                 140

Phe His Thr Val Thr Cys Cys Gly Phe Ile Pro Gln Val Asn Glu Trp
145                 150                 155                 160

Gln Asp Asp Trp Pro Thr Phe Phe Ala Arg His Arg Leu Gln Ala Gln
                165                 170                 175

Leu Asp Leu Ile Glu Lys Asp Tyr Ala Asp Arg Glu Ala Arg Glu Leu
            180                 185                 190

Trp Ser Arg Leu Gln Val Lys Ile Pro Asp Leu Phe Cys Gly Leu Glu
        195                 200                 205

Ile Val Pro Ala Leu Leu His Gly Asp Leu Trp Ser Gly Asn Val Ala
    210                 215                 220

Glu Asp Asp Val Gly Pro Ile Ile Tyr Asp Pro Ala Ser Phe Tyr Gly
225                 230                 235                 240

His Ser Glu Phe Glu Leu Ala Ile Ala Leu Met Phe Gly Gly Phe Pro
                245                 250                 255

Arg Ser Phe Phe Thr Ala Tyr His Arg Lys Ile Pro Lys Ala Pro Gly
            260                 265                 270

Phe Asp Gln Arg Leu Leu Leu Tyr Gln Leu Phe Asn Tyr Leu Asn His
        275                 280                 285
```

```
-continued

Trp Asn His Phe Gly Arg Glu Tyr Arg Ser Pro Ser Leu Gly Thr Met
    290                 295                 300

Arg Arg Leu Leu Lys
305
```